United States Patent
Yamagata et al.

(10) Patent No.: US 11,457,856 B2
(45) Date of Patent: Oct. 4, 2022

(54) INFORMATION PROCESSING DEVICE, INFORMATION PROCESSING METHOD, RECORDING MEDIUM STORING PROGRAM CODE, AND BIOMEDICAL-SIGNAL MEASURING SYSTEM

(71) Applicants: Hideaki Yamagata, Kanagawa (JP); Noriyuki Tomita, Ishikawa (JP); Eiichi Okumura, Ishikawa (JP)

(72) Inventors: Hideaki Yamagata, Kanagawa (JP); Noriyuki Tomita, Ishikawa (JP); Eiichi Okumura, Ishikawa (JP)

(73) Assignee: RICOH COMPANY, LTD., Tokyo (JP)

( * ) Notice: Subject to any disclaimer, the term of this patent is extended or adjusted under 35 U.S.C. 154(b) by 302 days.

(21) Appl. No.: 16/795,904

(22) Filed: Feb. 20, 2020

(65) Prior Publication Data
US 2020/0289006 A1 Sep. 17, 2020

(30) Foreign Application Priority Data
Mar. 13, 2019 (JP) ............................. JP2019-045904

(51) Int. Cl.
*A61B 5/374* (2021.01)
*G16H 30/20* (2018.01)
(Continued)

(52) U.S. Cl.
CPC ............ *A61B 5/374* (2021.01); *A61B 5/0042* (2013.01); *A61B 5/245* (2021.01); *A61B 5/742* (2013.01); *G16H 30/20* (2018.01)

(58) Field of Classification Search
None
See application file for complete search history.

(56) References Cited

U.S. PATENT DOCUMENTS

| | | | |
|---|---|---|---|
| 2015/0227702 A1* | 8/2015 | Krishna | A61B 5/7257 705/2 |
| 2017/0172497 A1* | 6/2017 | Marquez Chin | G16H 20/30 |
| 2019/0236824 A1 | 8/2019 | Shinohara et al. | |

FOREIGN PATENT DOCUMENTS

| | | |
|---|---|---|
| JP | 2001-066355 | 3/2001 |
| JP | 2006-110234 | 4/2006 |
| JP | 2006-187306 | 7/2006 |

OTHER PUBLICATIONS

Translation of JP2006110234A (original provided by Applicant) (Year: 2006).*

* cited by examiner

*Primary Examiner* — Jay B Shah
(74) *Attorney, Agent, or Firm* — Harness, Dickey & Pierce, P.L.C.

(57) ABSTRACT

An information processing device, an information processing method, a recording medium storing a program, and a biomedical-signal measuring system. The information processing device includes circuitry to obtain specific information of a first intensity distribution of a biomedical signal from a source, the specific information being displayed on a display, and extract, based on the specific information, a specified area of the first intensity distribution to obtain second intensity distribution of the biomedical signal to be superimposed on an image indicative of the source. The information processing method includes obtaining specific information of a first intensity distribution of a biomedical signal from a prescribed source, the specific information being displayed on a display, and extracting, based on the specific information, a specified area of the first intensity distribution to obtain second intensity distribution of the biomedical signal to be superimposed on an image indicative of the source.

20 Claims, 57 Drawing Sheets

(51) Int. Cl.
*A61B 5/00* (2006.01)
*A61B 5/245* (2021.01)

FIG. 9

| No. | File | Time | Event | MEMO | Cluster |
|---|---|---|---|---|---|
| 2 ☐ | 001 | 00:09:30 | 🔥 | normal spike | B |
| 1 ☐ | 001 | 00:05:00 | 🔥 | strong spike | A |
| 0 ☐ | 000 | 00:00:00 | 🔥 | Dr.memo | A |

Annotation List ▼

☑ Show Markup on wave —— 560a

ANALYSIS COMPLETE

560

FIG. 21A
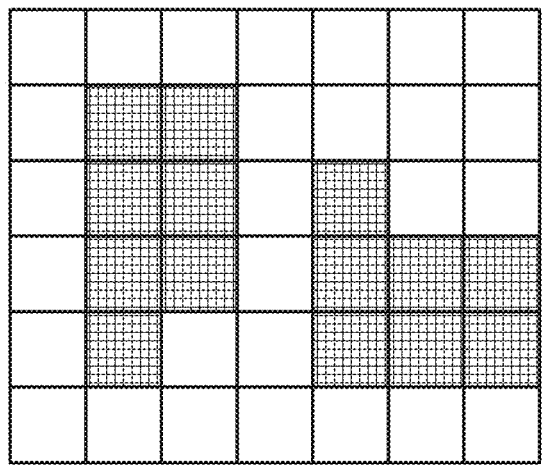
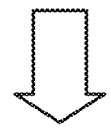
FIG. 21B
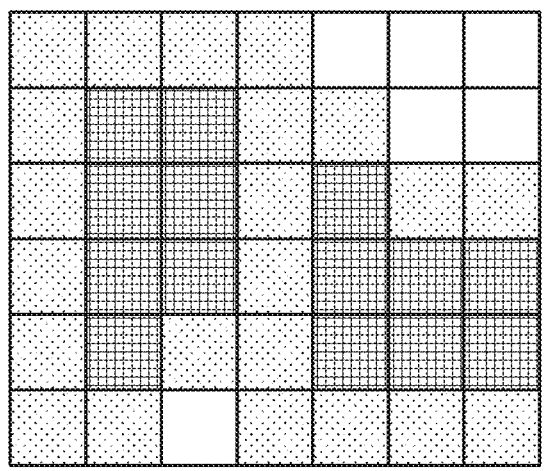
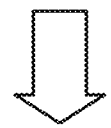
FIG. 21C
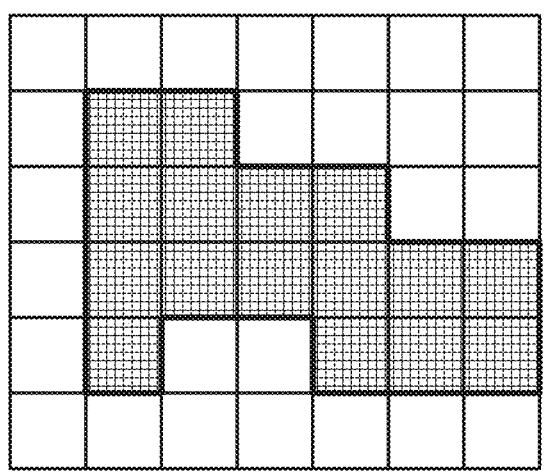

FIG. 30
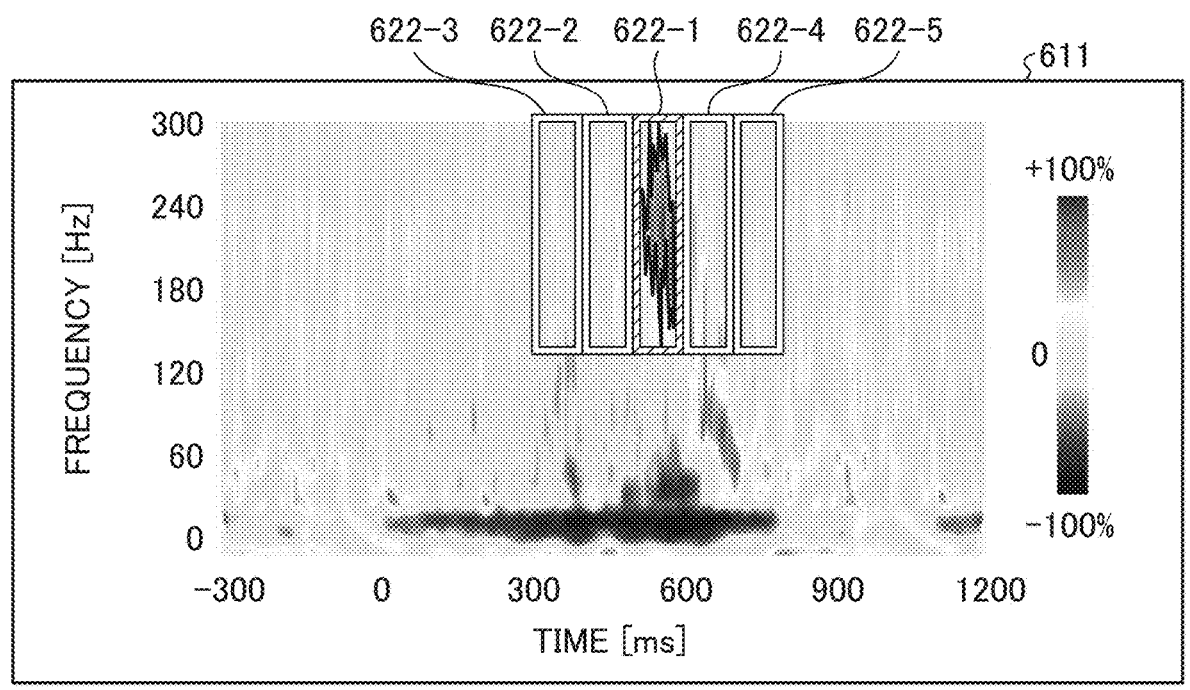
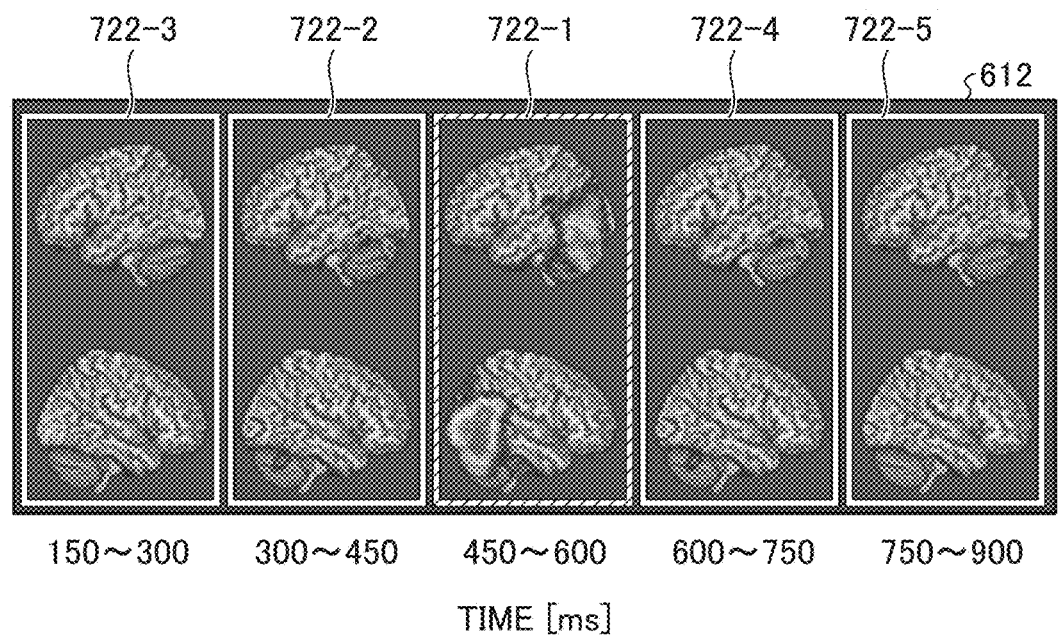

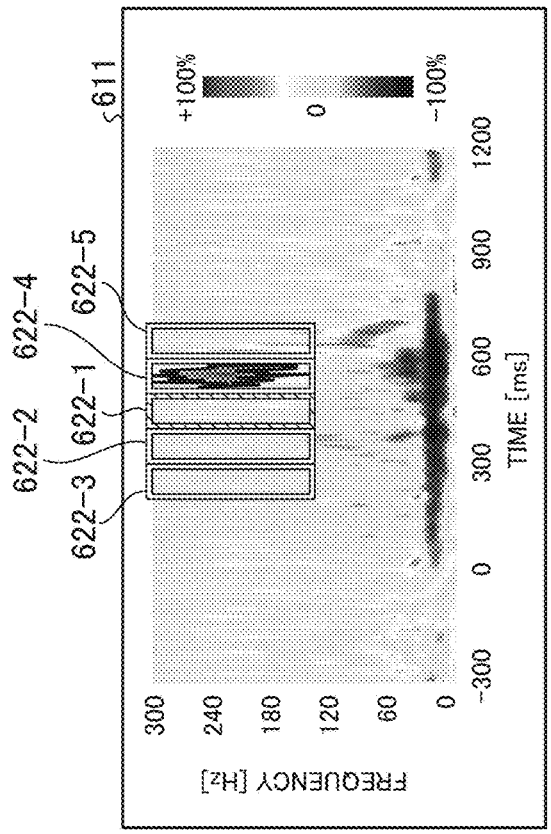
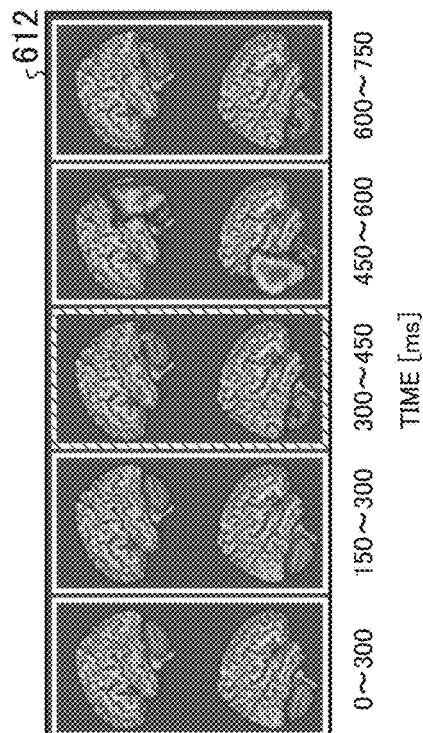
FIG. 31A
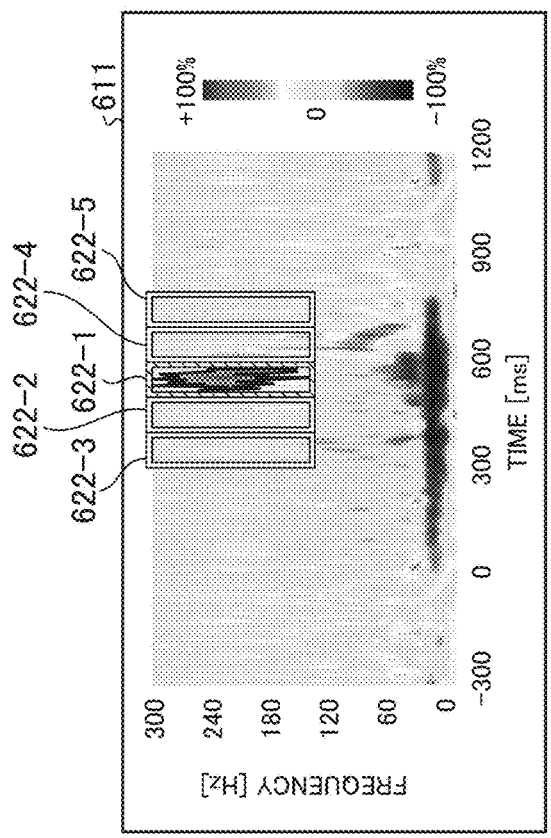
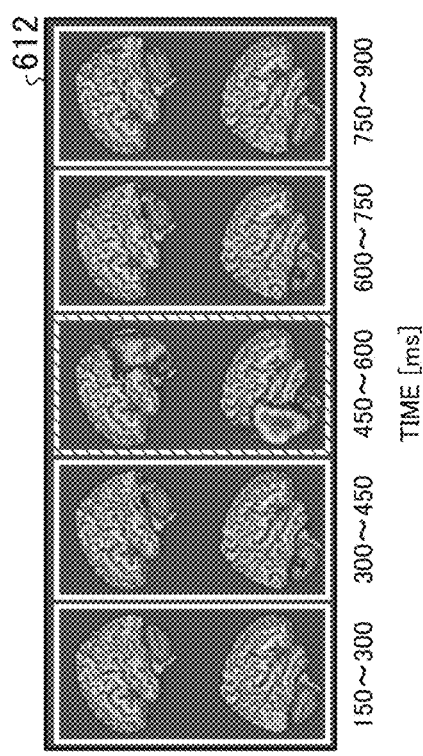
FIG. 31B

CHANGE VIEWPOINT OF TOP-RIGHT BRAIN IMAGE

VIEWPOINTS OF ALL BRAIN IMAGES IN SAME ROW ARE CHANGED

CHANGE VIEWPOINT OF TOP-RIGHT BRAIN IMAGE

VIEWPOINTS OF BRAIN IMAGES IN ALL ROWS ARE CHANGED

FIG. 35A
VIEWPOINT OF BRAIN IMAGES IN BOTTOM ROW IN FIG. 33  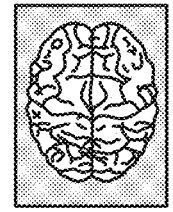  VIEWPOINT OF BRAIN IMAGES IN TOP ROW IN FIG. 33
CHANGE VIEWPOINT OF TOP-RIGHT BRAIN IMAGE IN FIG. 33
FIG. 35B
 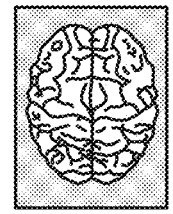 
VIEWPOINT OF BRAIN IMAGES IN TOP ROW IN FIG. 33 IS CHANGED
FIG. 35C
 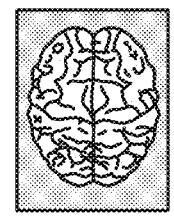
VIEWPOINT OF BRAIN IMAGES IN BOTTOM ROW IN FIG. 33 IS CHANGED BY SAME ANGLE IN SAME DIRECTION AS BRAINS IMAGES IN TOP ROW FIG. 36A
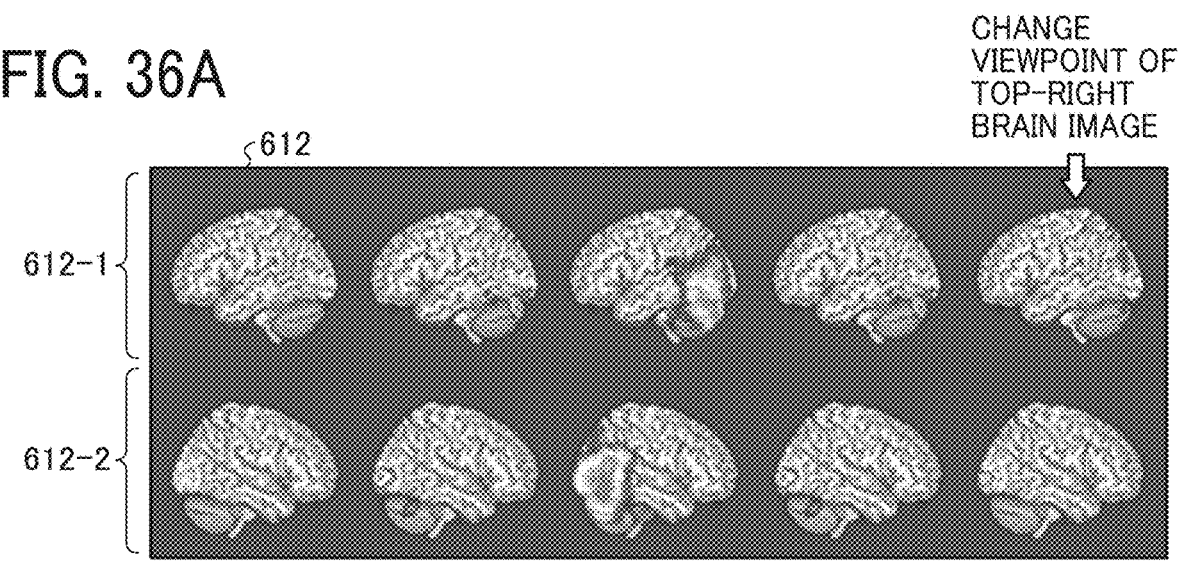
CHANGE VIEWPOINT OF TOP-RIGHT BRAIN IMAGE
FIG. 36B
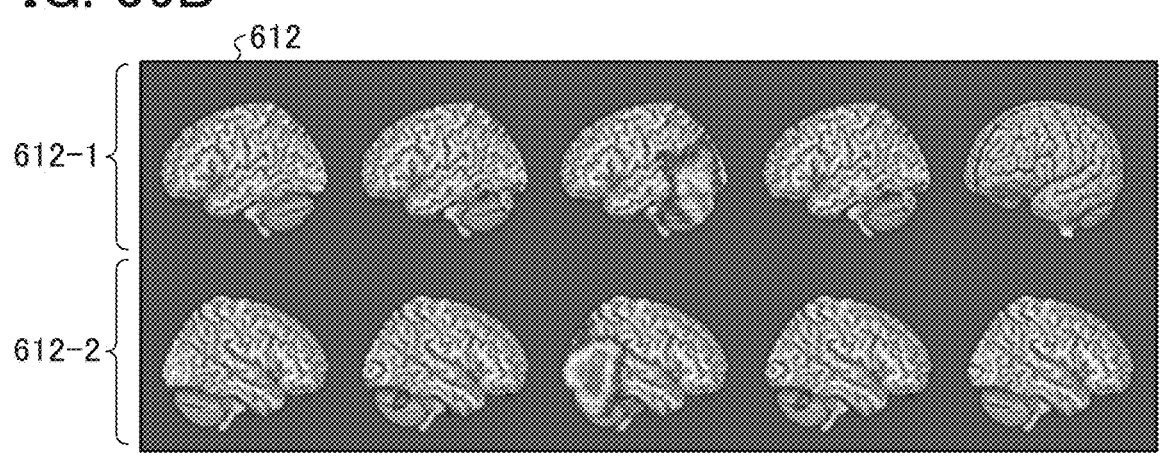
FIG. 36C    VIEWPOINTS OF BRAIN IMAGES IN ALL ROWS ARE CHANGED
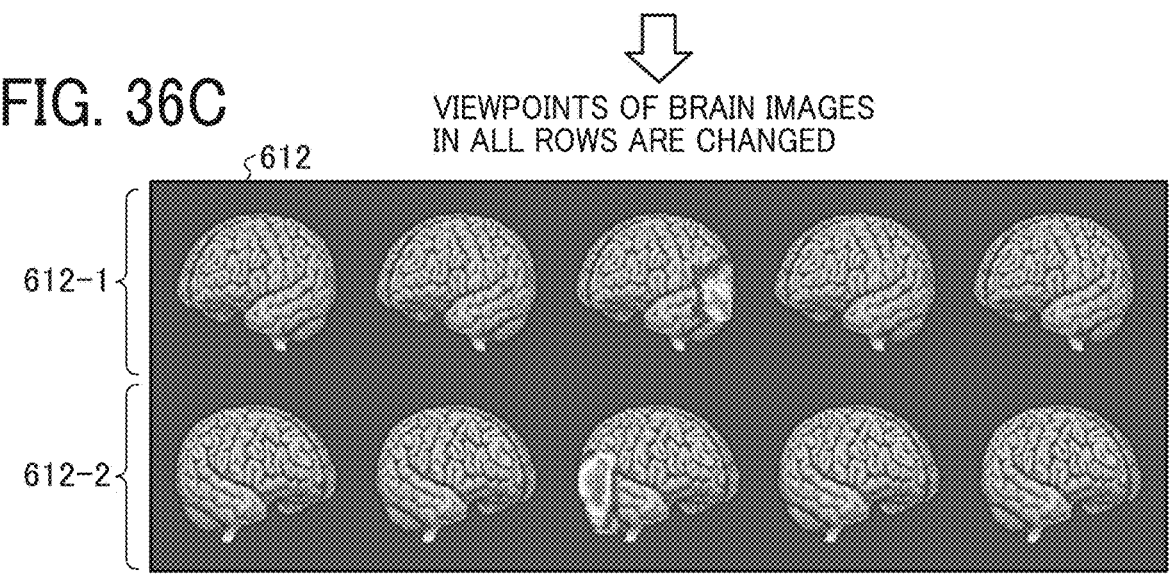

FIG. 37A  VIEWPOINT OF BRAIN IMAGES IN BOTTOM ROW IN FIG. 36    VIEWPOINT OF BRAIN IMAGES IN TOP ROW IN FIG. 36
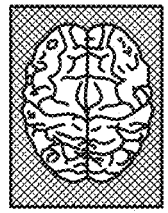
FIG. 37B
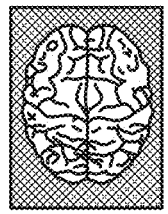
CHANGE VIEWPOINT OF TOP-RIGHT BRAIN IMAGE IN FIG. 36
FIG. 37C
VIEWPOINT OF BRAIN IMAGES IN TOP ROW IN FIG. 36 IS CHANGED
VIEWPOINT OF BRAIN IMAGES IN BOTTOM ROW IN FIG. 36 IS SYMMETRICALLY CHANGED BY SAME ANGLE AS BRAINS IMAGES IN TOP ROW WITH RESPECT TO SYMMETRY PLANE
SYMMETRY PLANE FIG. 61A
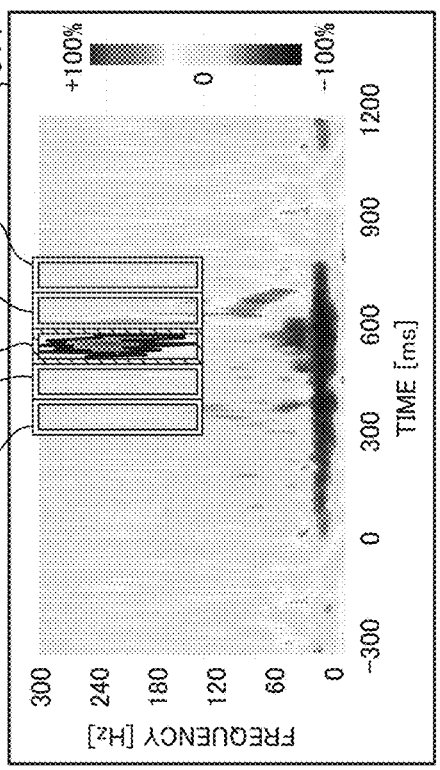
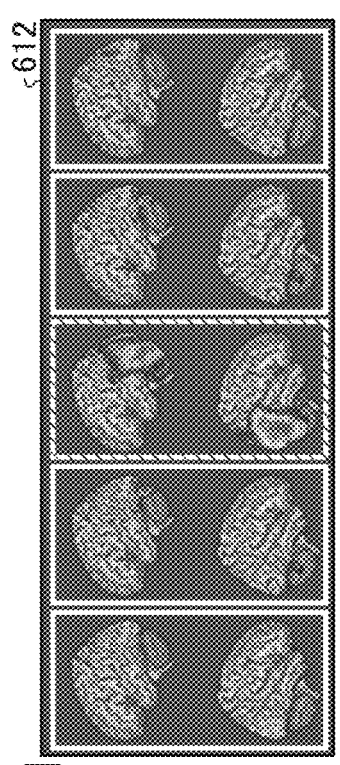
FIG. 61B
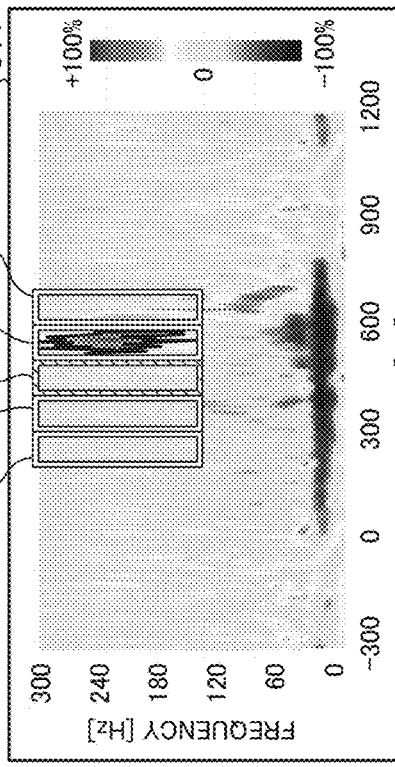
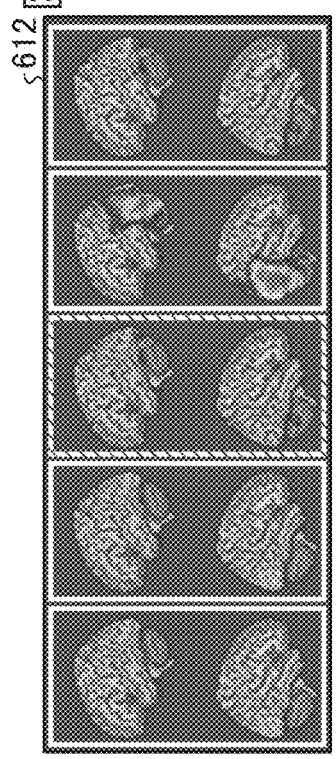

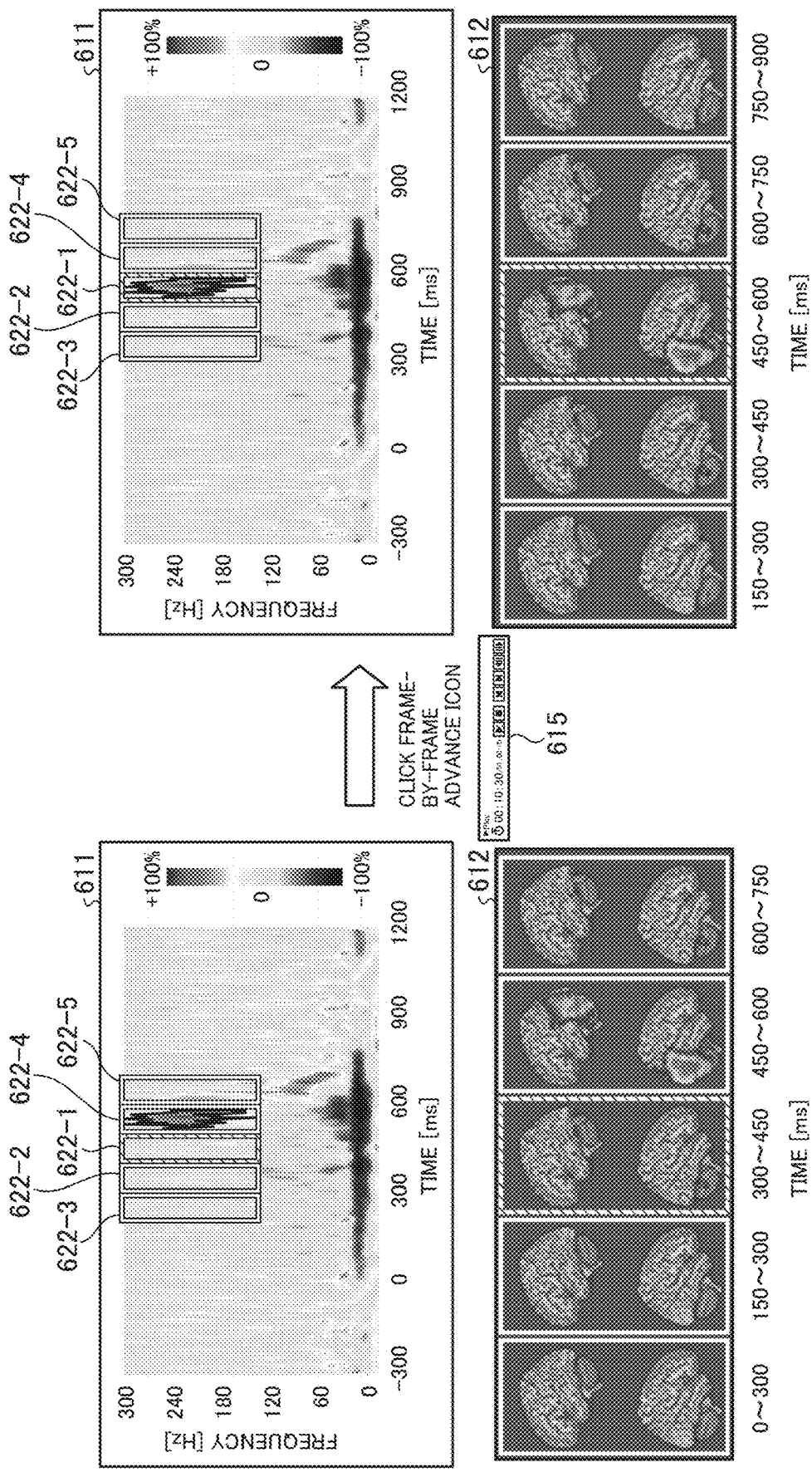

INFORMATION PROCESSING DEVICE, INFORMATION PROCESSING METHOD, RECORDING MEDIUM STORING PROGRAM CODE, AND BIOMEDICAL-SIGNAL MEASURING SYSTEM

CROSS-REFERENCE TO RELATED APPLICATION

This patent application is based on and claims priority pursuant to 35 U.S.C. § 119(a) to Japanese Patent Application No. 2019-045904, filed on Mar. 13, 2019, in the Japan Patent Office, the entire disclosure of which is hereby incorporated by reference herein.

BACKGROUND

Technical Field

Embodiments of the present disclosure relate to an information processing device, an information processing method, a recording medium storing program code, and a biomedical-signal measuring system.

Background Art

When brain surgery or the like is to be performed, a target site that is an affected site of the brain to be removed and sites to be conserved without removal need to be specified. The sites to be conserved include, for example, the visual area, auditory area, somatosensory area, motor area, and the language area of the brain. When some of such sites to be conserved is removed by mistake, the corresponding ability, including, for example, perception and movement, is impaired. For this reason, specifying a target site or sites to be conserved is crucial in performing brain surgery or the like. In order to scan the brain for activity in advance of such brain surgery or the like, physical phenomena inside the brain are measured using, for example, magneto-encephalography, electro-encephalography (EEG), functional Magnetic Resonance Imaging (fMRI), or functional near-infrared spectroscopy (fNIRS). Regarding the fMRI and fNIRS methods, biomedical signals are obtained by measuring the blood flow inside the brain. However, in view of the nature of such blood flow, the precision of the brain-activity measurement is limited. By contrast, magneto-encephalography measures the magnetic field caused by the electrical activity inside the brain, and the electro-encephalography (EEG) can measure the electrical activity inside the brain and obtain the biomedical signals in waveform. Such biomedical signals undergo, for example, time-frequency analysis and are displayed.

As such technologies to measure changes in brain activity using the time-frequency analysis, technologies to analyze changes in brain activity, which cannot be analyzed by averaging, are known in the art.

SUMMARY

Embodiments of the present disclosure described herein provide an information processing device, an information processing method, a non-transitory recording medium storing a program for causing a computer to execute the information processing method, and a biomedical-signal measuring system. The information processing device includes circuitry to obtain specific information of a first intensity distribution of a biomedical signal from a source, the specific information being displayed on a display, and extract, based on the specific information, a specified area of the first intensity distribution to obtain second intensity distribution of the biomedical signal to be superimposed on an image indicative of the source. The information processing method includes obtaining specific information of a first intensity distribution of a biomedical signal from a prescribed source, the specific information being displayed on a display, and extracting, based on the specific information, a specified area of the first intensity distribution to obtain second intensity distribution of the biomedical signal to be superimposed on an image indicative of the source.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

FIG. 9 is a diagram illustrating an updated annotation list according to embodiments of the present disclosure.

FIG. 21A, FIG. 21B, and FIG. 21C are diagrams illustrating closing operations, according to embodiments of the present disclosure.

FIG. 30 is a diagram in which rectangular areas are used to indicate to what time and frequency on a heat map each one of the images of a brain displayed as a three-dimensional image corresponds, according to embodiments of the present disclosure.

FIG. 31A and FIG. 31B are diagrams illustrating how the display on a three-dimensional image and the display of the rectangular regions on a heat map move as the three-dimensional image is dragged, according to embodiments of the present disclosure.

FIG. 35A, FIG. 35B, and FIG. 35C are diagrams illustrating in detail how the viewpoint is changed in FIG. 34A, FIG. 34B, and FIG. 34C.

FIG. 36A, FIG. 36B, and FIG. 36C are another set of diagrams illustrating how the viewpoints of all the brain images in all the rows are changed when one of the viewpoints of the brain displayed on a three-dimensional image is changed, according to embodiments of the present disclosure.

FIG. 37A, FIG. 37B, and FIG. 37C are diagrams illustrating the details of how the viewpoint is changed as in FIG. 36A, FIG. 36B, and FIG. 36C.

FIG. 61A and FIG. 61B are diagrams illustrating how the viewing of a heat map and a three-dimensional image are played back by operations on a replay control panel, according to embodiments of the present disclosure.

FIG. 63A and FIG. 63B are diagrams illustrating how the viewing of a heat map and a three-dimensional image are advanced on a frame-by-frame basis by operations on a replay control panel, according to embodiments of the present disclosure.

Figure 1:
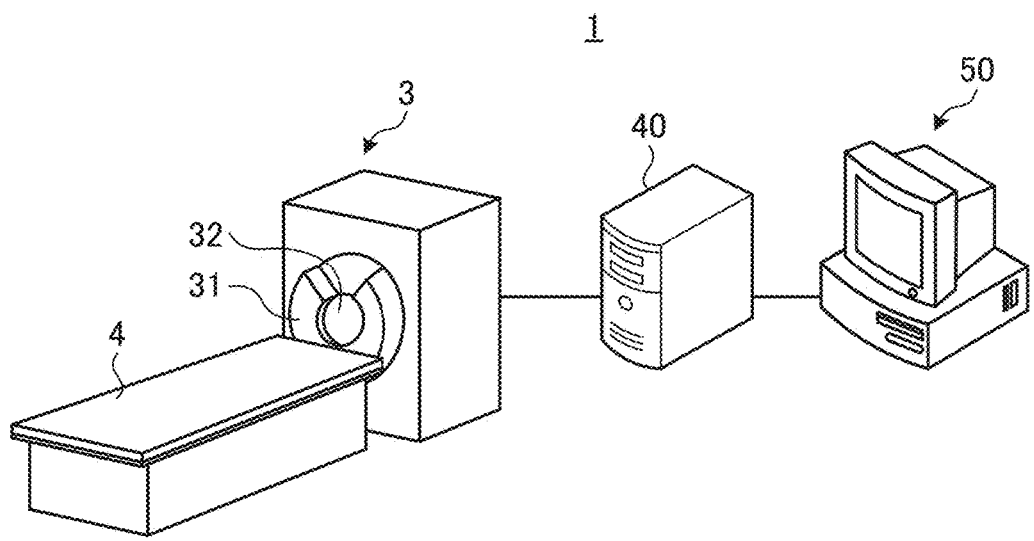
FIG. 1 is schematic diagram illustrating a biomedical-signal measuring system according to embodiments of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing network elements or control nodes. Such existing hardware may include one or more central processing units (CPUs), digital signal processors (DSPs), application-specific integrated circuits (ASICs), field-programmable gate arrays (FPGAs), computers or the like. These terms may be collectively referred to as processors.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Some embodiments of an information processing device, an information processing method, a non-transitory recording medium storing a program, and a biomedical-signal measuring system according to the present disclosure will be described below in detail with reference to the drawings. Note that numerous additional modifications and variations are possible in light of the above teachings. It is therefore to be understood that within the scope of the appended claims, the disclosure of the present disclosure may be practiced otherwise than as specifically described herein. For example, elements and/or features of different illustrative embodiments may be combined with each other and/or substituted for each other within the scope of this disclosure and appended claims.

A schematic configuration of the biomedical-signal measuring system 1 according to the present embodiment is described with reference to FIG. 1.

FIG. 1 is schematic diagram illustrating a biomedical-signal measuring system 1 according to embodiments of the present disclosure.

The biomedical-signal measuring system 1 (an example of an information processing system) measures various kinds of biomedical signals of a test subject such as magneto-encephalography (MEG) signals and electro-encephalography (EEG) signals, and displays the results of measurement. The biomedical signals to be measured are not limited to the magneto-encephalography (MEG) signals and electro-encephalography (EEG) signals as above, but may be, for example, any electrical signal that is caused by cardiac activity (i.e., any electrical signal that can be expressed in an electrocardiogram (ECG)). As illustrated in FIG. 1, the biomedical-signal measuring system 1 includes a measurement device 3 that measures at least one biomedical signal of a test subject, a server 40 that stores at least one biomedical signal measured by the measurement device 3, and an information processing device 50 that analyzes at least one biomedical signal stored on the server 40. In the present embodiment, as illustrated in FIG. 1, the server 40 and the information processing device 50 are described as separate units. However, no limitation is indicated thereby. For example, at least some of the functions of the server 40 may be implemented by the information processing device 50.

In the present embodiment as illustrated in FIG. 1, a test subject (person to be measured) lies on a measurement table 4 on his or her back with electrodes (or sensors) attached to his or her head to measure the electrical brain waves, and puts his or her head into a hollow 32 of a Dewar 31 of the measurement device 3. The Dewar 31 is a container of liquid helium that can be used at very low temperatures, and a number of magnetic sensors for measuring the brain magnetism are disposed on the inner surface of the hollow 32 of the Dewar 31. The measurement device 3 collects the electrical signals and the magnetic signals through the electrodes and the magnetic sensors, respectively, and outputs data including the collected electrical signals and magnetic signals to the server 40. Note that such collected electrical signals and magnetic signals may be referred to simply as "measurement data" in the following description of the present embodiment. The measurement data recorded on the server 40 is read and displayed by the information processing device 50, and is analyzed by the information processing device 50. As known in the art, the Dewar 31 equipped with magnetic sensors and the measurement table 4 is inside a magnetically shielded room. However, for the sake of explanatory convenience, the illustration of such a magnetically shielded room is omitted in FIG. 1.

The information processing device 50 synchronizes and displays the waveform of the magnetic signals obtained through the multiple magnetic sensors and the waveform of the electrical signals obtained through the multiple electrodes on the same time axis. The electrical signals indicate the inter-electrode voltage value obtained for the electrical activity of nerve cells (i.e., the flow of ionic charge caused at the dendrites of neurons during synaptic transmission). Moreover, the magnetic signals indicate minute changes in electric field caused by the electrical activity of the brain. The magnetic field that is generated by the brain is detected by a high-sensitivity superconducting quantum interference device (SQUID). These electrical signals and magnetic signals are examples of biomedical signals.

Figure 2:
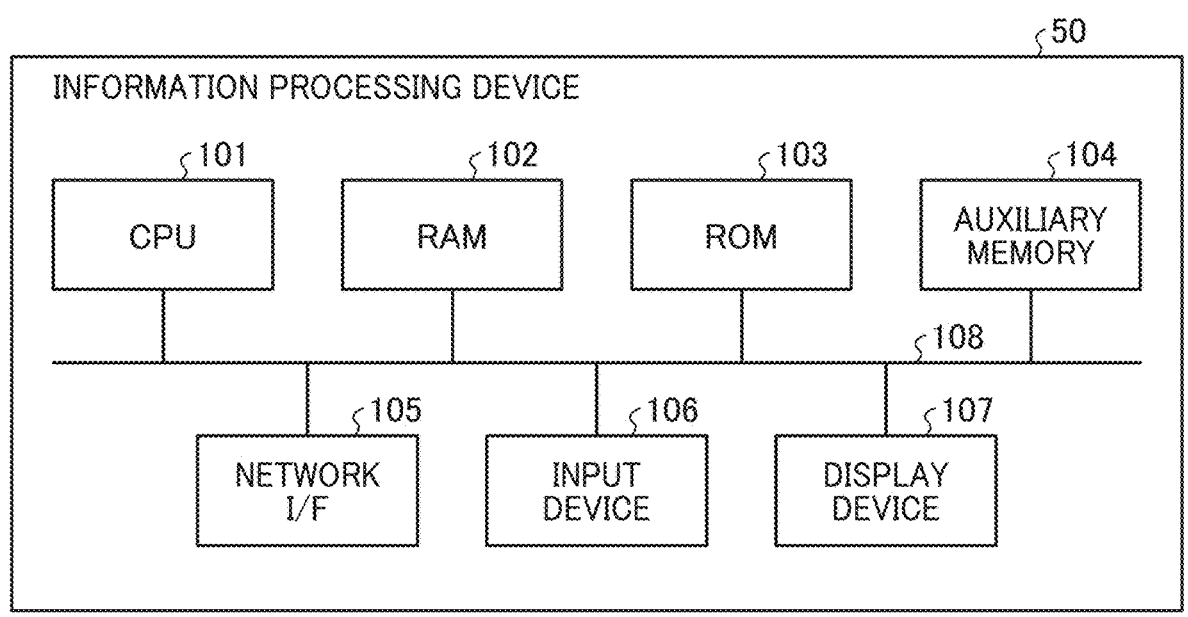
FIG. 2 is a diagram illustrating a hardware configuration of an information processing device according to embodiments of the present disclosure.

FIG. 2 is a diagram illustrating a hardware configuration of the information processing device 50 according to the present embodiment.

A hardware configuration of the information processing device 50 according to the present embodiment is described with reference to FIG. 2.

As illustrated in FIG. 2, the information processing device 50 is provided with a central processing unit (CPU) 101, a random access memory (RAM) 102, a read only memory (ROM) 103, an auxiliary memory 104, a network interface (I/F) 105, an input device 106, and a display device 107, and these elements are interconnected through a bus 108.

The CPU 101 controls the entire operation of the information processing device 50, and performs various kinds of information processing. Moreover, the CPU 101 executes an information displaying program stored in the ROM 103 or the auxiliary memory 104, to control the display of a measurement and collection screen 502 (see, for example, FIG. 5) and the analyzing screen (see, for example, a time-frequency analysis screen 601 in FIG. 11).

The RAM 102 is used as a work area of the CPU 101, and may be a volatile memory in which a desired control parameter or data are stored. The ROM 103 is a nonvolatile memory in which a basic input and output program or the like is stored. For example, the ROM 103 may store the above-described information displaying program.

The auxiliary memory 104 may be, for example, a hard disk drive (HDD) or a solid state drive (SSD). The auxiliary memory 104 stores, for example, a control program to control the operation of the information processing device 50, various kinds of data used to operate the information processing device 50, and files.

The network interface 105 is a communications interface used to communicate with a device such as the server 40 in the network. For example, the network interface 105 is implemented by a network interface card (NIC) that complies with the transmission control protocol (TCP)/Internet protocol (IP).

The input device 106 is, for example, a user interface such as a touch panel, a keyboard, a mouse, and an operation key. The display device 107 is a device for displaying various kinds of information thereon. For example, the display device 107 is implemented by the display function of a touch panel, a liquid crystal display (LCD), or an organic electroluminescence (EL). The measurement and collection screen 502 and the analyzing screen 601 are displayed on the display device 107, and the screen of the display device 107 is updated in response to input and output operation through the input device 106.

The hardware configuration of the information processing device 50 as illustrated in FIG. 2 is given by way of example, and different kinds of devices may further be provided. It is assumed that the information processing device 50 as illustrated in FIG. 2 is configured by hardware such as a personal computer (PC). However, no limitation is intended thereby, and the information processing device 50 may be a mobile device such as a tablet PC. In such a configuration, the network interface 105 is satisfactory as long as it is a communication interface with radio communication capability.

Figure 3:
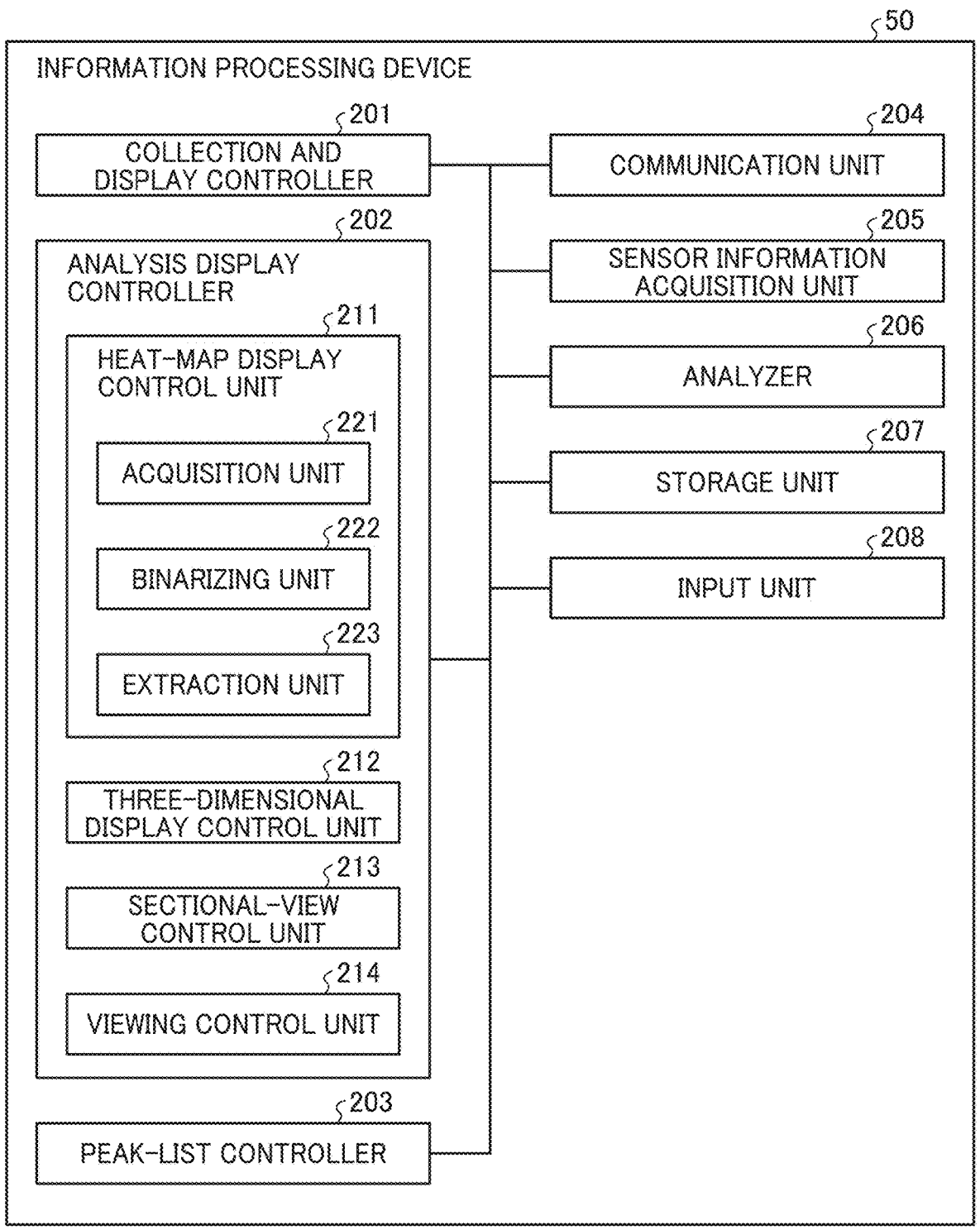
FIG. 3 is a block diagram illustrating a functional configuration of an information processing device according to embodiments of the present disclosure.

FIG. 3 is a block diagram illustrating a functional configuration of the information processing device 50 according to the present embodiment.

As illustrated in FIG. 3, the information processing apparatus 50 includes a collection and display controller 201, an analysis display controller 202, a peak-list controller 203, a communication unit 204, a sensor information acquisition unit 205, an analyzer 206, a storage unit 207, and an input unit 208.

The collection and display controller 201 is a functional unit that controls the visual display when the data output from a sensor is being collected, using methods as will be described below with reference to FIG. 5 to FIG. 10.

Figures 67A, 67B, 67C, 67D:
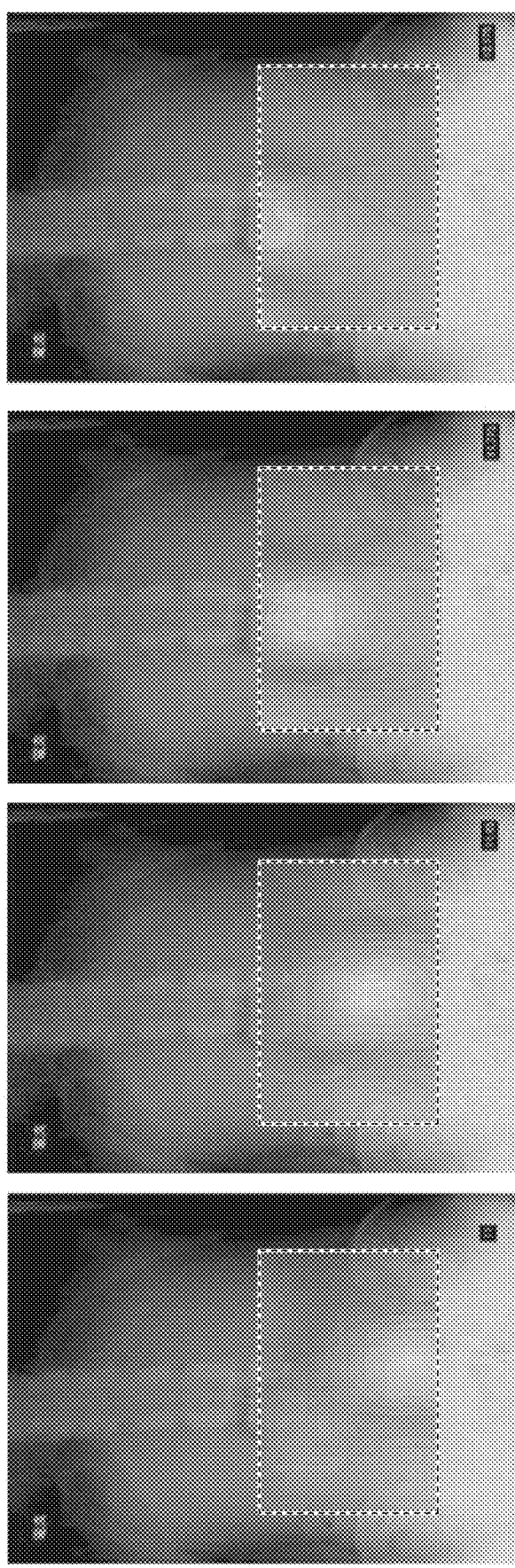
FIG. 67A, FIG. 67B, FIG. 67C, and FIG. 67D are diagrams illustrating how a lumbar signal is transmitted to the upper side in chronological order, according to embodiments of the present disclosure.

The analysis display controller 202 is a functional unit that controls the visual display of, for example, the signal strength of the biomedical signal computed and obtained by the analyzer 206 based on the sensor data (electrical signals or magnetic signals) obtained by the sensor information acquisition unit 205, using methods as will be described below with reference to FIG. 11 to FIG. 67. As illustrated in FIG. 3, the analysis display controller 202 includes a heat-map display control unit 211 (i.e., an example of a display controller), a three-dimensional display control unit 212 (i.e., an example of a display controller), a sectional-view control unit 213 (i.e., an example of a display controller), and a viewing control unit 214.

As will be described later in detail with reference to, for example, FIG. 11, the heat-map display control unit 211 is a functional unit that controls the visual display of the heat map 611 of the time-frequency analysis screen 601. As illustrated in FIG. 3, the heat-map display control unit 211 includes an acquisition unit 221, a binarizing unit 222, and an extraction unit 223.

The acquisition unit 221 is a functional unit that obtains the time and frequency at the position on a heat map 611, as will be described later in detail with reference to, for example, FIG. 11, specified by a user through the input unit 208 and the value of the signal strength of the biomedical signal at the above-specified time and frequency. Each of the above time and frequency specified by the user and the value of the signal strength of the biomedical signal at the specified time and frequency is an example of specific information.

The binarizing unit 222 is a functional unit that determines a threshold based on the value of the signal strength obtained by the acquisition unit 221 and binarizes the image on the heat map 611, which will be described later in detail, based on the determined threshold. In other words, the binarizing unit 222 performs binarization by, for example, setting 0 or 1 to the pixel value of each pixel on the heat map 611 based on a result of the above determination of a threshold.

The extraction unit 223 is a functional unit that extracts, from the binarized image obtained by the binarizing unit 222, an area that includes the pixels at the position indicated by the time and frequency obtained by the acquisition unit 221, where the pixels having the same value (e.g., 1) are combined with each other.

The three-dimensional display control unit 212 is a functional unit that controls the visual display of the three-dimensional view 612 of the time-frequency analysis screen 601. The sectional-view control unit 213 is a functional unit that controls the visual display of the three-view head image 613 on the time-frequency analysis screen 601. The viewing control unit 214 is a functional unit that controls the viewing in accordance with the operation of or input to a replay control panel 615 on the time-frequency analysis screen 601.

The peak-list controller 203 is a functional unit that extracts a peak in signal strength that meets a specified condition and registers the extracted peak in a peak list 614 on the time-frequency analysis screen 601, as will be described later in detail with reference to, for example, FIG. 11.

The communication unit 204 is a functional unit that performs data communication with, for example, the measurement device 3 or the server 40. The communication unit 204 is implemented by the network interface 105 illustrated in FIG. 2.

The sensor information acquisition unit 205 is a functional unit to obtain sensor information (i.e., an electrical signal or magnetic signal) from the measurement device 3 or the server 40 through the communication unit 204. The analyzer 206 is a functional unit that analyzes the sensor data (measured and obtained signal) obtained by the sensor information acquisition unit 205 to compute and obtain a signal that indicates the signal strength at various parts inside the brain (such a signal may also be referred to as a biomedical signal in the following description).

The storage unit 207 is a functional unit that stores, for example, the data of a biomedical signal that indicates the signal strength computed and obtained by the analyzer 206. The storage unit 207 is implemented by the RAM 102 or the auxiliary memory 104 as illustrated in FIG. 2.

The input unit 208 is a functional unit that accepts an input operation of annotation to be added to the sensor information and various kinds of input operations for the time-frequency analysis screen 601. The input unit 208 is implemented by the input device 106 as illustrated in FIG. 2.

The collection and display controller 201, the analysis display controller 202, the peak-list controller 203, the sensor information acquisition unit 205, and the analyzer 206 as described above may be implemented as the CPU 101 launches a program stored in a memory such as the ROM 103 into the RAM 102 and executes the program. Note also that some of or all of the collection and display controller 201, the analysis display controller 202, the peak-list controller 203, the sensor information acquisition unit 205, and the analyzer 206 may be implemented by hardware circuitry such as a field-programmable gate array (FPGA) or an application specific integrated circuit (ASIC), in place of a software program.

The functional units as illustrated in FIG. 3 merely indicate functions schematically, and no limitation is intended by such configurations. For example, a plurality of functional units that are illustrated as independent functional units in FIG. 3 may be configured as a single functional unit. Alternatively, the function of a single functional unit as illustrated in FIG. 3 may be divided into a plurality of functions implemented by a plurality of functional units.

Figure 4:
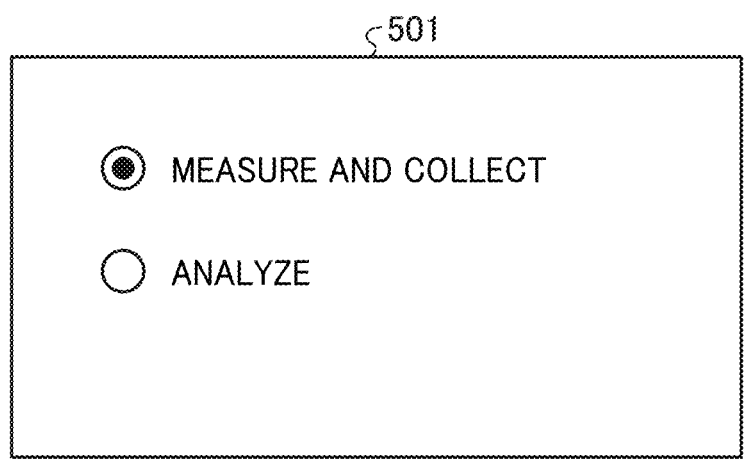
FIG. 4 is a diagram illustrating a starting screen displayed on an information processing device, according to embodiments of the present disclosure.

FIG. 4 is a diagram illustrating a starting screen displayed on the information processing device 50, according to the present embodiment. The operations on the starting screen 501 are described below with reference to FIG. 4.

On the starting screen 501, selection keys "measurement and collection" and "analysis" are displayed. When the brain wave and brain magnetism are to be measured, in many cases, the person who measures and collects the data and the person who analyzes the data are different. For example, when the "measurement and collection" key is selected by a measurement engineer (technician), the data measured by the measurement device 3 is sequentially stored on the server 40, and is read and displayed by the information processing device 50. On the other hand, when the "analysis" key is selected by a doctor after the measurement and collection is done, the recorded measurement data is read and analyzed.

Figure 5:
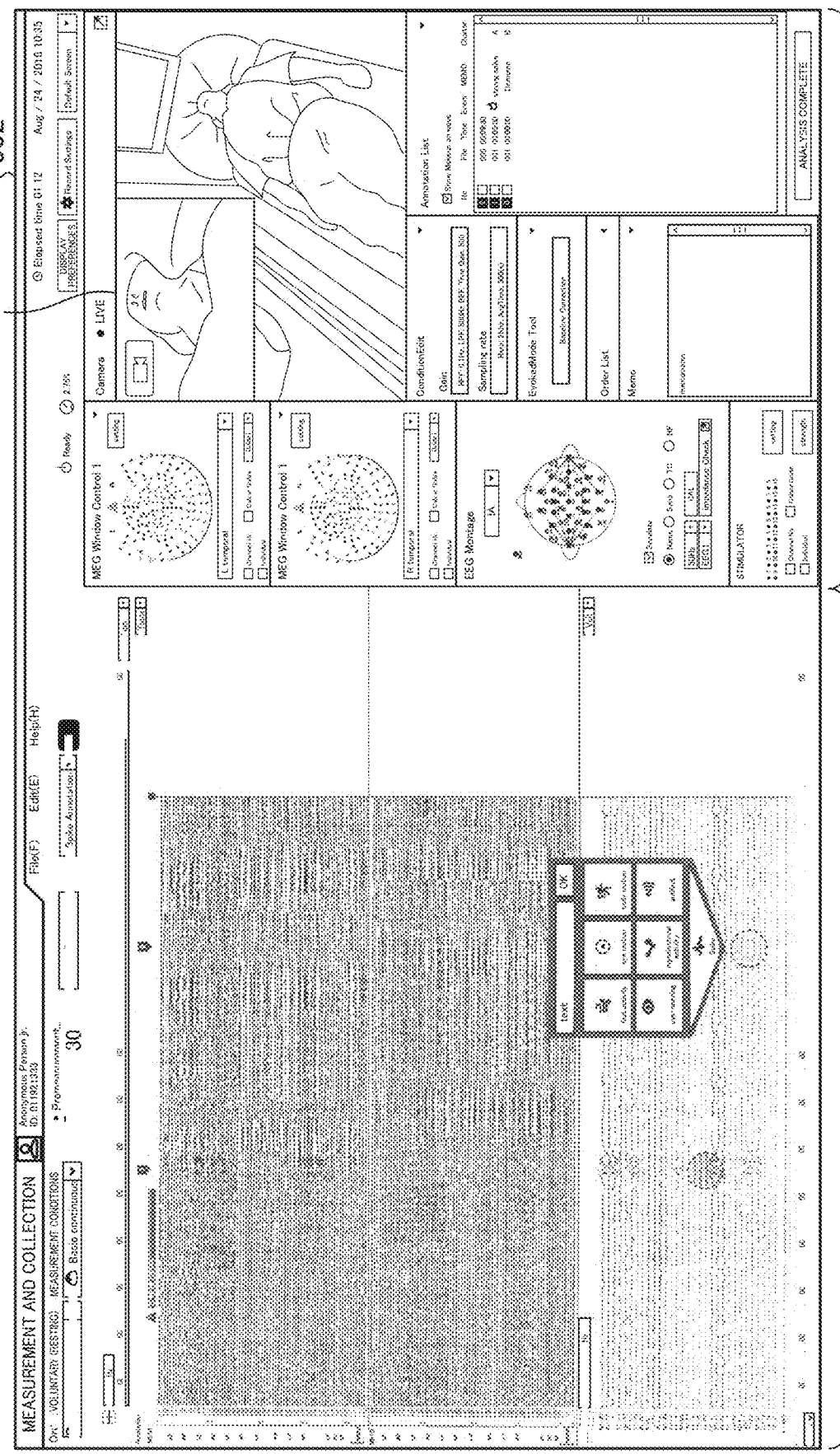
FIG. 5 is a diagram illustrating a measurement and collection screen according to embodiments of the present disclosure.

FIG. 5 is a diagram illustrating a measurement and collection screen 502 according to the present embodiment.

As illustrated in FIG. 5, a measurement and collection screen 502 includes an area 511a on which the signal waveforms of measured biomedical signals (i.e., magnetic signals and electrical signals in the present embodiment) are displayed, and an area 511b on which monitoring data other than the signal waveform is displayed. The area 511a on which signal waveform is displayed is arranged on the left side of the screen when viewed from the technician, and the area 511B on which monitoring data other than the signal waveform is displayed is arranged on the right side of the screen when viewed from the technician. Accordingly, there is an economy of motion between the movement of the mouse from the area 511a on the left side of the screen to the area 511b on the right side of the screen and the motion of the line of sight of a technician that follows the movement of a waveform (detected in real time and dynamically displayed from the left side of the screen to the right side of the screen), thereby providing improved efficiency.

In the area 511B of the display screen, a monitoring window 512 is displayed to monitor the state of a subject during measurement. By displaying the live image of the subject while he/she is being measured, the reliability of the check and judgment of a signal waveform can be improved as will be described later in detail. Note that FIG. 5 illustrates a case in which the entirety of the measurement and collection screen 502 is displayed on the display screen of a single monitoring display (i.e., the display device 107). However, no limitation is indicated thereby, and the area 511a on the left side of the screen and the area 511b on the right side of the screen may separately be displayed by two or more monitoring displays.

Figure 6:
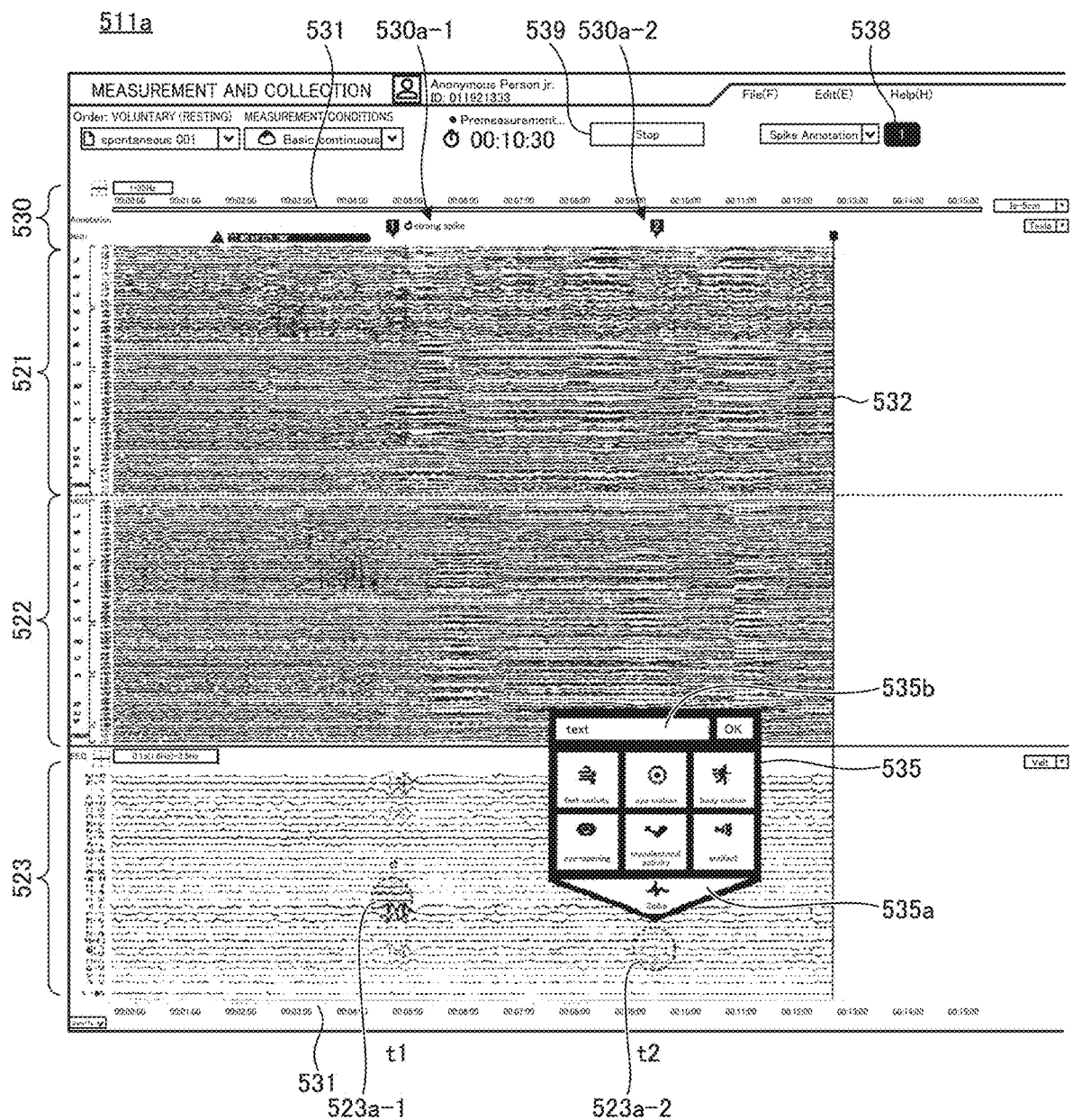
FIG. 6 is a diagram illustrating a magnified view of an area of a measurement and collection screen on the left side, according to embodiments of the present disclosure.

FIG. 6 is a diagram illustrating a magnified view of an area of the measurement and collection screen 502 on the left side, according to the present embodiment.

The area 511a includes a first display area 530 in which the time data of signal detection is displayed in the horizontal direction of the screen, and second display areas 521 to 523 in which a plurality of signal waveforms based on the signal detection are displayed in parallel across the screen.

In the example as illustrated in FIG. 6, the time data that is displayed in the first display area 530 is a time line including the time indication given along a time axis 531. However, no limitation is indicated thereby, and such a time line may only be a band-like or belt-like axis where no time (time in numbers) is displayed, or may only be the time (time in numbers) where no axis is given. Alternatively, a one time line may be displayed by displaying the time axis 531 under the second display area 523 in addition to the first display area 530 on the topside of the screen.

In the area 511a, a plurality of signal waveforms obtained by a plurality of similar kinds of sensors or various kinds of signal waveforms obtained by a group of a plurality of different kinds of sensors are displayed in a synchronous manner along the same time axis 531. In the example as illustrated in FIG. 6, the waveforms of a plurality of magneto-encephalography (MEG) signals obtained from the right side of the head of a subject and the waveforms of a plurality of magneto-encephalography (MEG) signals obtained from the left side of the head of a subject are displayed parallel to each other in the second display area 521 and the second display area 522, respectively. In the second display area 523, the waveforms of a plurality of electro-encephalography (EEG) signals are displayed in parallel. These waveforms of a plurality of electro-encephalography (EEG) signals correspond to the voltage signals measured between pairs of electrodes. Each of these waveforms of a plurality of signals is displayed in association with the identification number or channel number of the sensor through which the signal is obtained.

Once measurement is started and the readings from each sensor are collected, as time passes a signal waveform is displayed moving from left to right in each of the second display areas 521 to 523 in the area 511a. A vertical line 532 indicates the measurement time (present time), and moves from the left side to the right side of the screen. Once the signal waveform display reaches the right end of the area 511a (i.e., until the right end of the time axis 531), the signal waveform gradually disappears from the left end of the screen to the right. Then, new signal waveforms are displayed at disappearing positions in sequence from the left side to the right side, and the line 532 also moves from the left end of the screen to the right. Together with the above changes on the display, the lapse of time is also displayed in the horizontal first display area 530 along the time axis 531 as the measurement progresses. The measurement and collection continues until the stop key 539 is touched or clicked.

In the present embodiment, when the technician (i.e., a person who collects the data) notices, for example, irregularities in waveform and a singular point of amplitude on the signal waveform during the data recording, he/she can mark a problematic point or area on the signal waveform. The point or area of such a problematic point or area to be marked can be specified by moving a mouse cursor or clicking with a mouse. The specified point or area is highlighted on the signal waveforms of the second display areas 521 to 523, and the specified result is displayed along the time axis 531 of the first display area 530 in a relevant point in time or time range. The marking information including the display along the time axis 531 is stored together with the signal waveform data. The specified point corresponds to particular time, and the specified area corresponds to a certain area including the particular time.

In the example illustrated in FIG. 6, an area including at least one channel is specified at a time t1 in the second display area 523, and the span of time including the time t1 is highlighted at the mark 523a-1. In association with the display of the mark 523a-1, an annotation 530a-1 that indicates the result of specification is displayed at the corresponding point in time in the first display area 530. At a time t2, another point in waveform or an area around that point is marked in the second display area 523, and a mark 523a-2 is highlighted at that point (the time t2) or in the area around that point (the time t2) (where at least one of a time range or a plurality of waveforms is indicated). At the same time, an annotation 530a-2 is displayed at the corresponding point in time (time range) in the first display area 530. Note that the term "annotation" indicates that related information is given to certain data as an annotation. An annotation according to the present embodiment is displayed at least based on the specified time data in association with the position at which the waveform is displayed based on the time data. When a plurality of channels are, the annotation according to the present embodiment displayed in association with the corresponding channel information.

The annotation 530a-1 that is added to the first display area 530 at the time t1 includes, for example, an annotation identification number and the waveform-attribute information. In the present embodiment, an icon that indicates the attributes of the waveform and the text data saying "strong spike" are displayed together with the annotation number "1."

Once the technician specifies another point in waveform or an area around that point in waveform at the time t2, the mark 523a-2 is highlighted at the specified point, and an annotation number "2" is displayed at the corresponding point in time in the first display area 530. Further, a pop-up window 535 for selecting the attribute is displayed at the highlighted point. The pop-up window 535 includes selection keys 535a for selecting the various kinds of attribute, and an input box 535b through which a comment or additional information is input. On the selection keys 535a, the causes of irregularities in waveform such as fast activity, eye motion, body motion, and spike are indicated as the attributes of waveform. As the technician can check the state of the subject through the monitoring window 512 of the area 511b in the screen, he/she can appropriately select the attribute indicating the causes of irregularities in waveform. For example, when a spike occurs in a waveform, the technician can determine whether such a spike shows symptoms of epilepsy or caused by the body motion (such as a sneeze) of the subject.

The same operations are also performed at the time t1. In FIG. 6, as the selection key 535a of "spike" is selected in the pop-up window 535 and "strong spike" is input to the input box 535b, the annotation 530a-1 is displayed in the first display area 530. Due to such a display mode, when a large number of signal waveforms are displayed along the same time axis 531 in a synchronous manner, a point of interest or region of interest of the signal waveforms can visually be recognized and identified easily, and the basic information at a point of interest can easily be figured out.

Some of or all of the annotation 530a-1, for example, at least one of an attribute icon and a text data may be displayed in the proximity of the mark 523a-1 on the signal waveforms in the second display area 523. When such an annotation is added directly over the signal waveforms, the ability to check the shape of the waveforms may be impaired. For this reason, when an annotation is displayed over the signal waveforms in the second display areas 521 to 523, it is desired that display or non-display of such an annotation be selectable.

The counter box 538 displays the cumulative number of spike annotations. In the present embodiment, every time "spike" is selected, the counter value in the counter box 538 is incremented. Accordingly, the analyst can instantly figure out the total number of spikes selected until now (as indicated by a line 532) since the recording has started.

Figure 7:
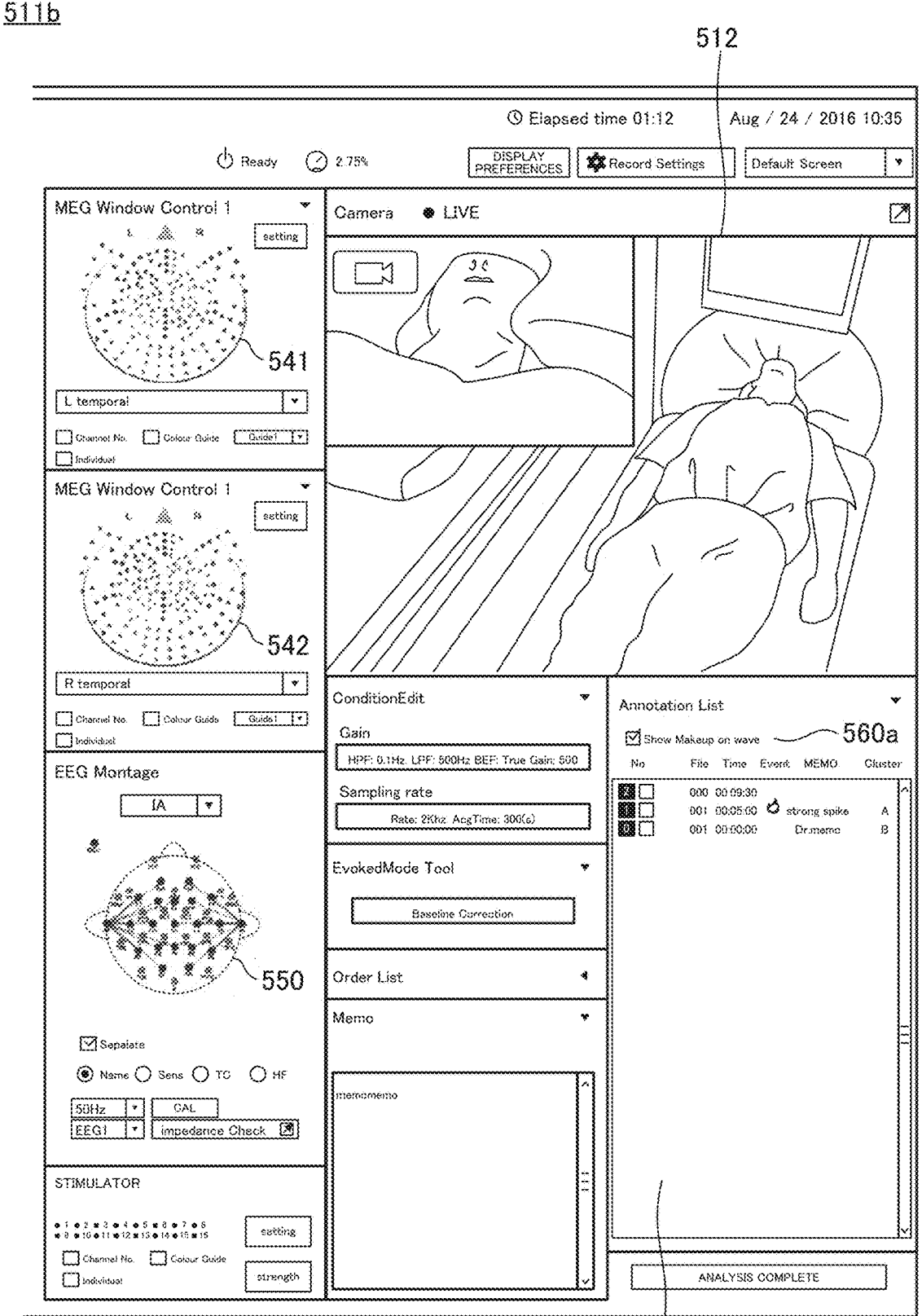
FIG. 7 is a diagram illustrating a magnified view of an area of a measurement and collection screen on the right side, according to embodiments of the present disclosure.

FIG. 7 is a diagram illustrating a magnified view of an area of the measurement and collection screen 502 on the right side, according to the present embodiment.

In FIG. 7, a state at the same time as illustrated in FIG. 6 (the point in time indicated by the line 532) is illustrated. In the monitoring window 512 of the area 511b, the live image of a state in which a subject lies on the measurement table 4 and the head of the subject is inside the measurement device 3 is displayed. In the area 511b, the magnetoencephalogram distribution maps 541 and 542, the brain-wave distribution map 550, and the annotation list 560, each of which corresponds to one of the signal waveforms in the second display areas 521, 522, and 523, are displayed. The annotation list 560 is a list of annotations of the signal waveforms as illustrated in FIG. 6. Every time the point or area on the signal waveforms is specified in the second display areas 521 to 523 and annotated, the associated information is sequentially added to the annotation list 560.

When information is added to the annotation list 560 on the measurement and collection screen 502, such information is displayed, for example, in descending order where new data is displayed on an upper side). However, no limitation is intended thereby. For example, the annotation list 560 may be displayed in ascending order. The annotation list 560 is displayed such that the relation with the annotation displayed in the first display area 530 along the time axis 531 will be clear to the analyst. Alternatively, the display order may be changed, or information may be sorted according to the type of item.

In the example as illustrated in FIG. 7, the time data that correspond to the annotation number "1" and the added annotation are listed in the annotation list 560. As the annotation, an attribute icon that indicates "spike" and the text saying "strong spike" are recorded. When the mark 523a-1 is highlighted, the time data that correspond to the annotation number "2" is listed. In the present embodiment, the term "annotation" may be considered to be a group of information including an annotation number, time data, and annotation, or may be considered to be only the annotation. Additionally, the term "annotation" may be considered to be a group of information including annotation and an annotation number or time data.

A selection box 560a to choose show/hide is arranged near the annotation list 560. When "hide" is selected in the selection box 560a, the annotation other than a highlighting mark on the signal waveforms is hidden from view in the second display areas 521 to 523. However, the display of the annotation in the first display area 530 along the time axis 531 is maintained. Due to such a configuration, the annotation becomes recognizable without impairing the recognizability of signal waveforms.

Figure 8:
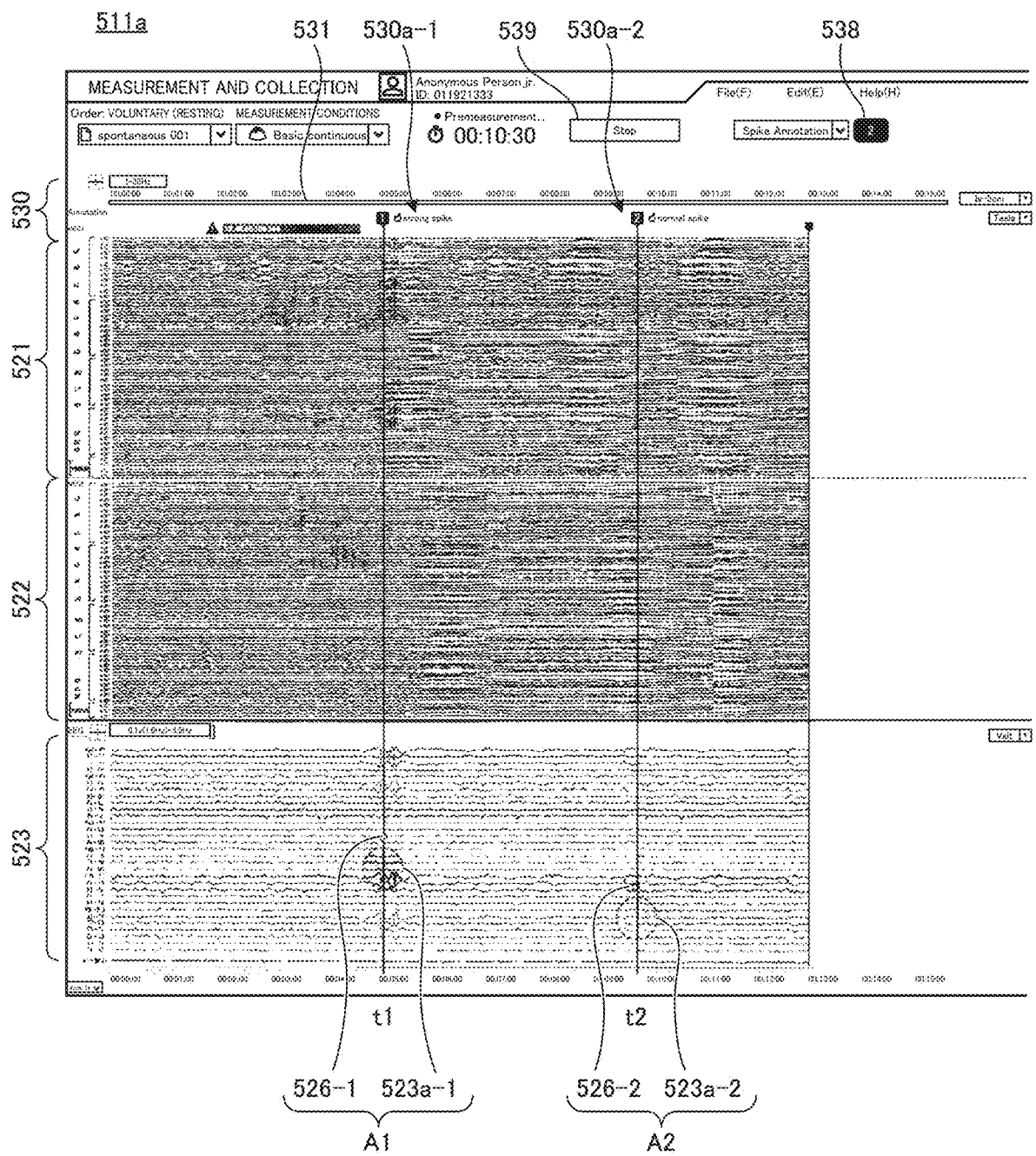
FIG. 8 is a diagram illustrating a state immediately after an annotation is input, according to embodiments of the present disclosure.

FIG. 8 is a diagram illustrating a state immediately after an annotation is input, according to the present embodiment.

More specifically, FIG. 8 illustrates a screen displayed immediately after "spike" is selected from the pop-up window 535 at the time t2 and a text "normal spike" is input. When "OK" key is selected from the pop-up window 535 as illustrated in FIG. 6, the pop-up window 535 closes and an annotation 530a-2 is displayed at the corresponding point in time in the first display area 530 as illustrated in FIG. 8. In association with the annotation number "2," an attribute icon that indicates "spike" and text data saying "normal spike" are displayed. At the same time, the value in the counter box 538 is incremented. Moreover, an attribute icon 526-2 is displayed near the highlighted mark 523a-2. In the present embodiment, the attribute icon 526-1 is also displayed near the mark 523a-1. However, as described above, the attribute icons 526-1 and 526-2 may be displayed or hidden in a selective manner. The annotation includes annotation A1 including the mark 523a-1 and the attribute icon 526-1 and annotation A2 including the mark 523a-2 and the attribute icon 526-2.

FIG. 9 is a diagram illustrating an updated annotation list according to the present embodiment.

The annotation list 560 is updated as the annotation that corresponds to the mark 523a-2 is added to the area 511a on the left side of the measurement and collection screen 502. As a result, a memo saying "normal spike" is added to the annotation number "2."

Every time a desired point or area on the signal waveforms is specified in the area 511a during the measurement, the specified point is highlighted, and the annotation is displayed in the first display area 530 along the time axis 531. In the area 511b, the annotation is sequentially added to the annotation list 560.

It is not always necessary to display an annotation number in the annotation list 560 and the area 511a where signal waveforms are displayed, and the display of an annotation number may be omitted. Any information can be used as identification information as long as the added annotation can be recognized by that information. For example, an attribute icon, attribute texts (e.g., "strong spike"), and time in the proximity of the time axis 531 may be displayed in association with each other. Further, a file number (i.e., the number displayed in the item "File" as illustrated in FIG. 9) may be displayed along with the area 511a.

When the stop key 539 (see FIG. 8) is selected (touched or clicked) and the measurement is terminated, the highlighted portion specified in the second display areas 521 to 523 is stored in association with the signal waveform. The annotation that is displayed at the corresponding point in time in the first display area 530 is also stored in association with the annotation number and the time. Relevant information such as the counter value in the counter box 538 and the items in the annotation list 560 is also stored. By storing the above display information, even if the technician and the analyst are different, the analyst can easily recognize and analyze a problematic portion.

Figure 10:
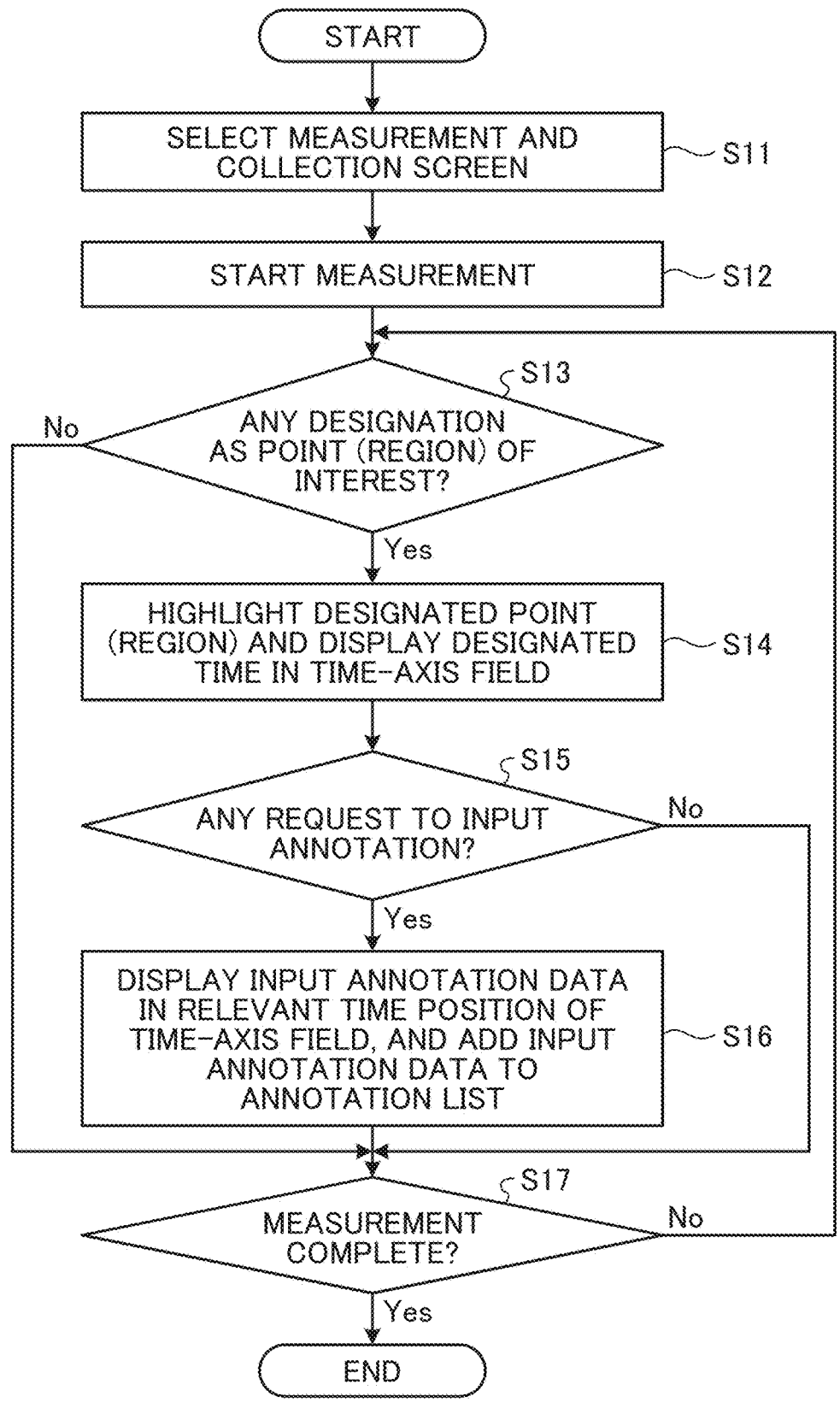
FIG. 10 is a flowchart of the measurement and collection processes performed by an information processing device, according to embodiments of the present disclosure.

FIG. 10 is a flowchart of the measurement and collection processes performed by the information processing device 50, according to the present embodiment.

The measurement and collection that is performed by the information processing device 50 according to the present embodiment below with reference to FIG. 10.

When "measurement and collection" is selected on the starting screen 501 as illustrated in FIG. 4 (step S11), the measurement is started, and the display is controlled in a synchronous manner along a time axis where the waveforms of a plurality of signals are equivalent to each other (step S12). In the present embodiment, the term "a plurality of signal waveforms" includes both the signal waveform detected by a plurality of sensors of the same kind and the multiple signal waveforms detected by a plurality of various kinds of sensors. In the present embodiment, the waveforms of biomedical signals consist of the waveform of the magnetic signals obtained through a plurality of magnetic sensors from the right side of the head of a subject, the waveform of the magnetic signals obtained through a plurality of magnetic sensors from the left side of the head of the subject, and the waveform of the electric signals obtained through electrodes for measuring the electrical brain waves of the subject. However, no limitation is intended thereby. The sensors may be selected not just between the right and left groups of sensors, but may be selected from any part of the brain such as a parietal region, a frontal lobe, and a temporal lobe. When sensors at a parietal region are selected in "MEG Window Control 1" as illustrated in, for example, FIG. 7, the sensors other than sensors at a parietal region are selected in "MEG Window Control 2."

The information processing device 50 determines whether any designation is made as a point of interest or region of interest in the displayed signal waveform (step S13). When such designation is made as a point of interest or a range of interest (YES in the step S13), the display is controlled to highlight the designated point in the display areas of signal waveform (i.e., the second display areas 521 to 523), and to display the results of selection in a relevant point in time of the time-axis field (i.e., the first display area 530) (step S14). The result of designation includes data indicating that the designation has been made or the identification information of the designation. Then, whether or not there is a request to input an annotation is determined at the same time as when the results of designation are displayed in the time-axis field or before or after the results of designation are displayed in the time-axis field (step S15). When there is a request to input an annotation (YES in the step S15), the input annotation is displayed in a relevant point in time of the time-axis field, and the input annotation is added to the annotation list so as to be displayed therein (step S16). Then, whether or not a measurement termination command has been input is determined (step S17). On the other hand, when no point of interest or range of interest is designated (NO in the step S13) and when there is no request to input an annotation (NO in the step S15), the process proceeds to a step S17, and whether or not the measurement is completed is determined. Steps S13 to S16 are repeated until the measurement is completed (YES in the S17).

Due to the above information displaying method, the measurement and collection screen 502 can be provided in which the visibility of the signal data is high when signals are collected from a plurality of sensors.

Figure 11:
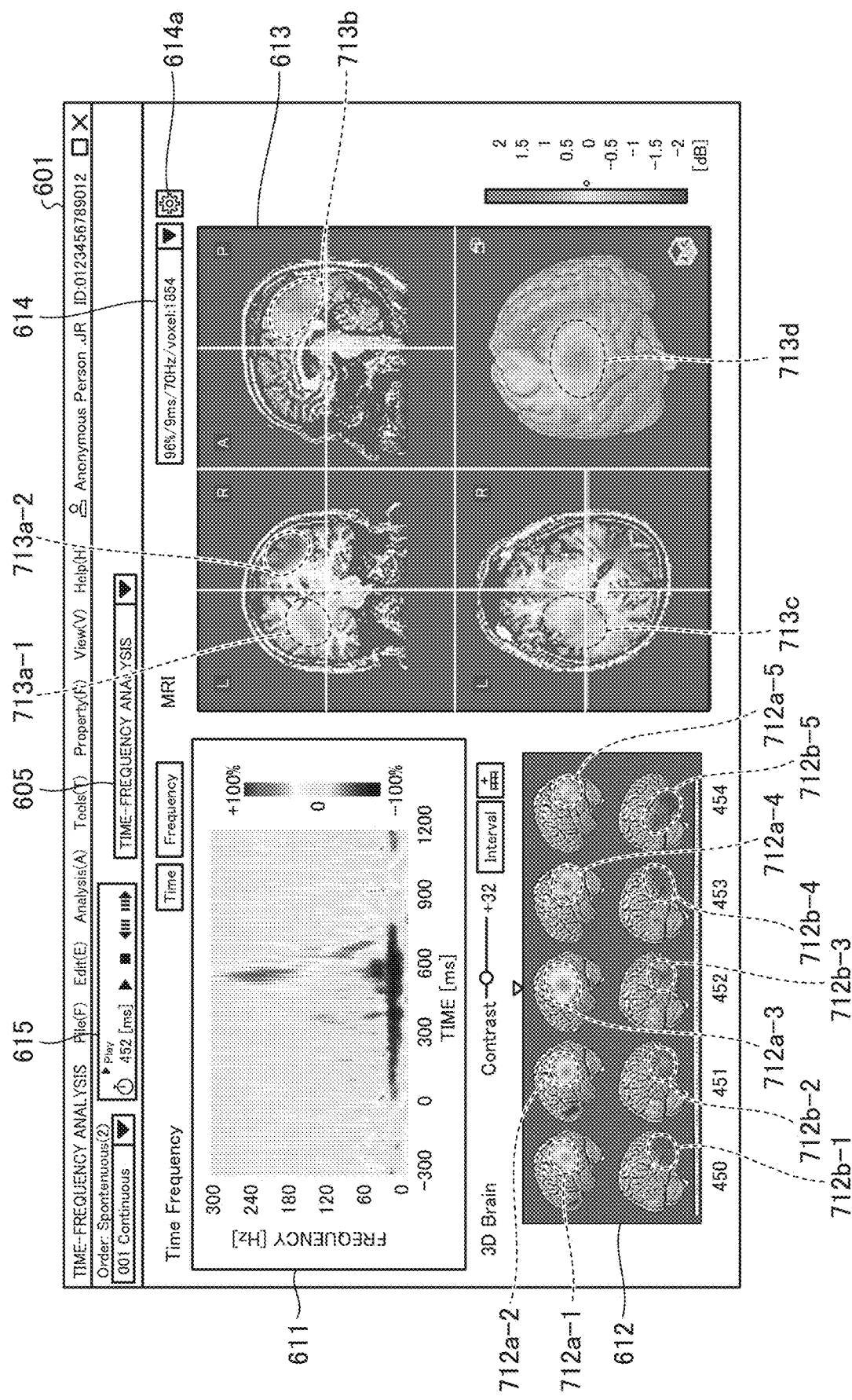
FIG. 11 is a diagram illustrating a time-frequency analysis screen according to embodiments of the present disclosure.

FIG. 11 is a diagram illustrating a time-frequency analysis screen 601 according to the present embodiment.

The analyzing operations that are performed on the time-frequency analysis screen 601, which is displayed on the information processing device 50, are described below with reference to FIG. 11.

When an "analysis" key is touched or clicked on the starting screen 501 as described above with reference to FIG. 4, the analyzer 206 analyzes the sensor information (i.e., an electrical signal or magnetic signal) that is collected by the above measurement and collection processes that are performed on the measurement and collection screen 502, and computes and obtains a biomedical signal that indicates the signal strength at varying points inside the brain (an example of a biological site or a source). As a method of calculating the signal strength, for example, spatial filtering is known in the art. However, no limitation is indicated thereby, and any other method may be adopted. When an "analysis" key is selected on the starting screen 501 as described above with reference to FIG. 4, the analysis display controller 202 controls the display device 107 to display the time-frequency analysis screen 601 as illustrated in FIG. 11. As illustrated in FIG. 11, an analyzing screen switching list 605, a heat map 611, a three-dimensional view 612, a three-view head image 613, a peak list 614, and a replay control panel 615 are displayed the time-frequency analysis screen 601. An object of the analysis and measurement that is performed using the time-frequency analysis screen 601 is to mark and display critical sites of the brain for human to live, such as a visual area, auditory area, somatosensory area, motor area, and a language area. A peak-list setting key 614a that is displayed on the right side of the peak list 614 is used to display a window to configure the conditions for a peak to be registered in the peak list 614. How the conditions for a peak to be registered in the peak list 614 are configured by touching or clicking the peak-list setting key 614a will be described later in detail. The display and operation of the heat map 611, the three-dimensional view 612, the three-view head image 613, the peak list 614, and the replay control panel 615 will be described later in detail.

The analyzing screen switching list 605 is used to make a selection from among various kinds of analyzing screens. In addition to or in place of the time-frequency analysis screen 601 according to the present embodiment where analysis is performed in regard to time and frequency based on a biomedical signal, the analyzing screens selectable from the analyzing screen switching list 605 may include, for example, an analyzing screen where dipole estimation is performed to estimate or analyze a site indicative of epilepsy or the like based on a biomedical signal. In the present embodiment, analyzing operations on the time-frequency analysis screen 601 are described.

Some operations to be made on the heat map 611 of the time-frequency analysis screen 601 are described with reference to FIG. 12 to FIG. 15.

Figure 12:
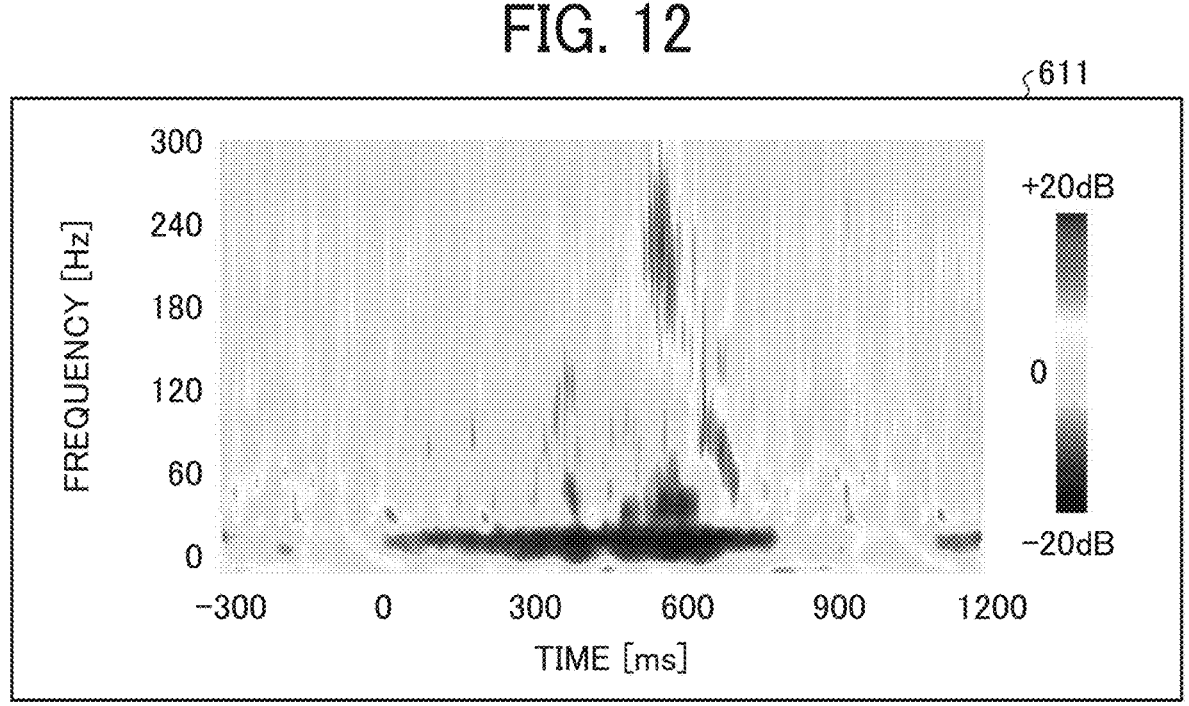
FIG. 12 is a diagram illustrating a heat map in which the range is expressed in decibels, according to embodiments of the present disclosure.

FIG. 12 is a diagram illustrating the heat map 611 in which the range is expressed in decibel, according to the present embodiment.

Figure 13:
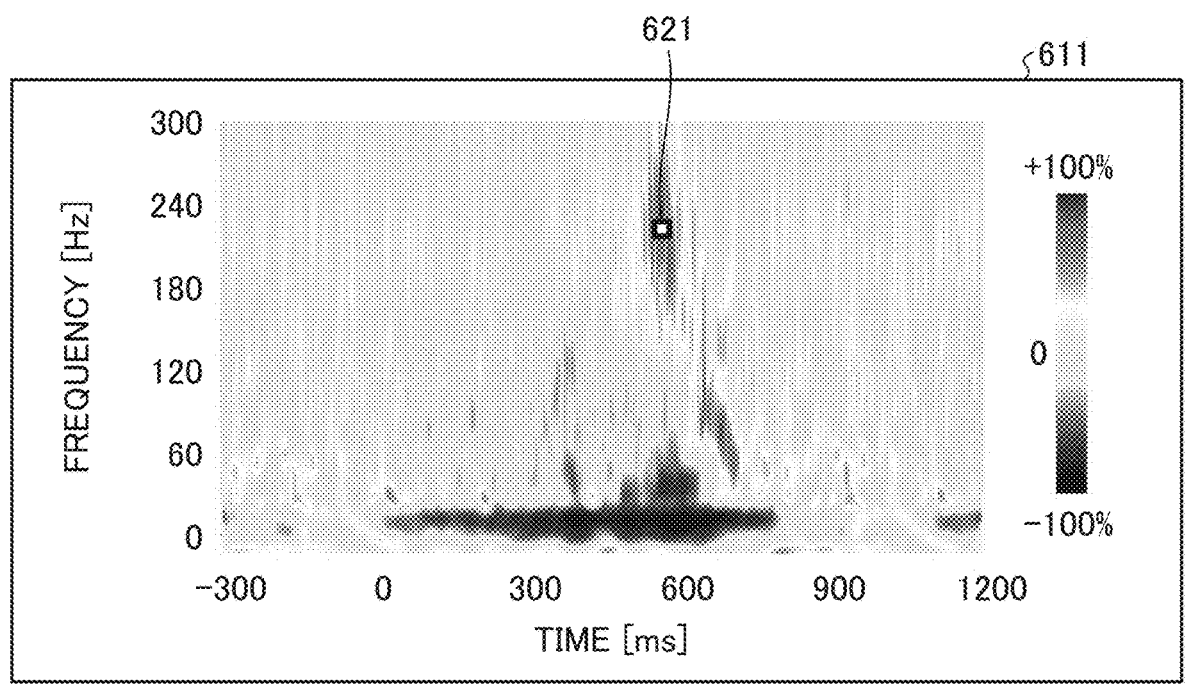
FIG. 13 is a diagram illustrating a state where a specific position is designated on a heat map, according to embodiments of the present disclosure.

FIG. 13 is a diagram illustrating a state where a specific position is designated on a heat map, according to the present embodiment.

Figure 14:
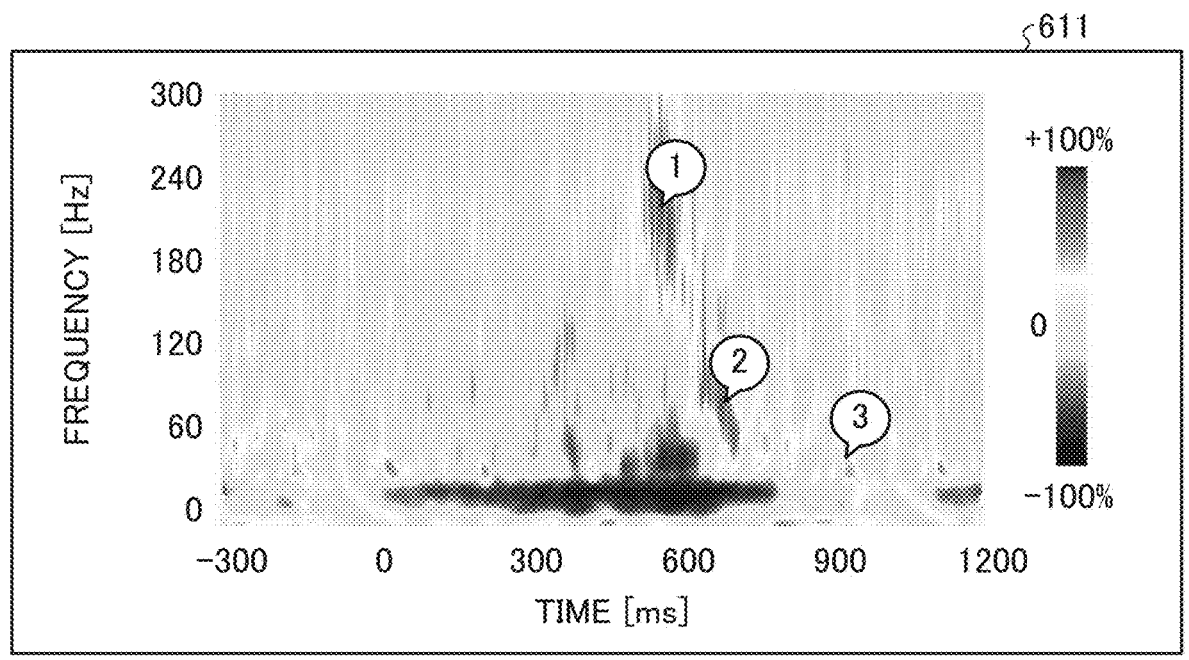
FIG. 14 is a diagram illustrating a state where three peaks are indicated on a heat map from a peak list, according to embodiments of the present disclosure.

FIG. 14 is a diagram illustrating a state where three peaks are indicated on a heat map from a peak list, according to the present embodiment.

Figure 15:
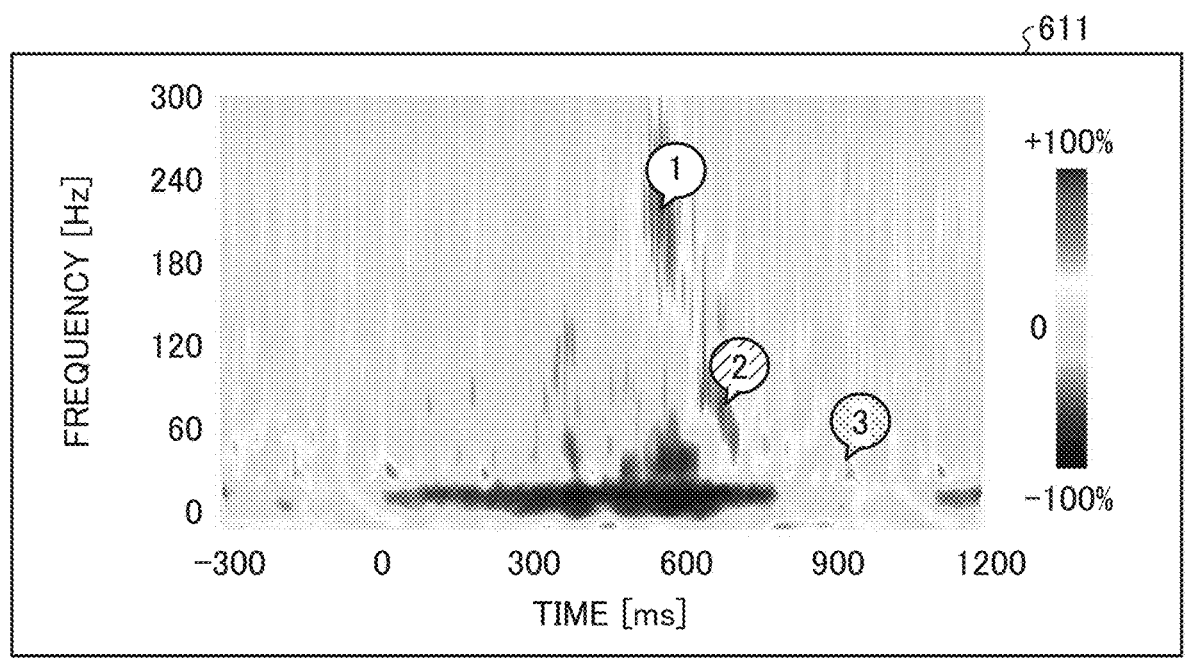
FIG. 15 is a diagram illustrating a state where the display mode of each peak is changed on a heat map according to the data of each peak, according to embodiments of the present disclosure.

FIG. 15 is a diagram illustrating a state where the display mode of each peak is changed on a heat map according to the data of each peak, according to the present embodiment.

Time-frequency decomposition is performed on the biomedical signals computed and obtained by the analyzer 206, each of which indicates the signal strength at a position inside the brain, and as illustrated in FIG. 11, the heat map 611 is an figure in which the horizontal axis and the vertical axis indicate the time (i.e., the time elapsed since a triggering time) and the frequency, respectively, and the two-dimensional distribution (first intensity distribution) of the signal strength of the biomedical signals, which is specified by the time and frequency, is expressed by color. In other words, on the heat map 611, colors are indicated on a pixel-by-pixel basis by pixel values indicative of colors (for example, red, green, and blue (RGB)) that indicate the differences in signal strength. However, each pixel is substantially associated with the signal strength of the biomedical signal. In the example as illustrated in FIG. 11, the signal strength is indicated by the variations with reference to, for example, a prescribed reference value. In the present embodiment, a prescribed reference value is, for example, 0% as the average of the signal strength when no stimulus is given to a test subject.

In the present embodiment, illustration is made based on the premise that the average of the signal strength varies between 0±100%. However, no limitation is intended thereby. When the average of the signal strength varies beyond 1000%, the range in the illustration may be changed to, for example, 200%. Alternatively, for example, decibels (dB) may be adopted in place of the percentage (%) as in the heat map 611 as illustrated in FIG. 12, which is a diagram illustrating a heat map in which the range is expressed in decibels, according to embodiments of the present disclosure. For example, when some sort of stimulation is given to the test subject (for example, physical shock is given to the test subject, an arm of the test subject is moved, the test subject is made to listen to some spoken words, or the test subject is made to listen to a sound) at time 0 millisecond (ms), the heat map 611 indicates, at the later time, the state of activity of the brain after that stimulation is given to the test subject, and indicates, at the time earlier than the time 0 ms, the state of activity of the brain before that stimulation is given to the test subject.

The display operation on the heat map 611 is controlled by the heat-map display control unit 211.

As illustrated in FIG. 13, a desired position (point) on the heat map 611 can be specified as the analyst performs an operation or input (clicking or tapping operation) to the input unit 208. As illustrated in FIG. 13, for example, the heat-map display control unit 211 controls the display to display the specified position like the specified point 621. In FIG. 13, the specified point 621 is indicated by a white-colored rectangle. However, no limitation is intended thereby, and the specified point 621 may be indicated in any other display modes.

On the heat map 611 as illustrated in FIG. 13, the position specified by the operation of or input to the input unit 208 is indicated. However, no limitation is indicated thereby, and the heat map and some peak positions at the time and frequency that the item of peak data selected from among the peaks registered in the peak list 614 indicates may be displayed. For example, the top N peak positions with reference to the peak selected from the peak list 614 may be displayed on the heat map 611. FIG. 14 is a diagram illustrating an example in which the positions of the top three peaks are indicated, according to the present embodiment. How the peak positions are to be indicated may be determined based on the settings. For example, in addition to or in place of the above setting, the settings may be switched between the setting in which no peak is to be indicated or the setting in which peaks whose signal strength is equal to or higher than M are indicated.

As illustrated in FIG. 15, the display mode of the multiple peaks displayed on the heat map 611 may be changed according to the attribute information of those peaks. FIG. 15 is a diagram illustrating an example in which a number is given to each of the indicated peaks and the colors of each portion in which a number is indicated are changed so as to be different from each other, according to the present embodiment.

When a particular position is specified on the heat map 611 as described above, the distribution of the signal strength of the biomedical signals of the time and frequency corresponding to the specified position is displayed as a heat map (second heat map). Note that this heat map (second heat map) is different from the heat map on the heat map 611. As illustrated in FIG. 11, for example, the distribution of the signal strength of the biomedical signals of the time and frequency corresponding to the specified position is displayed like sites 712*a*-1 to 712*a*-5 and 712*b*-1 to 712*b*-5 on the images of the brain in the three-dimensional view 612 (i.e., an example of an image indicative of a source), and the distribution of the signal strength of the biomedical signals of the time and frequency corresponding to the specified position is displayed like the sites 713*a*-1, 713*a*-2, 713*b*, 713*c*, and 713*d* on the images of the brain in the three-view head image 613 (i.e., an example of an image indicative of a source). More specifically, the distribution of the signal strength of the biomedical signals of the time and frequency corresponding to the position specified on the heat map 611 is displayed as a red-to-blue heat map.

How an area or region is specified on a heat map is described below with reference to FIG. 16 to FIG. 25.

Figure 16:
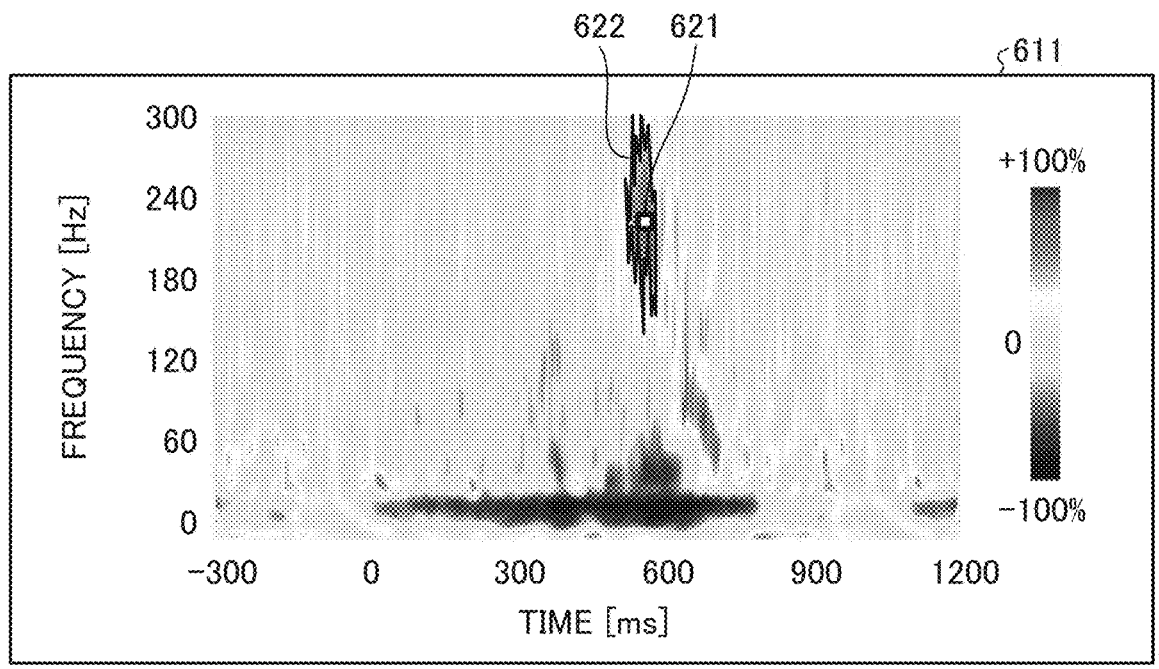
FIG. 16 is a diagram illustrating a state where a specific area is designated on a heat map, according to embodiments of the present disclosure.

FIG. 16 is a diagram illustrating a state where a specific area is designated on a heat map, according to the present embodiment.

Figure 17:
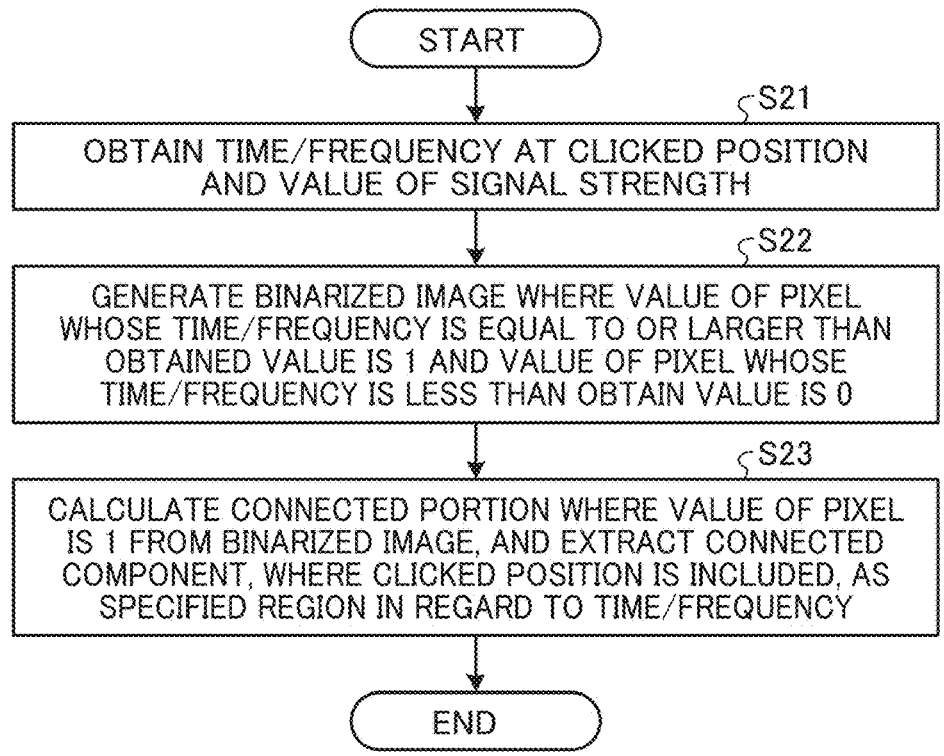
FIG. 17 is a flowchart of region specifying processes according to embodiments of the present disclosure.
Figure 18:
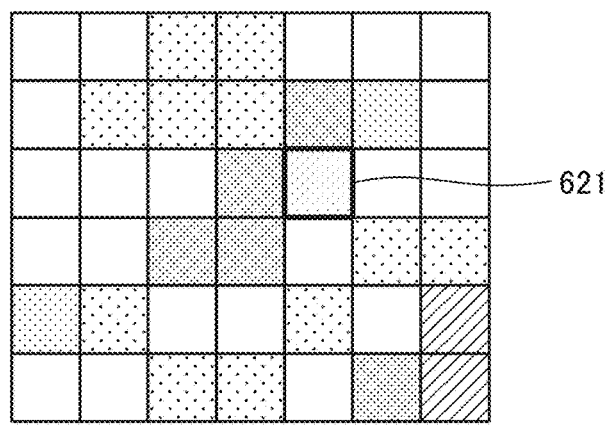
FIG. 18 is a diagram illustrating a state where one point is selected on a heat map, according to embodiments of the present disclosure.

FIG. 17 is a flowchart of region specifying processes according to the present embodiment FIG. 18 is a diagram illustrating a state where one point is selected on a heat map, according to the present embodiment.

Figure 19:
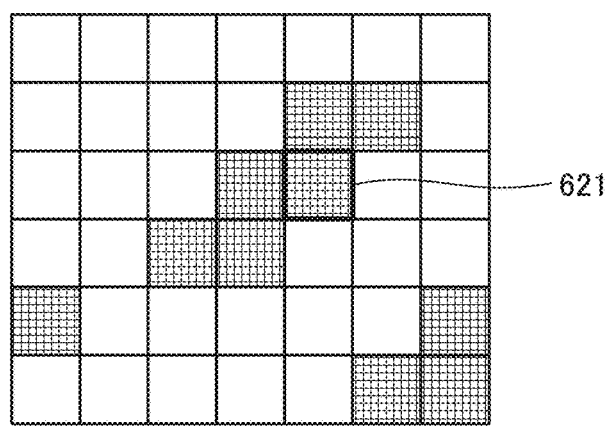
FIG. 19 is a diagram illustrating a binarized image according to embodiments of the present disclosure.

FIG. 19 is a diagram illustrating a binarized image according to the present embodiment.

Figure 20:
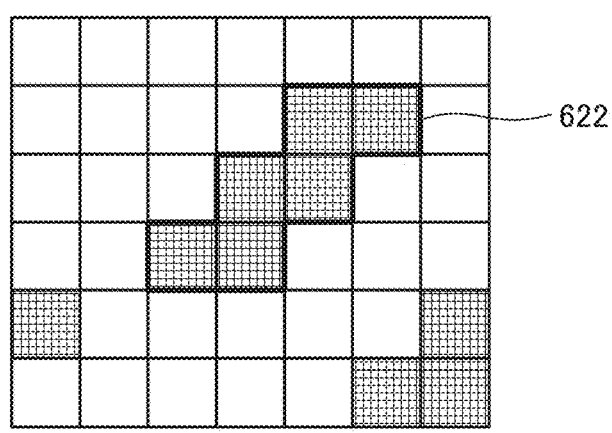
FIG. 20 is a diagram illustrating how a continuous area is regarded as a specified area, according to embodiments of the present disclosure.

FIG. 20 is a diagram illustrating how a continuous area is regarded as a specified area, according to the present embodiment.

FIG. 21A, FIG. 21B, and FIG. 21C are diagrams illustrating closing operations, according to the present embodiment.

Figure 22:
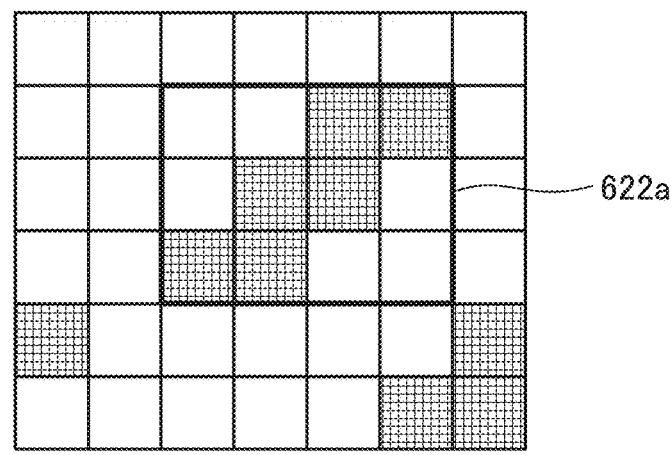
FIG. 22 is a diagram illustrating how a rectangular area that circumscribes a continuous area is regarded as a specified area, according to embodiments of the present disclosure.

FIG. 22 is a diagram illustrating how a rectangular area that circumscribes a continuous area is regarded as a specified area, according to the present embodiment.

Figure 23:
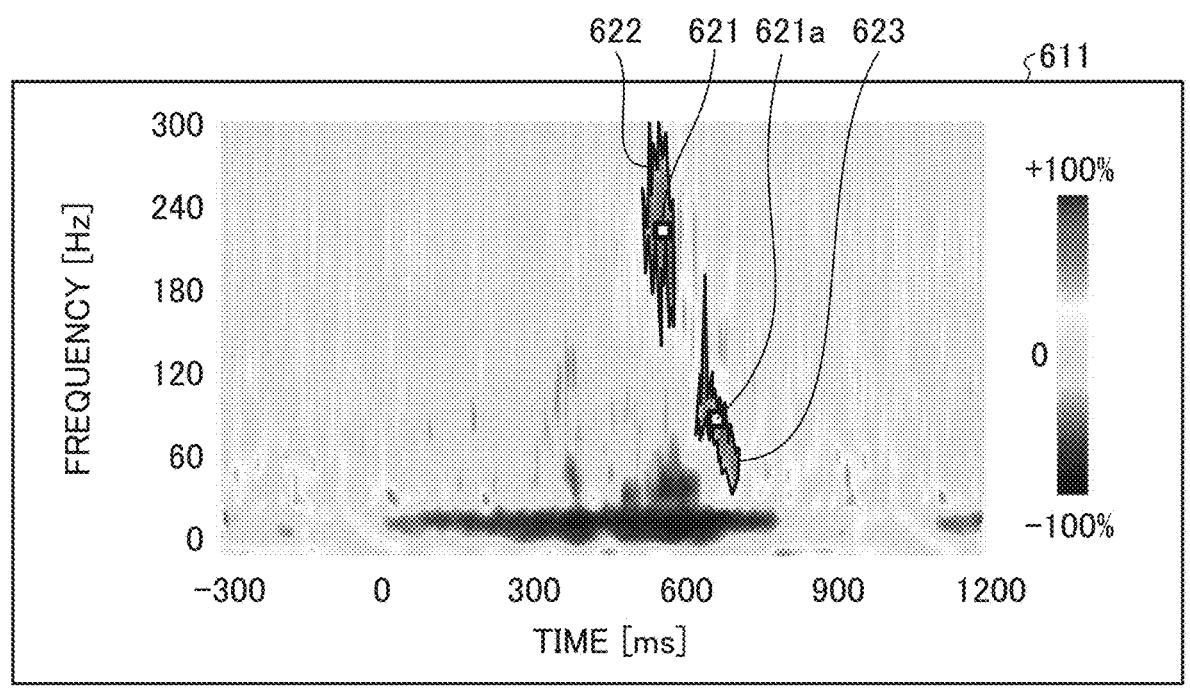
FIG. 23 is a diagram illustrating a state where a plurality of specific areas are designated on a heat map, according to embodiments of the present disclosure.

FIG. 23 is a diagram illustrating a state where a plurality of specific areas are designated on a heat map, according to the present embodiment.

Figure 24:
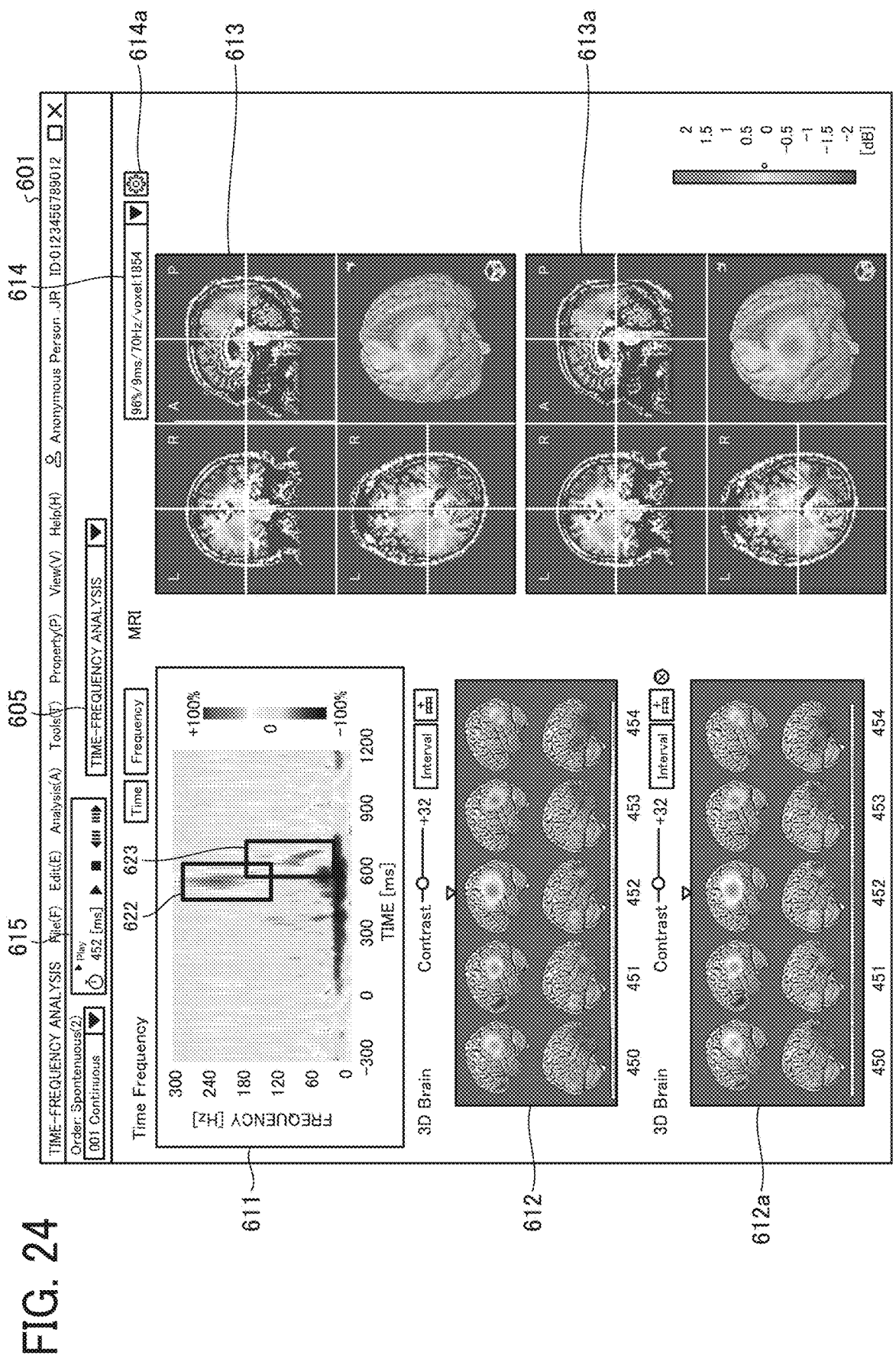
FIG. 24 is a diagram illustrating a state where another three-dimensional image and three-view head image are added to a time-frequency analysis screen, according to embodiments of the present disclosure.

FIG. 24 is a diagram illustrating a state where another three-dimensional image and three-view head image are added to the time-frequency analysis screen 601, according to the present embodiment.

Figure 25:
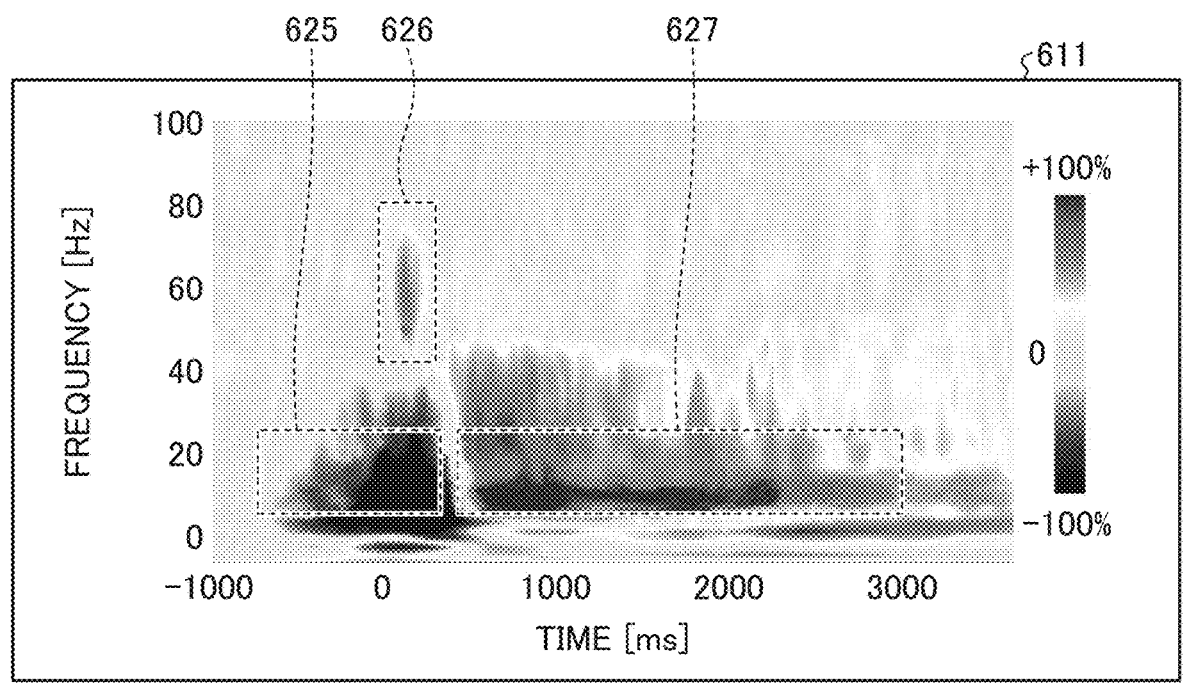
FIG. 25 is a diagram illustrating how a specified area is extracted from a predetermined area, according to embodiments of the present disclosure.

FIG. 25 is a diagram illustrating how a specified area is extracted from a predetermined area, according to the present embodiment.

In the above description made with reference to FIG. 13 to FIG. 15, as a particular position (point) is specified on the heat map 611, the distribution of the signal strength of the biomedical signals of the time and frequency corresponding to the specified position is displayed on each one of the three-dimensional view 612 and the three-view head image 613 as a heat map. Further, there are needs for displaying, as a heat map, the distribution of the signal strength of the biomedical signal that corresponds to the specified area when an area of specific time and frequency is specified on the heat map 611. However, even if an area such as a rectangular area can be specified as the analyst performs, for example, a dragging operation or a swiping operation on the input unit 208, an undesired area outside the area to be observed as a heat map, which indicates the distribution of signal strength, tends to be included. In other words, as illustrated in FIG. 16 for example, an area such as the specified area 622 where the signal strength of the biomedical signal is strong on the heat map 611 needs to be specified in some cases. It is expected the specified area 622 will be an area of the time and frequency where strong biomedical signals are generated due to the same brain activity. However, it is very difficult and annoying for the analyst to manually specify such an area like the specified area 622 as illustrated in FIG. 16. In order to handle such a situation, in the present embodiment, operations are described in which an area such as the specified area 622 as illustrated in FIG. 16 is automatically extracted. More specifically, processes as illustrated in FIG. 16 are described along the flowchart in FIG. 17, in which the specified area 622 is automatically extracted as an area that includes the specified point 621 and meets a prescribed condition once a specific position (point) on the heat map 611 is specified as a specified point 621 as the analyst performs an operation or input (clicking or tapping operation) to the input unit 208. When the specified area 622 as illustrated in FIG. 16 is automatically extracted, the distribution of the average signal strength of the biomedical signals of the time and frequency included in the specified area 622 is displayed as a heat map (second intensity distribution), which is different from the heat map on the heat map 611. For example, as illustrated in FIG. 11, the distribution of the average signal strength of the biomedical signals of the time and frequency included in the specified area 622 is displayed like sites 712a-1 to 712a-5 and 712b-1 to 712b-5 on the images of the brain in the three-dimensional view 612 (i.e., an example of an image indicative of a source), and the distribution of the average signal strength of the biomedical signals of the time and frequency included in the specified area 622 is displayed like the sites 713a-1, 713a-2, 713b, 713c, and 713d on the images of the brain in the three-view head image 613 (an example of an image indicative of a source).

In a step S21, for example, the analyst performs an operation or input (clicking or tapping operation) to the input unit 208 to specify the specified point 621 that indicates a desired point (pixel) on the heat map 611 that is magnified for view as illustrated in FIG. 18. On the heat map as illustrated in FIG. 18, the signal strength of a biomedical signal is indicated by the pixel value of each pixel, and a pixel with denser hatching indicates greater signal strength of a biomedical signal. In such a configuration, the acquisition unit 221 obtains the time and frequency at the specified point 621 and the value of the signal strength of the biomedical signal at the above-specified time and frequency. Then, the process shifts to the processes in a step S22.

In a step S22, the binarizing unit 222 determines a threshold based on the value of the signal strength obtained by the acquisition unit 221 so as to binarize the image on the heat map 611. For example, the binarizing unit 222 generates a binarized image as illustrated in FIG. 19 where the pixel value of the pixels whose value of the signal strength is equal to or greater than the value of the signal strength obtained by the acquisition unit 221 is changed to "1" (black) and the pixel value of the pixels whose value of the signal strength is less than the value of the signal strength obtained by the acquisition unit 221 is changed to "0" (white).

In the above description, the binarizing unit 222 determines a threshold based on the value of the signal strength obtained by the acquisition unit 221. However, no limitation is intended thereby. For example, the binarizing unit 222 may determine a threshold based on whether the value of the signal strength obtained by the acquisition unit 221 is equal to or greater than a predetermined rate (for example, 80%), and may sort the values into "0" or "1" based on the determined threshold. As a result, a binarized image is obtained. In such a configuration, it is desired that the predetermined rate be easily changeable using a slider or the like. Alternatively, the binarizing unit 222 may determine a threshold using a predetermined rate (for example, 70%) of the greatest signal strength of pixels searched around the position specified by the time and frequency obtained by the acquisition unit 221, and may sort the values into "0" or "1" based on the determined threshold. As a result, a binarized image is obtained. The binarizing unit 222 may determine a threshold using a threshold of a fixed rate for the signal strength, and may sort the values into "0" or "1" based on the determined threshold. As a result, a binarized image is obtained. However, in such a configuration, when the value of the signal strength obtained by the acquisition unit 221 is 0, the binarizing unit 222 has to carry out exception handling. For example, the binarizing unit 222 has display a dialog box to encourage the user to specify a different time and frequency. Alternatively, the binarizing unit 222 may determine a threshold based on the plausibility, distribution, or the standard deviation of the signal strength, which can separately be obtained by statistical analysis, instead of the value of signal strength. In such a configuration, the binarizing unit 222 sorts the values into "0" or "1" based on the determined threshold. As a result, a binarized image can be obtained. In this configuration, the heat map 611 may display a heat map of the plausibility, distribution, or the standard deviation instead of a heat map of signal strength.

Then, the process shifts to step S23.

In a step S23, the extraction unit 223 extracts, from the binarized image obtained by the binarizing unit 222, the area that includes the pixels at the position indicated by the time and frequency obtained by the acquisition unit 221, where the pixels having the pixel value "1" are combined with each other, as the specified area 622 as illustrated in FIG. 20.

According to the above region specifying processes in the steps S21 to S23, as illustrated in FIG. 16, the specified area 622 can automatically be extracted from the specified point 621 that is specified by the analyst. In other words, the analyst can specify the specified area 622 that has a complicated shape, in an automatic manner, just by specifying a point on the heat map 611 with a clicking operation or the like.

Note also that the extraction unit 223 may extract a specified area upon performing the closing operations as illustrated in FIG. 21A, FIG. 21B, and FIG. 21C on the binarized image obtained by the binarizing unit 222. For example, it is assumed that the image as illustrated in FIG. 21A is a binarized image obtained by the binarizing unit 222. In the closing operations, first of all, the extraction unit 223 performs expansion processes on the binarized image as illustrated in FIG. 21A to obtain an image as illustrated in FIG. 21B. Then, the extraction unit 223 performs erosion processes on the image as illustrated in FIG. 21B to obtain an image as illustrated in FIG. 21C. Due to such a configuration, the extraction unit 223 can combine two or more connected regions that have a small gap therebetween on the originally-obtained binarized image. Accordingly, even if the precision of threshold setting for the binarizing unit 222 to perform binarization is insufficient, a specified area can be extracted in an appropriate manner. Note also that the extraction unit 223 may perform opening operations to execute dilation processes in place of or in addition to the closing operations, after erosion processes. Due to such a configuration, the extraction unit 223 can exclude, for example, small connected regions that are not to be included in a specified area.

What is to be extracted by the extraction unit 223 is not limited to the specified area 622 that has a complicated shape, as illustrated in FIG. 20. For example, as illustrated in FIG. 22, the extraction unit 223 may extract a rectangular area that circumscribes an area corresponding to the specified area 622 as obtained above, as a specified area 622a. For purposes of simplification, the extraction unit 223 may check the values of signal strength in the up-and-down and right-and-left directions based on the position designated on the heat map 611 by clicking operation or the like, and may extract a rectangular area where the value of signal strength is at least more than the value obtained by multiplying the value of the signal strength at the specified position by a predetermined rate (for example, 80%), as the specified area 622a.

As illustrated in FIG. 23, the analyst may perform additional operation (for example, new clicking or tapping operation) on the input unit 208. Due to this configuration, when a specified point 621a is specified in addition to the specified area 622 that has already been specified, a specified area 623 can additionally be specified through the region specifying processes performed on the specified point 621a as described above with reference to FIG. 17. In such a case, as illustrated in FIG. 24, a three-dimensional view 612a and a three-view head image 613a are displayed as the three-dimensional image and three-view head image that correspond to the newly-specified specified area 623, respectively. Then, the distribution of the average signal strength of the biomedical signals corresponding to the time and frequency included in the specified area 623 is displayed on the brain images of the three-dimensional view 612 and the three-view head image 613a as a heat map. Note that this heat map is different from the heat map on the heat map 611. When the information about multiple specifying operations is received through the heat map 611, the three-dimensional view 612 and the three-view head image 613 that correspond to the above information about specifying operations are displayed in descending order of time of receipt (in the direction from top to bottom). FIG. 24 illustrates an example in which the specified area 622 is selected and then the specified area 623 is selected. Due to such manner of presentation, the analyst can easily and intuitively figure out the situation. Alternatively, when the information about multiple selecting operations is received through the heat map 611, the three-dimensional view 612 and the three-view head image 613 that correspond to the above information about specifying operations are displayed in ascending order of time of receipt (in the direction from bottom to top). In such a configuration, the three-dimensional view 612 and the three-view head image 613 that correspond to the latest selected area are displayed directly below the heat map 611. Accordingly, the shift of the line of vision of the analyzer to the heat map 611, the three-dimensional view 612, and the three-view head image 613 can be reduced. When a plurality of points are specified on the heat map 611, not only areas such as the specified areas 622 and 623 but also a plurality of points such as the specified point 621 may be specified. When a plurality of positions (points or areas) are specified on the heat map 611 as described above, the multiple distributions of the signal strength of the biomedical signals of the time and frequency corresponding to the specified positions can be compared with each other.

For example, the timing at which the analyst clicks or taps a desired point of the heat map 611 may be used as a trigger, and the extraction unit 223 may use the threshold that is determined in advance by the binarizing unit 222 to extract each one of all the connected regions from the binarized image, as a specified area. In such a configuration, a heat map may be superimposed on each one of the three-dimensional view 612, a three-dimensional view 612a, and so on, and the three-view head image 613, a three-view head image 613a, and so on, which correspond to each extracted specified area. Alternatively, a heat map that corresponds to the specified area that is selected by the analyst from the multiple specified areas extracted by the extraction unit 223 may be displayed on the three-view head image 613 and the three-dimensional view 612. In such a configuration, immediately after a plurality of specified areas are extracted by the extraction unit 223, a heat map that corresponds to, for example, the specified area in which the average of the signal strength is largest may be displayed on the three-view head image 613 and the three-dimensional view 612.

There are some cases in which areas of times and frequencies to be focused on are determined in advance on the heat map 611 according to a specific human activity (such as hand shaking). For example, when the target human activity is movement, the analyst tends to perform analysis upon focusing on predetermined areas 625 to 627 in the heat map 611 as illustrated in FIG. 25. In such a configuration, the binarizing unit 222 may binarize the areas 625 to 627, and may extract a combined area from the binarized image that corresponds to each of the binarized areas. As a result, a specified area is determined. In such a configuration, the actual positions of the areas 625 to 627 are determined with reference to, for example, the position of time 0 on the heat map 611. However, there are variations among individuals in the brain activity even if the areas 625 to 627 are analyzed in some extent. In view of such circumstances, it is desired that an imprecise area be set in advance and the time and frequency be examined closely within that area. For example, the center point of each of the areas 625 to 627 (an example of a representative point) is specified in advance, and assuming that the analyst clicks or taps each of the center points, the specified area that corresponds to each one of the center points can be extracted due to the region specifying processes as described above with reference to FIG. 17. By so doing, a specified area can more appropriately be extracted taking in consideration the variations among individuals.

Figure 26:
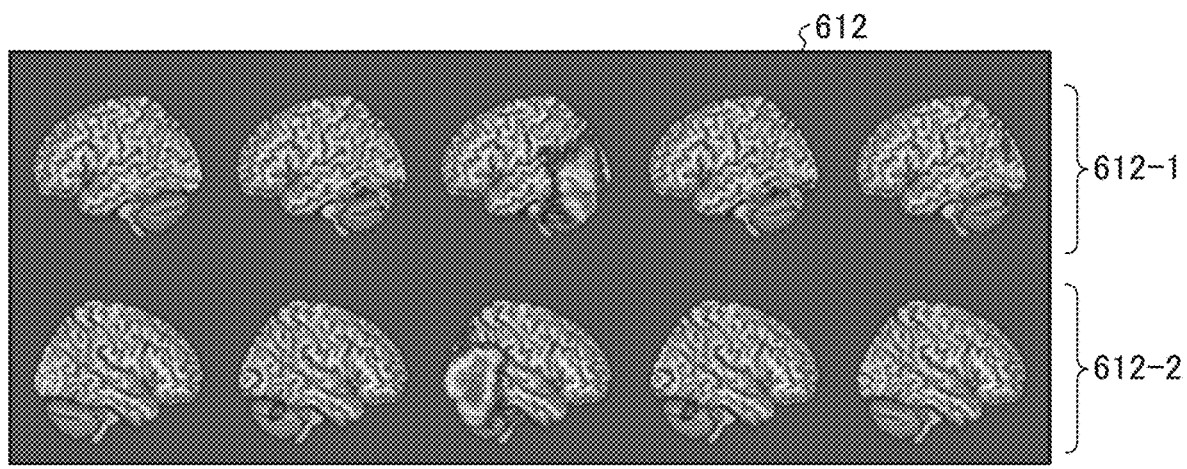
FIG. 26 is a diagram illustrating a three-dimensional image on a time-frequency analysis screen, according to embodiments of the present disclosure.

FIG. 26 is a diagram illustrating the three-dimensional view 612 on the time-frequency analysis screen 601, according to the present embodiment.

Figure 27:
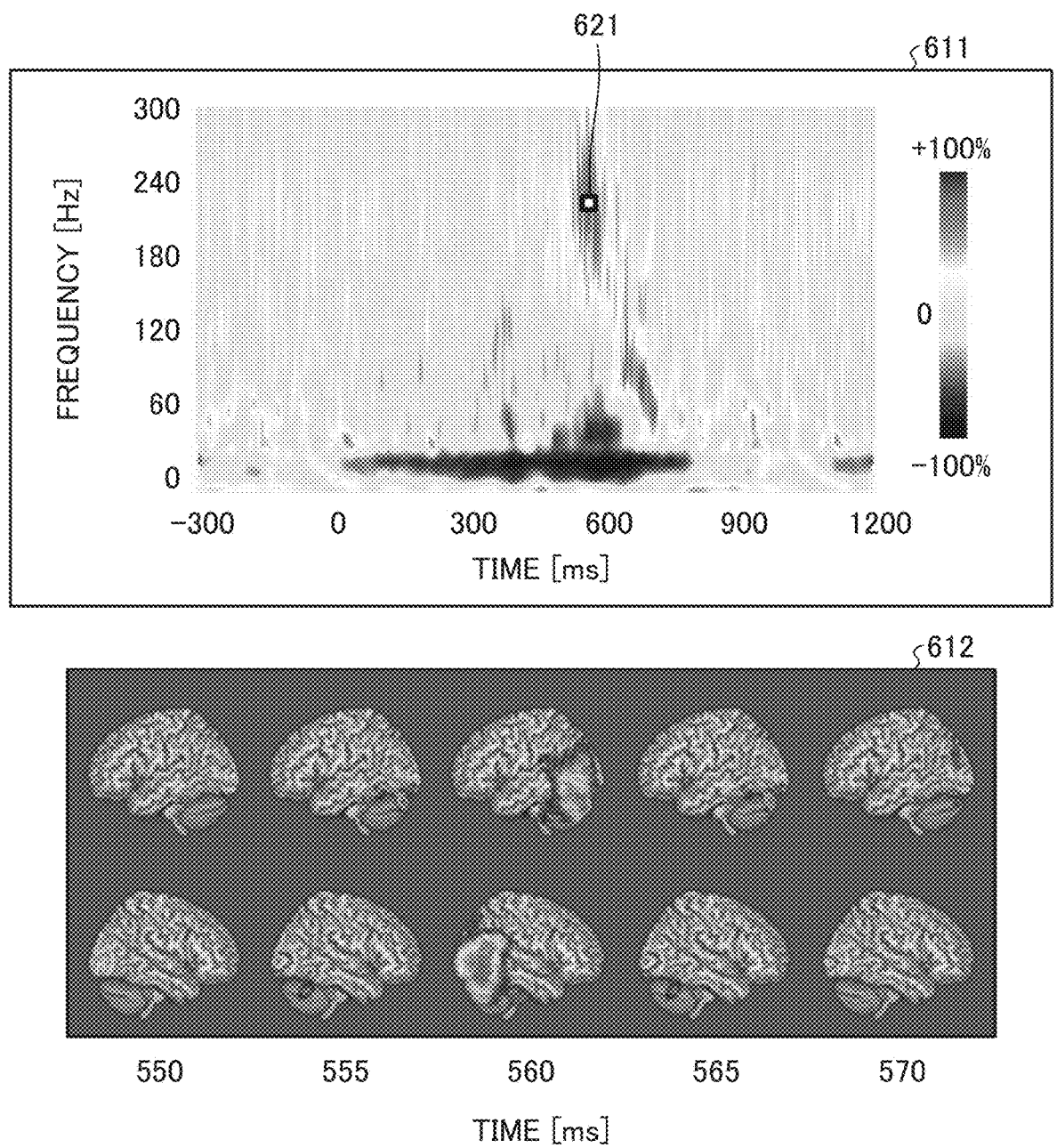
FIG. 27 is a diagram in which the state of the brain, which corresponds to the position designated on a heat map, is displayed in the center on a three-dimensional image, according to embodiments of the present disclosure.

FIG. 27 is a diagram in which the state of the brain, which corresponds to the position designated on the heat map 611, is displayed in the center on the three-dimensional view 612, according to the present embodiment.

Figure 28:
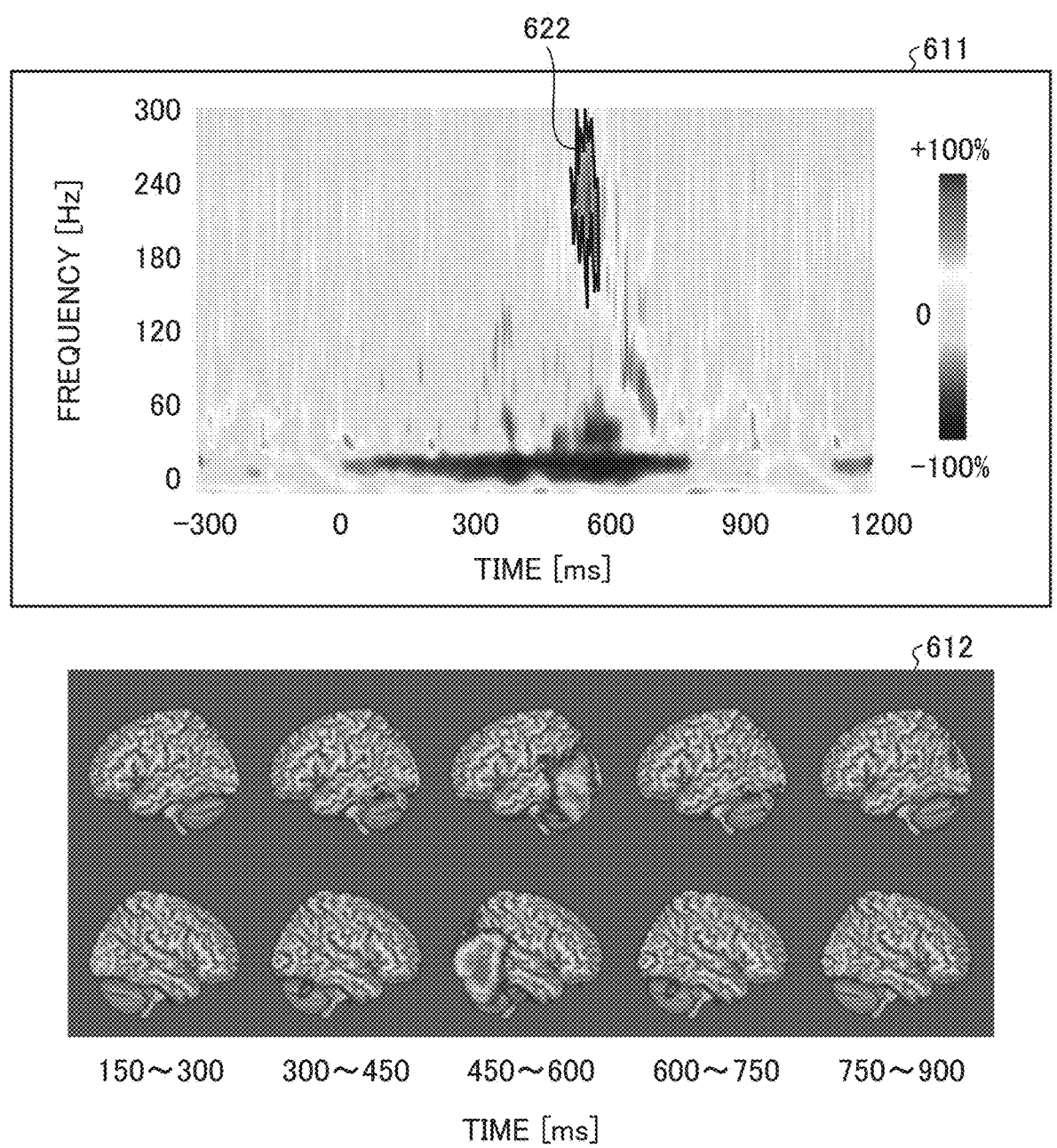
FIG. 28 is a diagram in which the state of the brain, which corresponds to the range designated on a heat map, is displayed in the center on a three-dimensional image, according to embodiments of the present disclosure.

FIG. 28 is a diagram in which the state of the brain, which corresponds to the area designated on the heat map 611, is displayed in the center on the three-dimensional view 612, according to the present embodiment.

Figure 29:
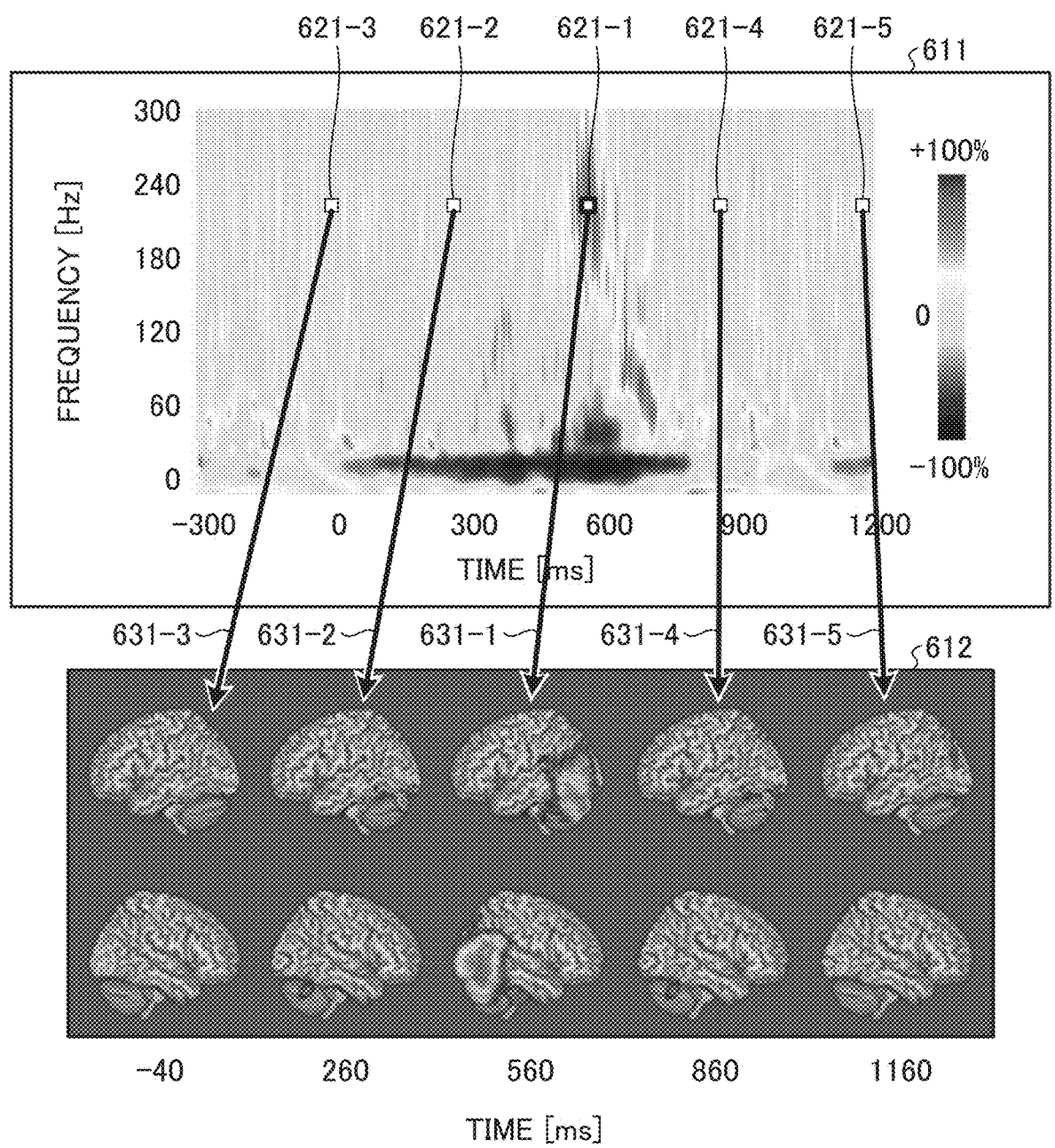
FIG. 29 is a diagram in which line segments are used to indicate to what time and frequency on a heat map each one of the images of a brain displayed as a three-dimensional image corresponds, according to embodiments of the present disclosure.

FIG. 29 is a diagram in which line segments are used to indicate to what time and frequency on the heat map 611 each one of the images of the brain displayed as the three-dimensional view 612 corresponds, according to the present embodiment.

FIG. 30 is a diagram in which rectangular areas are used to indicate to what time and frequency on the heat map 611 each one of the images of the brain displayed as the three-dimensional view 612 corresponds to, according to the present embodiment.

FIG. 31A and FIG. 31B are diagrams illustrating how the display on the three-dimensional view 612 and the display of the rectangular regions on the heat map 611 move as the three-dimensional view 612 is dragged, according to the present embodiment.

Figure 32B:
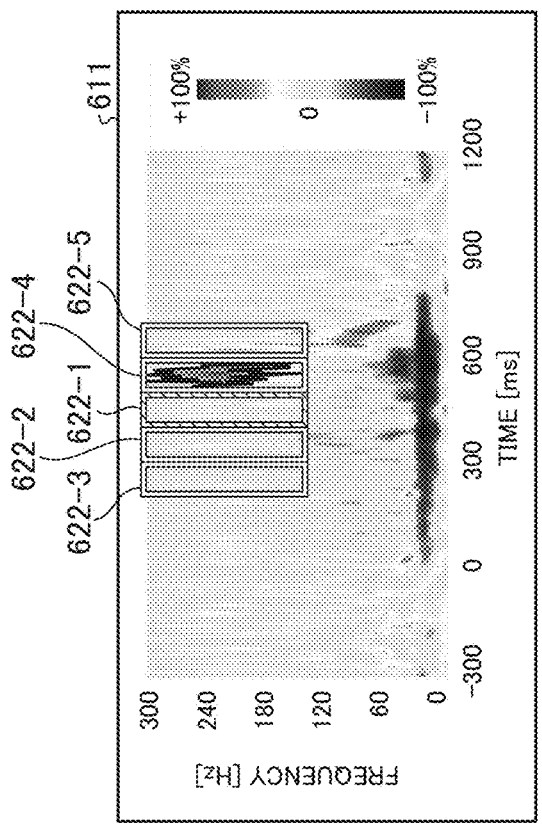
FIG. 32A and FIG. 32B are diagrams illustrating how the display on a three-dimensional image and the display of the rectangular regions on a heat map move as one of the brain images on the three-dimensional image is clicked, according to embodiments of the present disclosure.
Figure 32A:
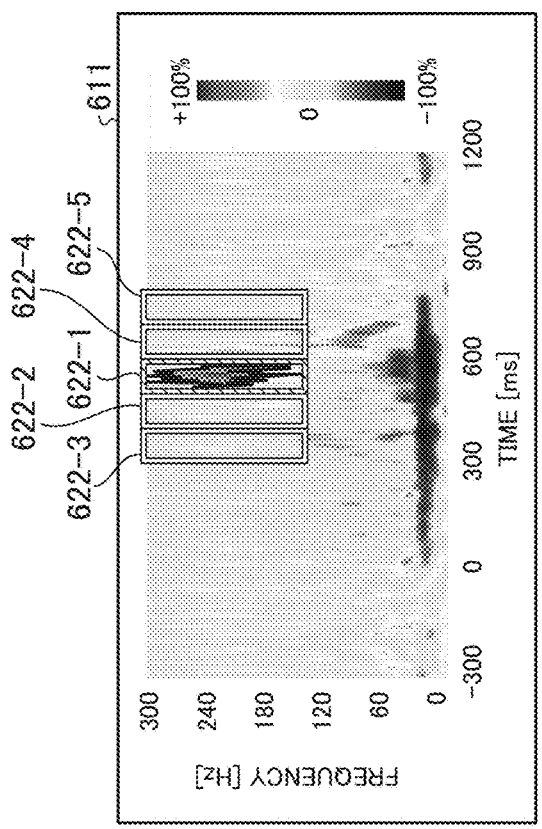

FIG. 32A and FIG. 32B are diagrams illustrating how the display on the three-dimensional view 612 and the display of the rectangular regions on the heat map 611 move as one of the brain images on the three-dimensional view 612 is clicked, according to the present embodiment.

Basic display operation of the three-dimensional view 612 on the time-frequency analysis screen 601 is described below with reference to FIG. 26 to FIG. 32B.

As illustrated in FIG. 26, the three-dimensional view 612 is a view of the three-dimensional images (3D image) of the brain from a prescribed viewpoint, and the position (point or area) designated on the heat map 611 or the signal strength of the biomedical signal that corresponds to the peak selected from the peak list 614 is superimposed on the three-dimensional view 612 as a heat map (second intensity distribution). As illustrated in FIG. 26, in the same row of the three-dimensional view 612, three-dimensional images of a brain from the same viewpoint are displayed. In the example as illustrated in FIG. 26, the three-dimensional images of the brain as displayed in the display area 612-1 in the upper row of the three-dimensional view 612 are viewed from a viewpoint on the left side of the brain, and the three-dimensional images of the brain as displayed in the display area 612-2 in the lower row of the three-dimensional view 612 are viewed from a viewpoint on the right side of the brain. The display operation of the three-dimensional view 612 is controlled by the three-dimensional display control unit 212.

As illustrated in FIG. 26, the three-dimensional view 612 consists of three-dimensional images of a brain viewed from two viewpoints, and such three-dimensional images of a brain are displayed in two rows. However, no limitation is intended thereby, and three-dimensional images of a brain may be displayed in any other numbers of rows. The number of rows may be changed as desired. For example, when the language area of the brain is to be measured, the difference between right and left sides of the brain is crucial information. For this reason, the three-dimensional images of the brain that are viewed from two different viewpoints, consisting of a viewpoint on the right side of the brain and a viewpoint on the left side of the brain, are to be displayed in two rows. Some example associations between an object to be measured and desired viewpoints are depicted in a first table given below. The object to be measured includes the stimulation given to a test subject during the measurement (such stimulation is given by a stimulator and the rows in No. 1 to No. 4 of the first table are relevant) and the motion made by the test subject (see No. 5 of the first table), and indicates the items from which selection is to be made on the measurement and collection screen 502 when collection is to be performed. Once the object to be measured is selected, the three-dimensional view 612 of the brain that is viewed from the corresponding viewpoint is displayed. The term viewpoint indicates the direction with the origin located at the front of the test subject. As a matter of course, the number of rows may be edited in a separate manner. The three-dimensional view 612 as illustrated in FIG. 26 corresponds to No. 2 in the first table. For the sake of explanatory convenience, it is assumed in the following description that the three-dimensional view 612 consists of two rows (images viewed from two viewpoints).

| First Table | | |
|---|---|---|
| No. | OBJECT TO BE MEASURED | VIEWPOINT |
| 1 | VISUAL PERCEPTION | REAR (VIEWPOINT TO VIEW OCCIPITAL REGION FROM BACK OF OCCIPITAL REGION) ONE ROW |
| 2 | AUDITORY SENSATION | RIGHT (VIEWPOINT TO VIEW RIGHT TEMPORAL REGION FROM OUTSIDE RIGHT TEMPORAL REGION) AND LEFT (VIEWPOINT TO VIEW LEFT TEMPORAL REGION FROM OUTSIDE LEFT TEMPORAL REGION) ONE ROW FOR RIGHT, ONE ROW FOR LEFT |
| 3 | LANGUAGE | RIGHT AND LEFT |
| 4 | SOMATIC SENSATION | TOP |
| 5 | MOTION | TOP |

When the specified point 621 is specified on the heat map 611 as illustrated in FIG. 27, the three-dimensional display control unit 212 sets the time that corresponds to the specified point 621 to the center of the display area of the three-dimensional view 612, and controls the display to display on the three-dimensional view 612 the heat map of the signal strength on the brain at the times before and after the time that corresponds to the specified point 621. In the example as illustrated in FIG. 27, the time 560 ms is specified on the heat map 611. Accordingly, the intervals at which the brains are displayed are set to 5 ms, and the images of the brain at 550, 555, 560, 565, and 570 ms around 560 ms are displayed on the three-dimensional view 612. However, no limitation is indicated thereby, and the intervals at which the images of the brain are displayed may be edited to, for example, 10 ms or 25 ms.

As illustrated in FIG. 28, when an area (i.e., the specified area 622) is specified on the heat map 611, the heat map of signal strength where the signal strength within that selected area is averaged may be displayed on the three-dimensional view 612. In such a configuration, the times of the neighboring three-dimensional images displayed on the three-dimensional view 612 may be adjusted according to the selected range of time.

As illustrated in FIG. 28, for example, when the range of time of the specified area 622 is between 450 and 600 ms and the intervals at which the neighboring three-dimensional images are displayed in the three-dimensional view 612 is set to 150 ms, the range of time of the three-dimensional image that is displayed in the center of the three-dimensional view 612 is 450 to 600 ms. Moreover, the range of time of the three-dimensional image on the left side of the three-dimensional image in the center of the three-dimensional view 612 is 300 to 450 ms, and the range of time of the three-dimensional image on the right of the three-dimensional image in the center of the three-dimensional view 612 is 600 to 750 ms. The heat map that is displayed on each three-dimensional image indicates, for example, the average in each range of time.

The association between the positions or ranges on the heat map 611 and the multiple three-dimensional images on the three-dimensional view 612 is described below with reference to FIG. 22 and FIG. 23. First of all, as illustrated in FIG. 22, when a specified point 621-1 is specified on the heat map 611, the three-dimensional image of the brain, which corresponds to the time and frequency of the specified point 621-1, is displayed on the three-dimensional view 612. In this configuration, the three-dimensional images of the brain at the times before and after the time that corresponds to the specified point 621-1 are displayed around the above three-dimensional image of the brain. In the example as illustrated in FIG. 22, the images of the brain that correspond to five points in time are displayed. Accordingly, the heat-map display control unit 211 control the display to display the points that correspond to the respective points in time of the brain on the heat map 611 as corresponding points 621-2 to 621-5, respectively. In such a configuration, the positions in frequency of the corresponding points 621-2 to 621-5 are made consistent with the position in frequency of the specified point 621-1. Further, as illustrated in FIG. 22, the heat-map display control unit 211 controls the display to display line segments 631-1 to 631-5 that connect the specified point 621-1 and the corresponding points 621-2 to 621-5 on the heat map 611 and the corresponding three-dimensional images of the brain on the three-dimensional view 612. Due to this configuration, to what positions on the heat map 611 the states of the brain as displayed on the three-dimensional view 612 correspond to can be checked instantly. In the example as illustrated in FIG. 22, line segments are adopted. However, no limitation is indicated thereby, and any other ways of association may be adopted. For example, the marks of the specified point 621-1 and the corresponding points 621-2 to 621-5 may be associated with the colors of the background of the images of the brain in the three-dimensional view 612. In such a case, the specified point 621-1 that is specified by the analyst is to be displayed in a mode distinguishable from the corresponding points 621-2 to 621-5.

When a specified area 622-1 is specified as a specific area on the heat map 611, firstly, as illustrated in FIG. 23, the three-dimensional image of the brain, which corresponds to the time and frequency on the specified area 622-1, is displayed in the three-dimensional view 612. In this configuration, the specified area 622-1 is, for example, a rectangular area that circumscribes the connected region extracted by the extraction unit 223. In this configuration, the three-dimensional images of the brain at the ranges of time before and after the range of time that corresponds to the specified area 622-1 are displayed around the above three-dimensional image of the brain. In the example as illustrated in FIG. 30, the images of the brain that correspond to five ranges of time are displayed. Accordingly, the heat-map display control unit 211 control the display to display the ranges that correspond to the respective ranges of time of the brain on the heat map 611 as related areas 622-2 to 622-5, respectively. In such a case, the specified area 622-1 that is specified by the analyst is to be displayed in a mode distinguishable from the related areas 622-2 to 622-5. For example, the color of the rectangular frame of the specified area 622-1 may be differentiated from the other frames. Further, as illustrated in FIG. 30, the three-dimensional display control unit 212 controls the display to display rectangles similar to the specified area 622-1 and the related areas 622-2 to 622-5 on the heat map 611 to surround the corresponding three-dimensional images of the brain in the three-dimensional view 612. Due to this configuration, to what ranges on the heat map 611 the states of the brain as displayed in the three-dimensional view 612 correspond to can be checked instantly. When the specified area 622-1 is specified as a specific area on the heat map 611, the frames of the specified area 622-1 and the related areas 622-2 to 622-5 may be displayed, and frames 722-1 to 722-5 and the heat maps may be displayed in the three-dimensional view 612.

Operations where the display in the three-dimensional view 612 is moved to the right and left sides when a dragging operation, swiping operation, or a cursor-movement key operation is performed in the three-dimensional view 612 are described below with reference to FIG. 31A, FIG. 31B, FIG. 32A, and FIG. 32B. FIG. 31A and FIG. 31B are diagrams illustrating a state in which the three-dimensional images in the three-dimensional view 612 are moved to the right side by a dragging operation, swiping operation, or a cursor-movement key operation performed in the three-dimensional view 612, according to the present embodiment. In such a case, as illustrated in FIG. 31A and FIG. 31B, as a result of the movement, the display of time is updated in accordance with the brains that are currently displayed, and a rectangle is displayed to indicate that the three-dimensional image of the brain displayed in the center of the three-dimensional view 612 is selected. Further, the three-dimensional display control unit 212 moves the display of the specified area 622-1 and the related areas 622-2 to 622-5 on the heat map 611 in accordance with the movement of the three-dimensional images in the three-dimensional view 612.

As illustrated in FIG. 32A and FIG. 32B, when one of the three-dimensional images other than the three-dimensional image in the center of the three-dimensional view 612 is clicked or tapped by the analyst, the operated three-dimensional image of the brain moves to the center of the three-dimensional view 612. In the actual implementation, only the overlapping heat map may be moved and the positions of the images of the brain may remain the same. In such a case, as illustrated in FIG. 32A and FIG. 32B, as a result of the movement, the display of time is updated in accordance with the brains that are currently displayed, and a rectangle is displayed to indicate that the three-dimensional image of the brain displayed in the center of the three-dimensional view 612 is selected. Further, the three-dimensional display control unit 212 moves the display of the specified area 622-1 and the related areas 622-2 to 622-5 on the heat map 611 in accordance with the movement of the three-dimensional images in the three-dimensional view 612.

As described above, the display in the three-dimensional view 612 can be moved as desired. Due to such a configuration, the changes in the state of the brain across the time can quickly be recognized.

Operations in which the viewpoint of a desired three-dimensional image of the three-dimensional view 612 on the time-frequency analysis screen 601 is changed are described below with reference to FIG. 33A to FIG. 38.

Figure 33A:
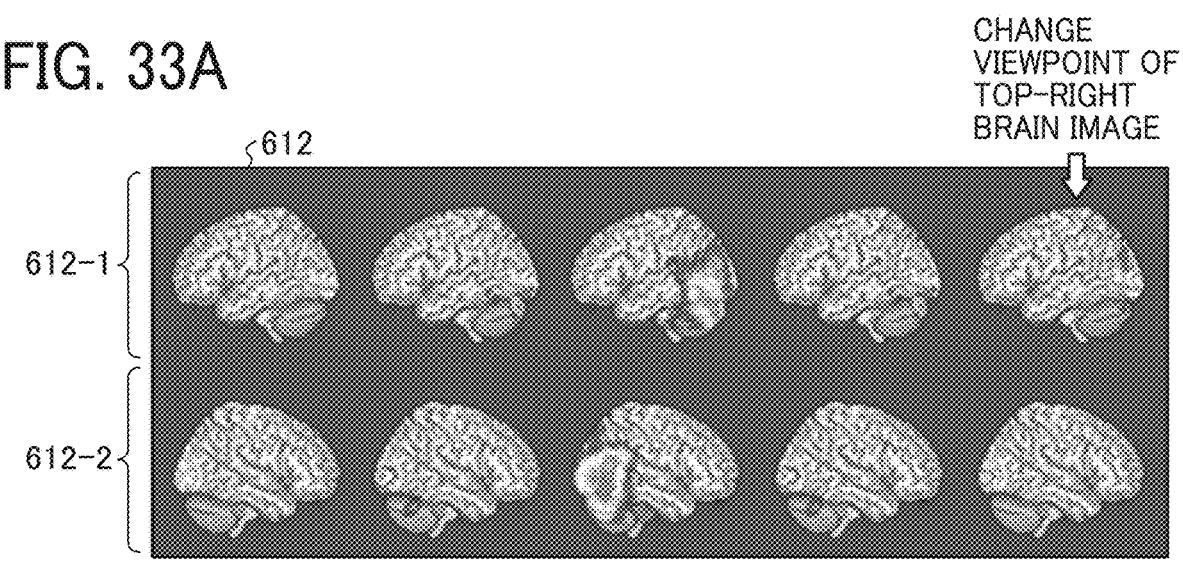
FIG. 33A, FIG. 33B, and FIG. 33C are diagrams illustrating how the viewpoints of all brain images in the same row are changed when one of the viewpoints of the brain displayed on a three-dimensional image is changed, according to embodiments of the present disclosure.
Figure 33B:
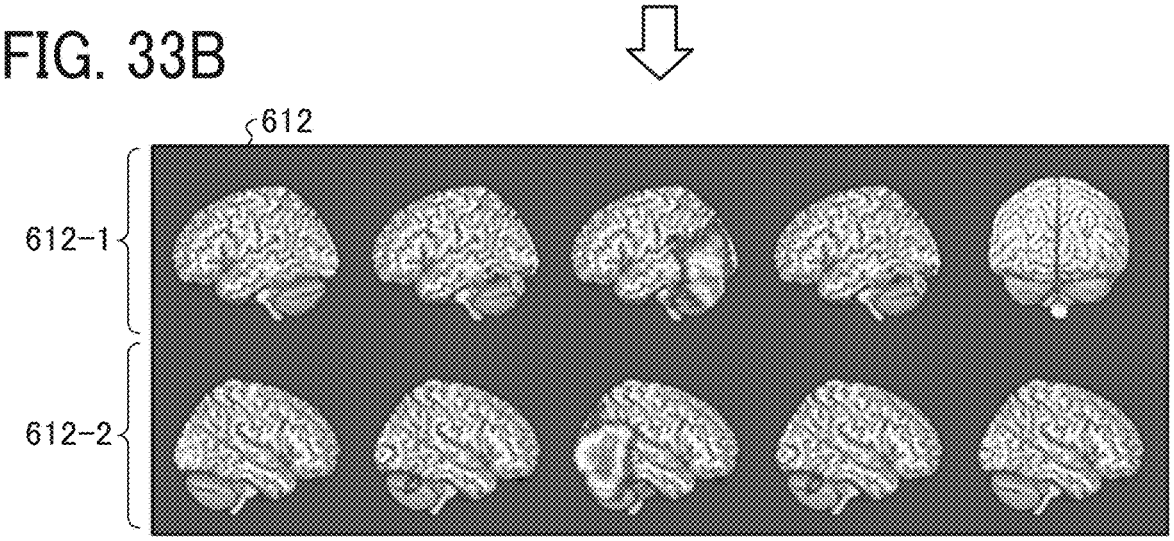
Figure 33C:
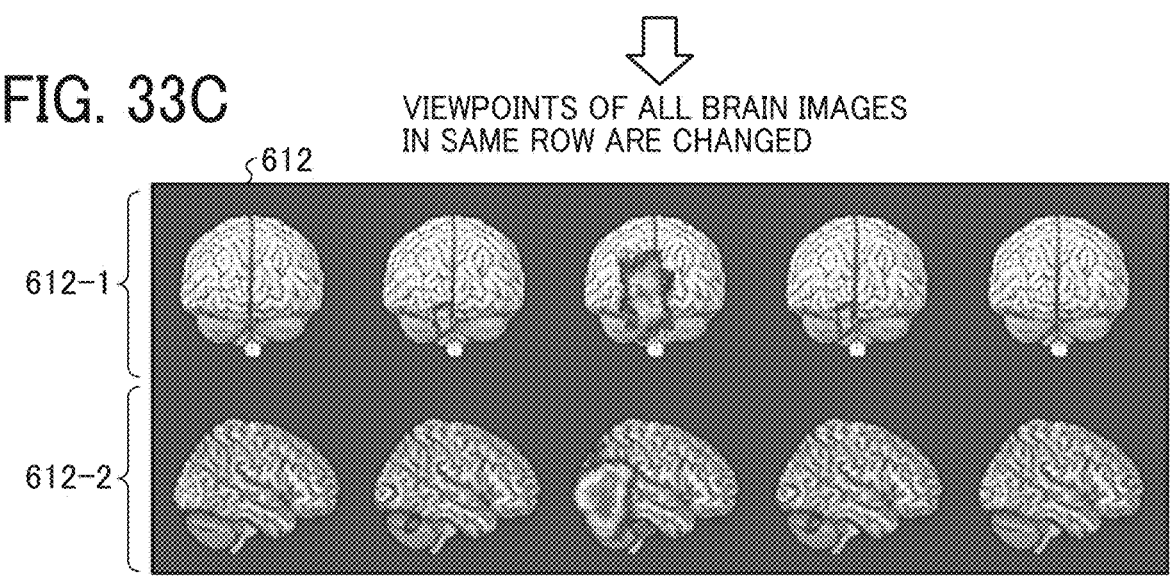

FIG. 33A, FIG. 33B, and FIG. 33C are diagrams illustrating how the viewpoints of all brain images in same row are changed when one of the viewpoints of the brain displayed in the three-dimensional view 612 is changed, according to the present embodiment.

Figure 34A:
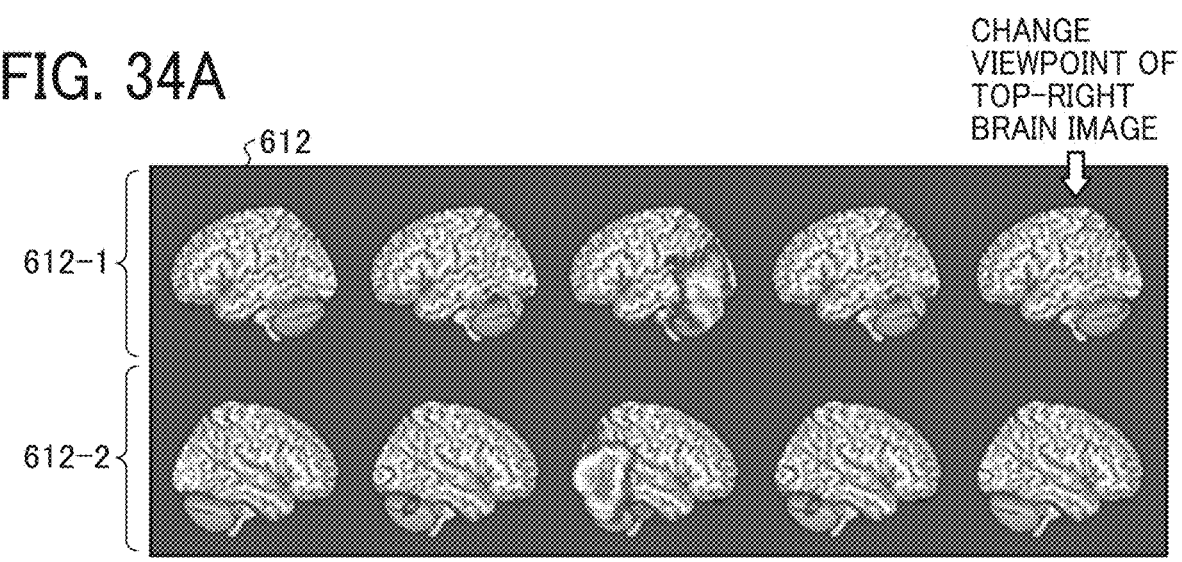
FIG. 34A, FIG. 34B, and FIG. 34C are diagrams illustrating how the viewpoints of all the brain images in all the rows are changed when one of the viewpoints of the brain displayed on a three-dimensional image is changed, according to embodiments of the present disclosure.
Figure 34B:
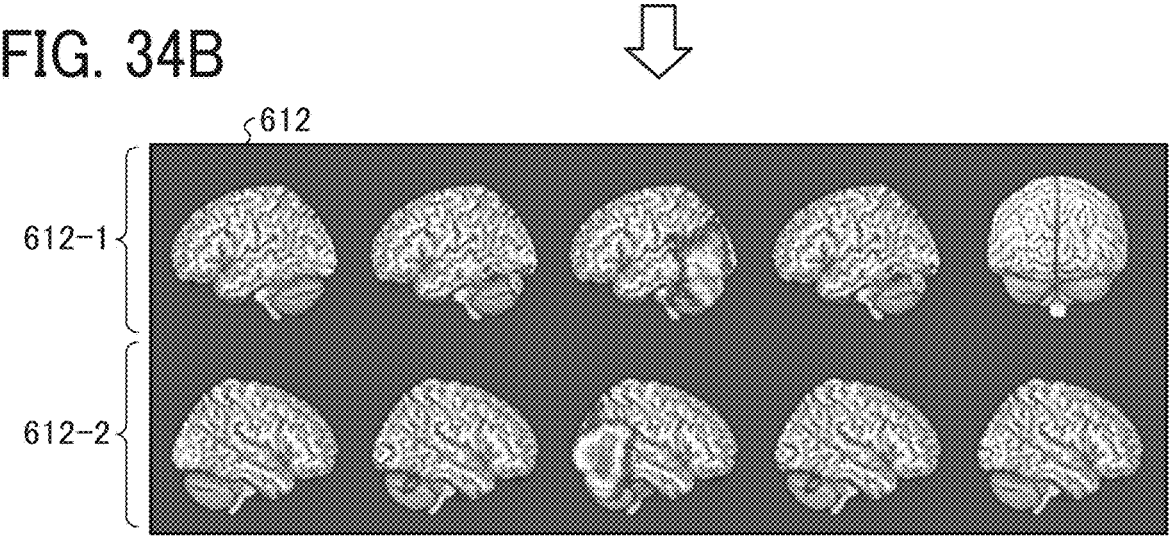
Figure 34C:
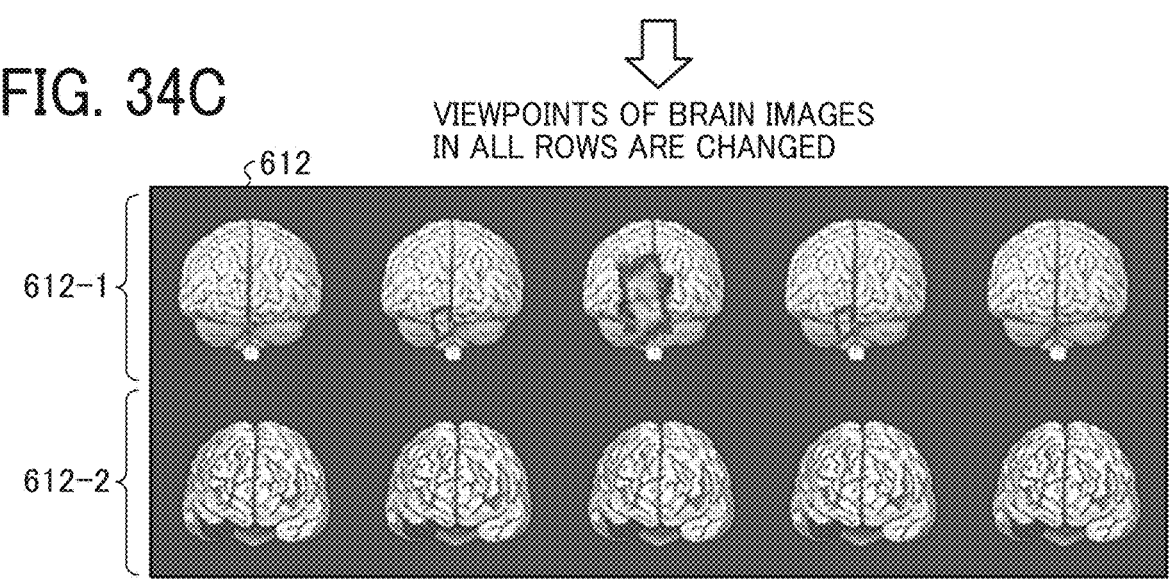

FIG. 34A, FIG. 34B, and FIG. 34C are diagrams illustrating how the viewpoints of all the brain images in all the rows are changed when one of the viewpoints of the brain displayed in the three-dimensional view 612 is changed, according to the present embodiment.

FIG. 35A, FIG. 35B, and FIG. 35C are diagrams illustrating in detail how the viewpoint is changed in FIG. 34A, FIG. 34B, and FIG. 34C, according to the present embodiment.

FIG. 36A, FIG. 36B, and FIG. 36C are another set of diagrams illustrating how the viewpoints of all the brain images in all the rows are changed when one of the viewpoints of the brain displayed in the three-dimensional view 612 is changed, according to the present embodiment.

FIG. 37A, FIG. 37B, and FIG. 37C are diagrams illustrating the details of how the viewpoint is changed as in FIG. 36A, FIG. 36B, and FIG. 36C, according to the present embodiment.

Figure 38:
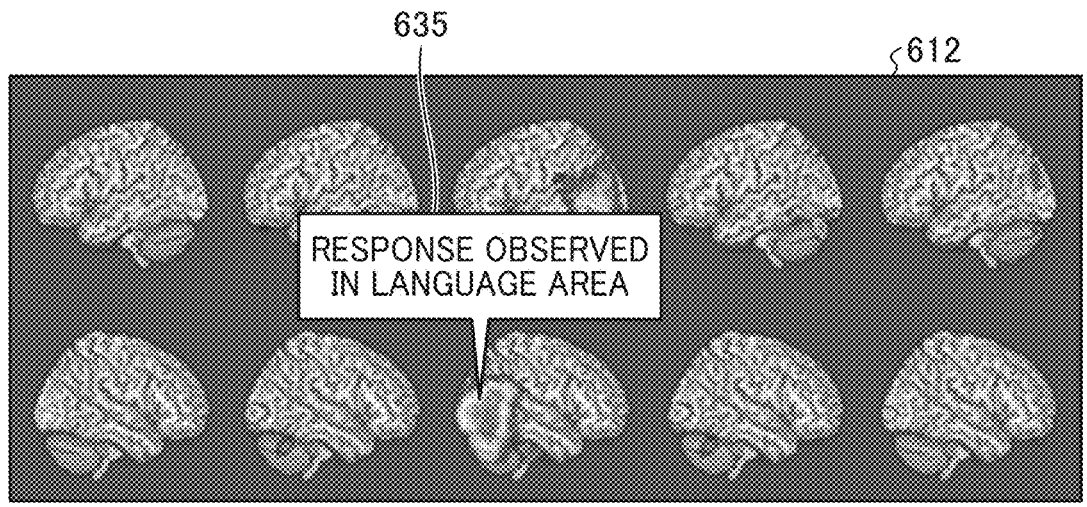
FIG. 38 is a diagram illustrating a state in which a comment is added to a three-dimensional image, according to embodiments of the present disclosure.

FIG. 38 is a diagram illustrating a state in which a comment is added to the three-dimensional view 612, according to the present embodiment.

The viewpoint of the brains that are displayed as three-dimensional images in the three-dimensional view 612 can be changed as manipulated by the analyst (for example, a dragging operation or a swiping operation). Some patterns of a method of reflecting the changes made in the viewpoint of a specific three-dimensional image of the brain in the three-dimensional view 612, in the other three-dimensional images, are described below.

Firstly, cases in which the viewpoint of the other three-dimensional images in the same row is changed in a similar manner when the viewpoint of a specific three-dimensional images is changed are described. As illustrated in FIG. 33A, it is assumed that the analyst has performed an operation on the three-dimensional view 612 displayed in two rows to change the viewpoint of the three-dimensional image at the right end (such a three-dimensional image may be referred to as a target three-dimensional image in the following description) from among the multiple three-dimensional images of the brain as displayed in the display area 612-1. In such a case, as illustrated in FIG. 33B, as manipulated by the analyst, the three-dimensional display control unit 212 changes the viewpoint of the target three-dimensional images with the viewpoint from the left side of the brain so as to display the three-dimensional images of the brain viewed from a rear side. In so doing, the viewpoint of the heat maps that are superimposed on the images of the brain is also changed in a similar manner. Then, as illustrated in FIG. 33C, the three-dimensional display control unit 212 changes the viewpoint of the other three-dimensional images of the brain in the same row as the target three-dimensional images (in the display area 612-1) in a similar manner to the target three-dimensional image. Due to this configuration, the changes that are made in the viewpoint of a specific three-dimensional image (i.e., the target three-dimensional image) are automatically reflected in the other three-dimensional images in the same row. Accordingly, the operability or efficiency improves, and the changes in activity among the images of the brain that viewed from the same viewpoint and are temporally close to each other can easily be checked. When the analyst wishes to change the viewpoint of a three-dimensional image, for example, he or she may manipulate mouse to move the cursor onto the three-dimensional image whose viewpoint is to be changed, and may perform, for example, dragging or clicking operation. Alternatively, the analyst may designate a parameter in a pop-up window.

Secondly, cases in which the viewpoint of the other three-dimensional images is changed in a similar manner when the viewpoint of a specific three-dimensional images is changed are described. As illustrated in FIG. 34A, it is assumed that the analyst has performed an operation on the three-dimensional view 612 displayed in two rows to change the viewpoint of the target three-dimensional image at the right end from among the multiple three-dimensional images of the brain as displayed in the display area 612-1. In such a case, as illustrated in FIG. 34B, as manipulated by the analyst, the three-dimensional display control unit 212 changes the viewpoint of the target three-dimensional images with the viewpoint from the left side of the brain so as to display the three-dimensional images of the brain viewed from a rear side. Then, as illustrated in FIG. 34C, the three-dimensional display control unit 212 changes the viewpoint of the other three-dimensional images of the brain in the same row as the target three-dimensional images (in the display area 612-1) in a similar manner to the target three-dimensional image. In other words, the three-dimensional display control unit 212 changes the viewpoint of the other three-dimensional images of the brain as displayed in the display area 612-1 on the left side of the brain as illustrated in FIG. 28A so as to display the three-dimensional images of the brain viewed from a rear side, as illustrated in FIG. 28B. Further, as illustrated in FIG. 34C, the three-dimensional display control unit 212 changes the viewpoint of the three-dimensional images in the other row (display area 612-2) different from the row of the target three-dimensional image, in a similar manner to the target three-dimensional image. In other words, as illustrated in FIG. 28C, the three-dimensional display control unit 212 changes the viewpoint of the three-dimensional images of the brain as displayed in the display area 612-2 on the right side of the brain as illustrated in FIG. 28A, so as to display the three-dimensional images of the brain viewed from a front side. If the processing capability is well above the actual load, the processes in FIG. 28A to FIG. 28C may be performed at high speed, as if the viewpoints of all the images of the brain appear to change at the same time. On the other hand, if the processing capability is poor, the viewpoints of the other images may be changed when the change in viewpoint is determined (i.e., the timing at which the user releases a key of the mouse when the viewpoint is changed, for example, by rotating the image of the brain by dragging operation) after only the viewpoint of the image that is moved by the user is changed. In so doing, the respective viewpoints of the heat maps that are superimposed on the images of the brain are also changed in a similar manner. Due to this configuration, the changes that are made in the viewpoint of a specific three-dimensional image (i.e., the target three-dimensional image) are automatically reflected in the other three-dimensional images in the same row and the other rows. Accordingly, the operability or efficiency improves, and the changes in activity among the images of the brain that are temporally close to each other can easily be checked.

Furthermore, cases are described in which, when the viewpoint of a specific three-dimensional images is changed, the viewpoint of the other three-dimensional images in the same row is changed in a similar manner and the viewpoint of the three-dimensional images in the other row is changed in a corresponding manner. More specifically, the viewpoint is changed to be symmetrical to the center plane of the brain (symmetry plane). As illustrated in FIG. 36A, it is assumed that the analyst has performed an operation on the three-dimensional view 612 displayed in two rows to change the viewpoint of the target three-dimensional image at the right end from among the multiple three-dimensional images of the brain as displayed in the display area 612-1. In such a case, as illustrated in FIG. 36B, as manipulated by the analyst, the three-dimensional display control unit 212 changes the viewpoint of the target three-dimensional images with the viewpoint from the left side of the brain, so as to display the three-dimensional images of the brain viewed from a left-frontal side. Then, as illustrated in FIG. 36C, the three-dimensional display control unit 212 changes the viewpoint of the other three-dimensional images of the brain in the same row as the target three-dimensional images (in the display area 612-1) in a similar manner to the target three-dimensional image. In other words, the three-dimensional display control unit 212 changes the viewpoint of the other three-dimensional images of the brain as displayed in the display area 612-1 on the left side of the brain as illustrated in FIG. 37A so as to display the three-dimensional images of the brain viewed from a left-frontal side, as illustrated in FIG. 37B. Further, as illustrated in FIG. 36C, the three-dimensional display control unit 212 changes the viewpoint of the three-dimensional images in the other row (display area 612-2) different from the row of the target three-dimensional image, in a corresponding manner to the target three-dimensional image. In other words, the three-dimensional display control unit 212 changes the viewpoint of the three-dimensional images of the brain as displayed in the display area 612-2 on the right side of the brain as illustrated in FIG. 37A to be symmetrical to the center plane of the brain (symmetry plane) as illustrated in FIG. 37C. In other words, the three-dimensional display control unit 212 changes the viewpoint so as to display the three-dimensional images of the brain viewed from a right-frontal side of the brain. In so doing, the respective viewpoints of the heat maps that are superimposed on the images of the brain are also changed in a similar manner. Due to this configuration, the changes that are made in the viewpoint of a specific three-dimensional image (i.e., the target three-dimensional image) are automatically reflected in the other three-dimensional images in the same row. Moreover, corresponding changes in viewpoint are reflected in the three-dimensional images in the other rows. Accordingly, the operability or efficiency improves. Furthermore, the images of the brain in multiple rows can be compared with each other, and thus the changes in activity among the images of the brain that are viewed from a corresponding viewpoint and are temporally close to each other can be checked.

Any one of the three methods of reflecting changes in other three-dimensional images as described above may be adopted, or which one of these methods is to be adopted to reflect changes may be switched by editing the settings.

As described above with reference to FIG. 33A to FIG. 37C, the first target three-dimensional image that is to be manipulated by the analyst to change its viewpoint in the present embodiment is the three-dimensional image at the right end of the display area 612-1. However, no limitation is intended thereby, and any one of the three-dimensional images in the display area 612-1 or the display area 612-2 may be operated. A group of three-dimensional images included in the display area 612-1 and a group of three-dimensional images included in the display area 612-2 correspond to shape images and third images according to the present embodiment, respectively.

In the above description, the viewpoint of a specific three-dimensional image of the brain in the three-dimensional view 612 is changed, and operations in which such a change in viewpoint is reflected in other three-dimensional images are described. However, no limitation is indicated thereby, and the display mode that is to be changed for a three-dimensional image is not limited to viewpoint. For example, the display mode that is to be changed for a three-dimensional image may be, for example, changes in size, changes in brightness, or changes in transparency. Such changes may be reflected in other three-dimensional images without departing from the spirit or scope of the disclosure of the above changes in viewpoint.

After some changes are made on the three-dimensional images in the three-dimensional view 612 as described above, as illustrated in FIG. 38, the analyst may operate the input unit 208 to add a memo (for example, a comment 635 as depicted in FIG. 38) onto a specific three-dimensional image. Due to such a configuration, comments on an active site of the brain that the analyst (for example, a doctor) is concerned about can be recorded in association with the relevant three-dimensional image, and can be applied to, for example, neurosurgery or a conference on such disorder of the brain.

Basic display operation of the three-view head image 613 on the time-frequency analysis screen 601 is described below with reference to FIG. 39 to FIG. 45D.

Figure 39:
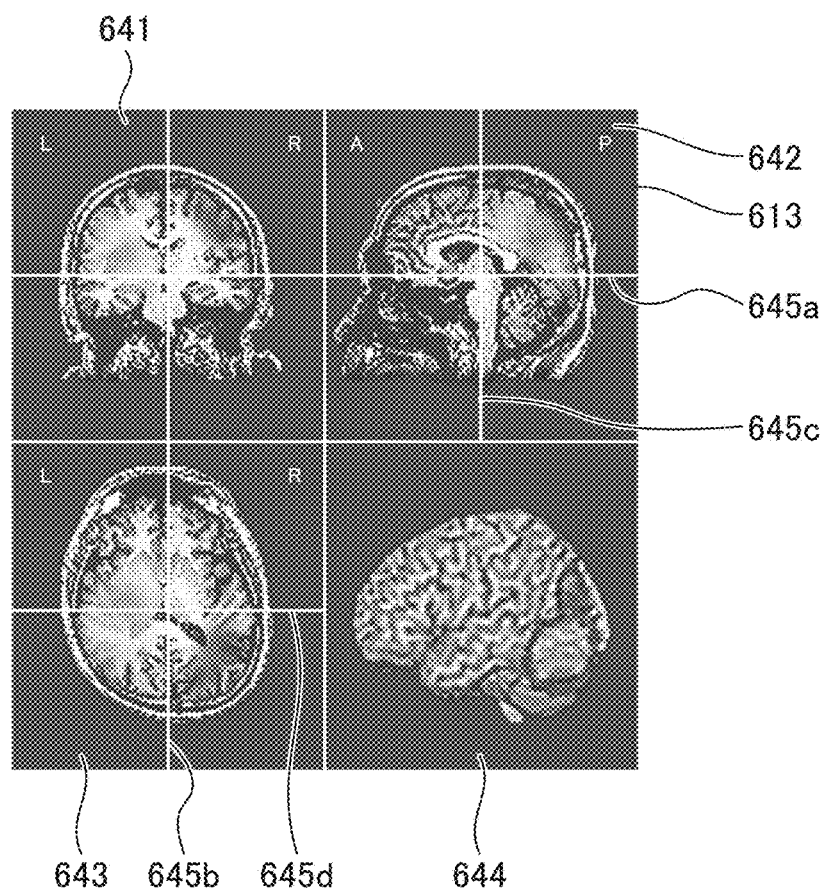
FIG. 39 is a diagram illustrating a three-view head image on a time-frequency analysis screen, according to embodiments of the present disclosure.

FIG. 39 is a diagram illustrating the three-view head image 613 on the time-frequency analysis screen 601, according to the present embodiment.

Figure 40:
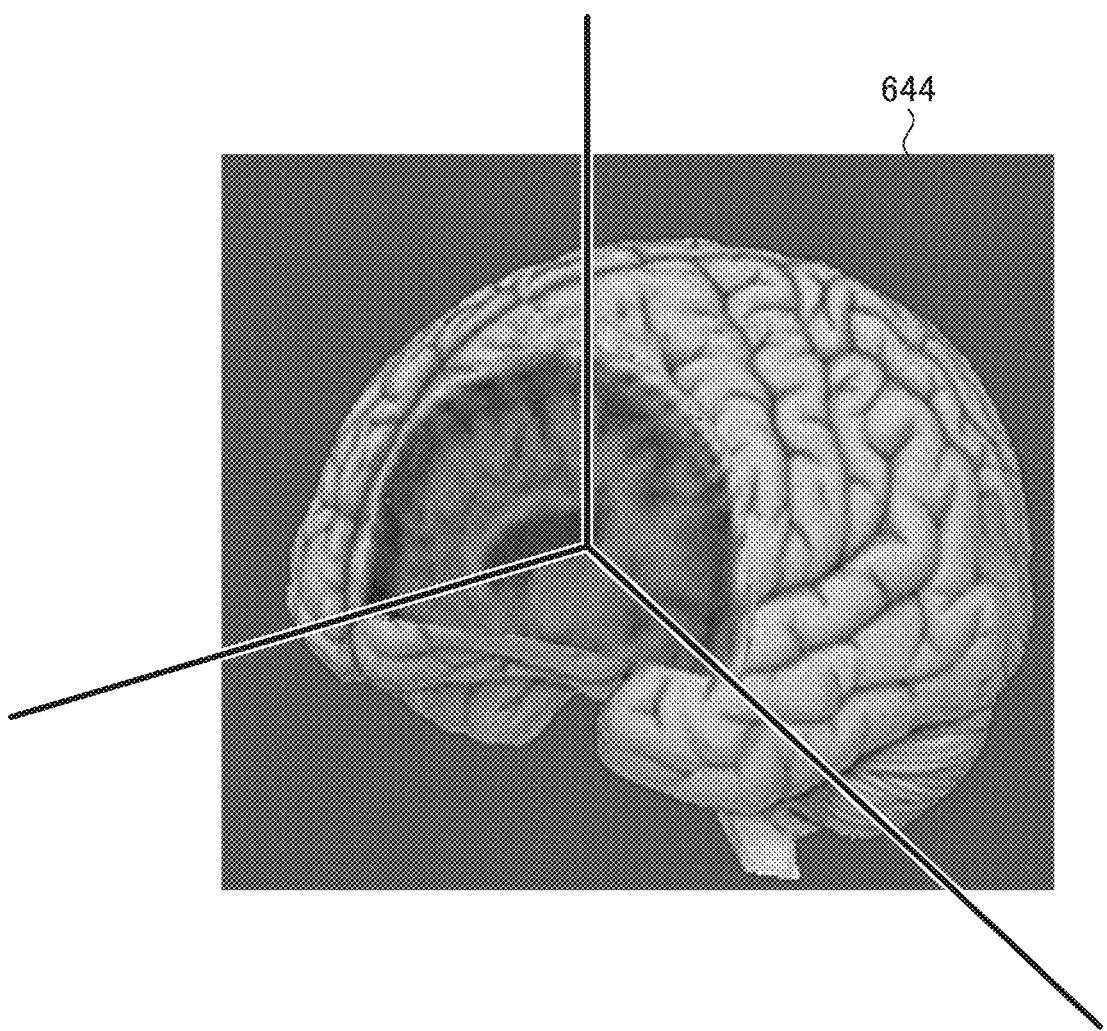
FIG. 40 is a diagram illustrating a cut model that is displayed as a three-dimensional image on a three-view head image, according to embodiments of the present disclosure.

FIG. 40 is a diagram illustrating a cut model that is displayed as a three-dimensional image on the three-view head image 613, according to the present embodiment.

Figure 41:
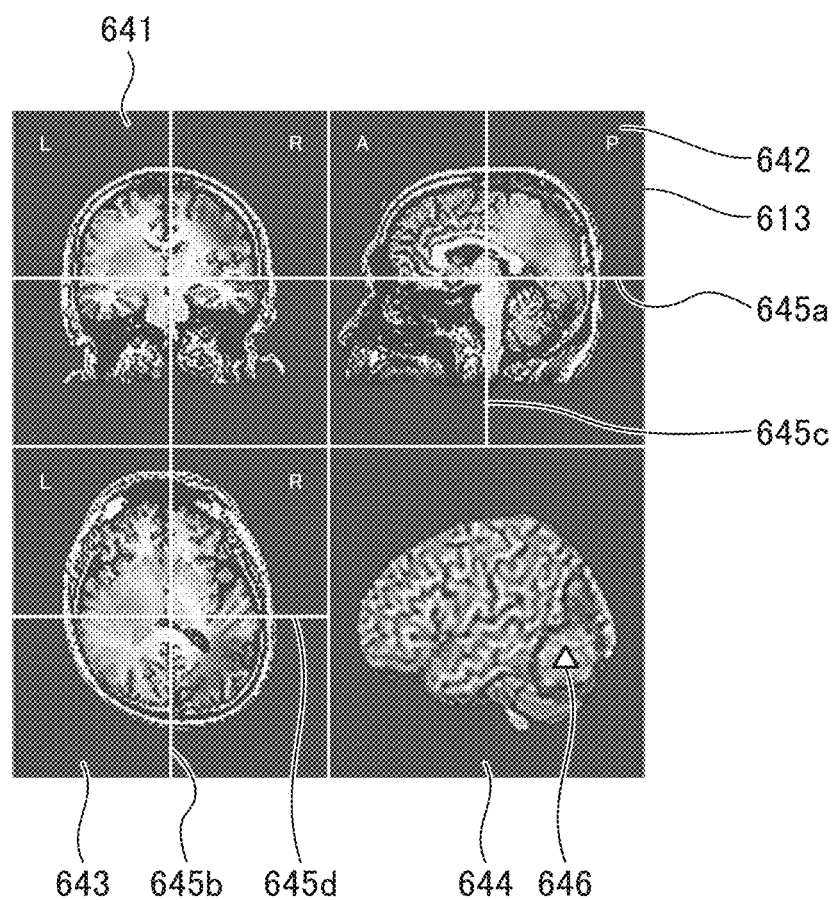
FIG. 41 is a diagram illustrating the peak selected from a peak list in a three-view head image, according to embodiments of the present disclosure.

FIG. 41 is a diagram illustrating the peak selected from the peak list 614 in the three-view head image 613, according to the present embodiment.

Figure 42:
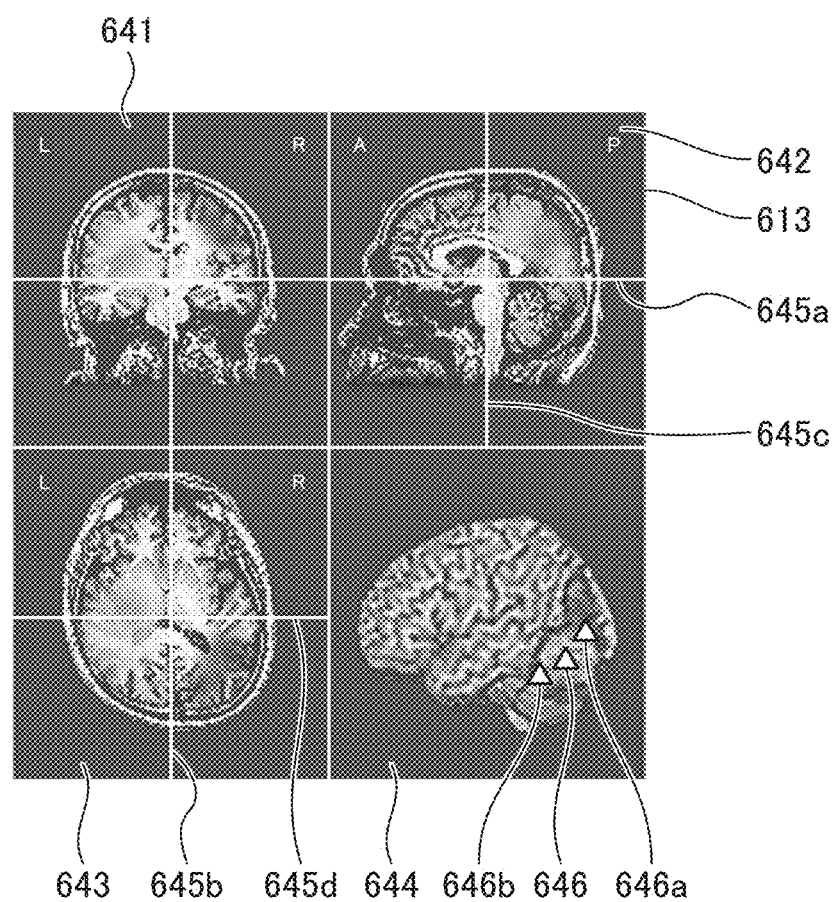
FIG. 42 is a diagram illustrating the peak selected from a peak list and the peaks that are temporally close to each other around the selected peak, in a three-view head image, according to embodiments of the present disclosure.

FIG. 42 is a diagram illustrating the peak selected from the peak list 614 and the peaks that are temporally close to each other around the selected peak, in the three-view head image 613, according to the present embodiment.

Figure 43:
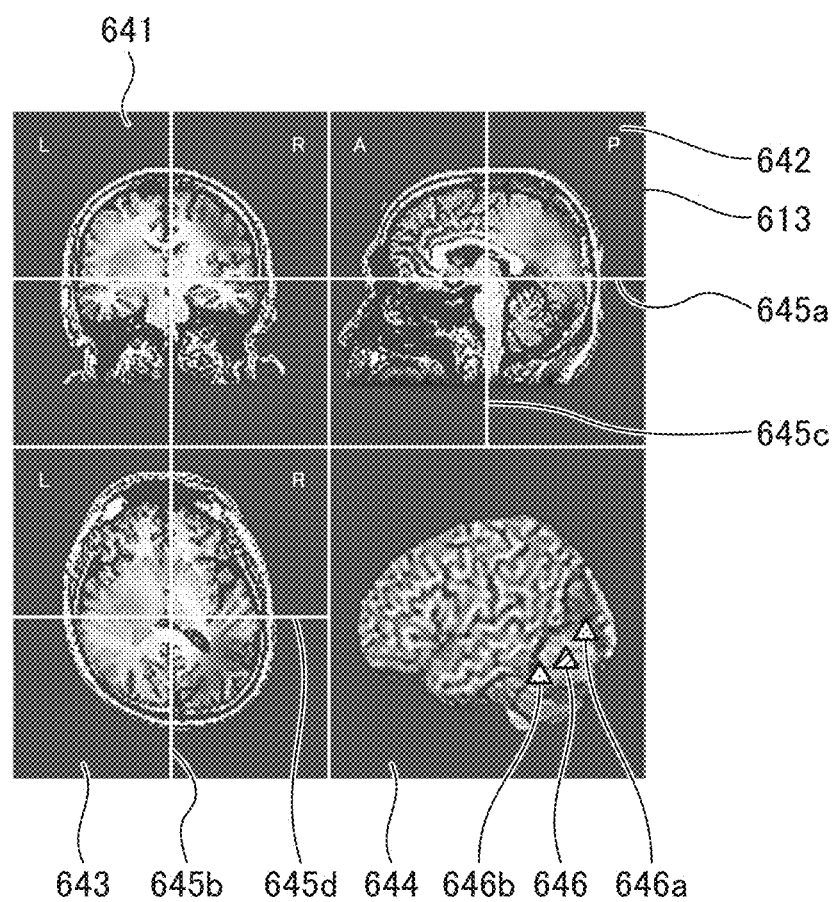
FIG. 43 is a diagram illustrating a state in which the peak selected from a peak list and the peaks that are temporally close to each other around the selected peak are indicated with varying colors, in a three-view head image, according to embodiments of the present disclosure.

FIG. 43 is a diagram illustrating a state in which the peak selected from the peak list 614 and the peaks that are temporally close to each other around the selected peak are indicated with varying colors, in the three-view head image 613, according to the present embodiment.

Figure 44:
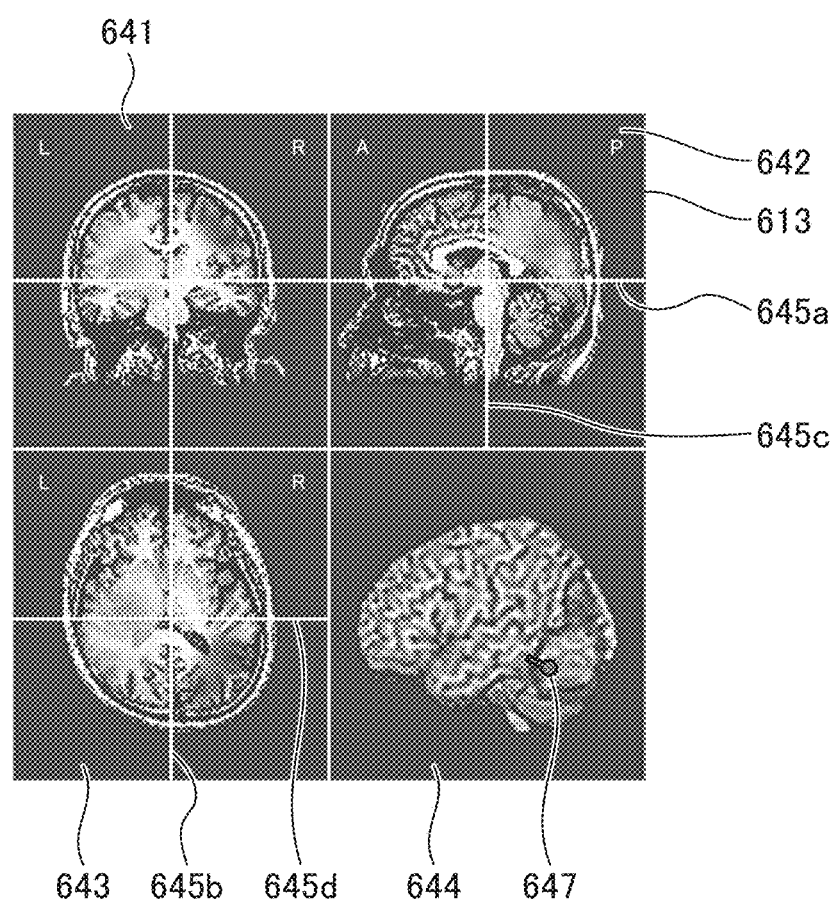
FIG. 44 is a diagram illustrating a state in which a result of dipole estimation is superimposed on the three-dimensional images on a three-view head image, according to embodiments of the present disclosure.

FIG. 44 is a diagram illustrating a state in which a result of dipole estimation is superimposed on the three-dimensional image 644 of the three-view head image 613, according to the present embodiment.

FIG. 45A, FIG. 45B, FIG. 45C, and FIG. 45D are diagrams each illustrating a state in which a result of measuring a plurality of objects (heat map) is superimposed on the three-dimensional image 644 of the three-view head image 613, according to the present embodiment.

As illustrated in FIG. 39, the three-view head image 613 includes the three-dimensional image 644 and three sectional views viewed from a desired point of the brain from three directions (such three sectional views may be collectively referred to as a three-view image in the following description). In the example as illustrated in FIG. 39, the three-view head image 613 includes a sectional view 641 orthogonal to the forward and backward directions of the brain, a sectional view 642 orthogonal to the right and left directions of the brain, and a sectional view 643 orthogonal to the up-and-down directions of the brain as the three sectional views viewed from a desired point of the brain in three directions. In the sectional view 641, a reference line 645*a* and a reference line 645*b* that pass through the above-desired point are drawn. In the sectional view 642, the reference line 645*a* and a reference line 645*c* that pass through the above-desired point are drawn. In the sectional view 643, the reference line 645*b* and a reference line 645*d* that pass through the above-desired point are drawn. A heat map that indicates the distribution of the signal strength of the biomedical signal of the time and frequency that correspond to the position (point or area) designated on the heat map 611, which is different from the heat map 611, is superimposed on each one of the sectional views 641 to 643. The display operation on the three-view head image 613 is controlled by the sectional-view control unit 213.

The reference line 645*a* defines the position in the up-and-down directions with reference to the above-desired point of the brain, and thus is drawn as a continuous line across the sectional view 641 and the sectional view 642. The reference line 645*b* defines the position in the right and left directions with reference to the above-desired point of the brain, and thus is drawn as a continuous line across the sectional view 641 and the sectional view 643. On the sectional view 642, the reference line 645*c* defines the position in the forward and backward directions with reference to the above-desired point of the brain. On the sectional view 643, the reference line 645*d* defines the position in the forward and backward directions with reference to the above-desired point of the brain. The sectional views 641 to 643 in the three-view head image 613 are arranged as above as illustrated in FIG. 39 because the reference line 645*a* and the reference line 645*b* can be drawn in a continuous manner across a plurality of sectional views. However, no limitation is intended thereby, and the sectional views 641 to 643 may be arranged in any desired manner. In such a configuration, a reference line that passing through a desired point of the brain may be drawn in each one of the sectional views. Alternatively, no reference line may be drawn in the sectional views. In such a configuration, for example, a mark that indicates the desired point of the brain may be displayed on each one of the sectional views.

The three-dimensional image 644 is a three-dimensional image of the brain, and as will be described later, the viewpoints of the three-dimensional images of the brain that are drawn in the three-dimensional view 612 are changed in accordance with the operation made to the three-dimensional image 644. A heat map that indicates the distribution of the signal strength of the biomedical signal of the time and frequency that correspond to the position (point or area) designated on the heat map 611, which is different from the heat map 611, is superimposed on the three-dimensional image 644. Note also that the function of the three-dimensional image 644 is not limited to display a three-dimensional image of the brain viewed from a desired point of the brain. For example, as illustrated in FIG. 40, the three-dimensional image 644 may be a cut-model image obtained by extracting a partial image of the brain in three-dimensional directions around the position of the brain specified in the three-view image 613.

The peak that is selected from among the peaks registered in the peak list 614 is identified on the three-view head image 613 as illustrated in FIG. 39, and as illustrated in FIG. 41, a peak point 646 that indicates the above-selected peak may be displayed on the three-dimensional image 644. For example, the top N peak positions with reference to the peak selected from the peak list 614 may be displayed on the three-dimensional image 644. FIG. 42 is a diagram illustrating an example in which the positions of the top three peaks (i.e., the peak points 646, 646*a*, and 646*b*) are indicated, according to the present embodiment. Alternatively, the peaks at times before and after the peak selected from the peak list 614 may be displayed in FIG. 42 as the peak points 646, 646*a*, and 646*b* in place of the above top three peaks. In other words, the track of the peaks may be displayed. How the peak positions are to be indicated may be determined based on the settings. For example, in addition to or in place of the above setting, the settings may be switched between the setting in which no peak is to be indicated or the setting in which peaks whose signal strength is equal to or higher than M are indicated.

As illustrated in FIG. 43, the display mode of the multiple peaks displayed on the three-dimensional image 644 may be changed according to the attribute information of those peaks. FIG. 43 is a diagram illustrating an example in which the colors of the indicated peaks are changed so as to be different from each other, according to the present embodiment.

As illustrated in FIG. 44, the sectional-view control unit 213 may control the display to superimpose a dipole 647 that is obtained as a result of dipole estimation on the three-dimensional image 644, in, for example, a different analyzing screen. Due to such a configuration, the relative positions of the heat map on the three-dimensional image 644 that indicates sites to be conserved and the dipole that indicates the affected sites (target sites) can be figured out, and such information can be used for, for example, surgery.

On one of the sectional views of the three-view head image 613, a desired point of the brain in the three-dimensional space can be specified by a clicking or tapping operation performed on the input unit 208 by the analyst. Once a particular position is specified on the three-view images as described above, the distribution of the signal strength of the biomedical signals of the time and frequency corresponding to the specified position is reflected in the heat map 611.

On one of the sectional views of the three-view head image 613, a specific area of the brain in the three-dimensional space can be designated by a dragging operation or swiping operation made by the analyst to the input unit 208. Once a desired area is specified on the three-view images as described above, the distribution of the average signal strength of the biomedical signals of the time and frequency corresponding to the specified area is reflected in the heat map 611.

Figure 45D:
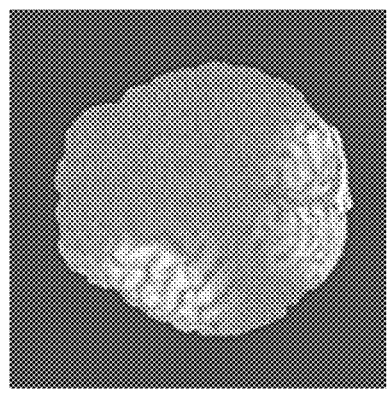
FIG. 45A, FIG. 45B, FIG. 45C, and FIG. 45D are diagrams each illustrating a state in which a result of measuring a plurality of objects (heat map) is superimposed on the three-dimensional images of a three-view head image, according to embodiments of the present disclosure.
Figure 45C:
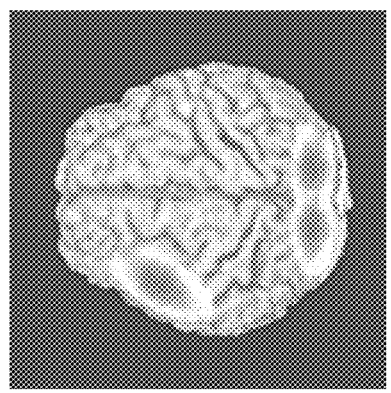
Figure 45B:
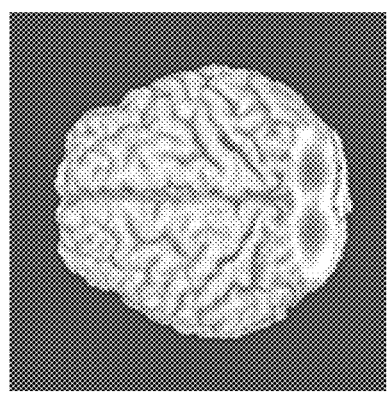
Figure 45A:
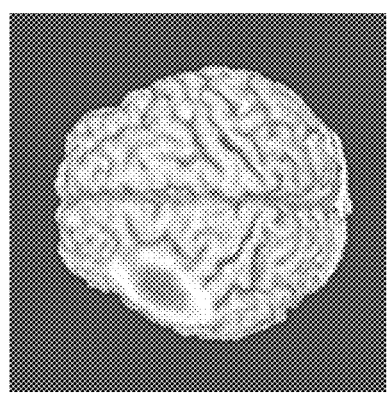

In the heat map that is drawn on the three-dimensional image 644 (and the three-view images), which is a contour map that indicates the differences in signal strength, results of stimulation such as activation at varying sites of the brain may be superimposed on top of one another. For example, after a result of performing language stimulation during the measurement and a result of performing visual stimulation during the measurement are obtained, as illustrated in FIG. 45C, the sectional-view control unit 213 may superimpose a heat map where the language area is activated as illustrated in FIG. 45A and a heat map where the visual area is activated as illustrated in FIG. 45B on top of one another. Due to such a configuration as above, it becomes identifiable as illustrated in FIG. 45C that the sites indicated on the heat map where superimposition has been performed are sites to be conserved. Such superimposition may be implemented as follows. Assuming that the currently-displayed result of measurement indicates the language area, it may be configured such that a different result of measurement (for example, the result of measurement indicating the visual area) is selectable from a menu. When superimposition is to be performed, the reaction time to the stimulation may vary depending on the object. In view of such circumstances, if the time lag is configurable when an object is added, superimposition can be performed more precisely. Further, the three-dimensional image as illustrated in FIG. 45C, which is obtained as a result of superimposing a heat map on a three-dimensional image of the brain, may be highlighted in an inverse manner as illustrated in FIG. 45D. Due to this configuration, a removable site, which is not among the sites to be conserved, can be indicated in the reversed manner.

In the present embodiment, the sectional view in the three-view head image 613 includes three cross sections taken from three different directions. However, no limitation is intended thereby, and the sectional view in the three-view head image 613 may be a single cross section taken from one specific direction or two or four or more cross sections taken from different directions.

Figure 46:
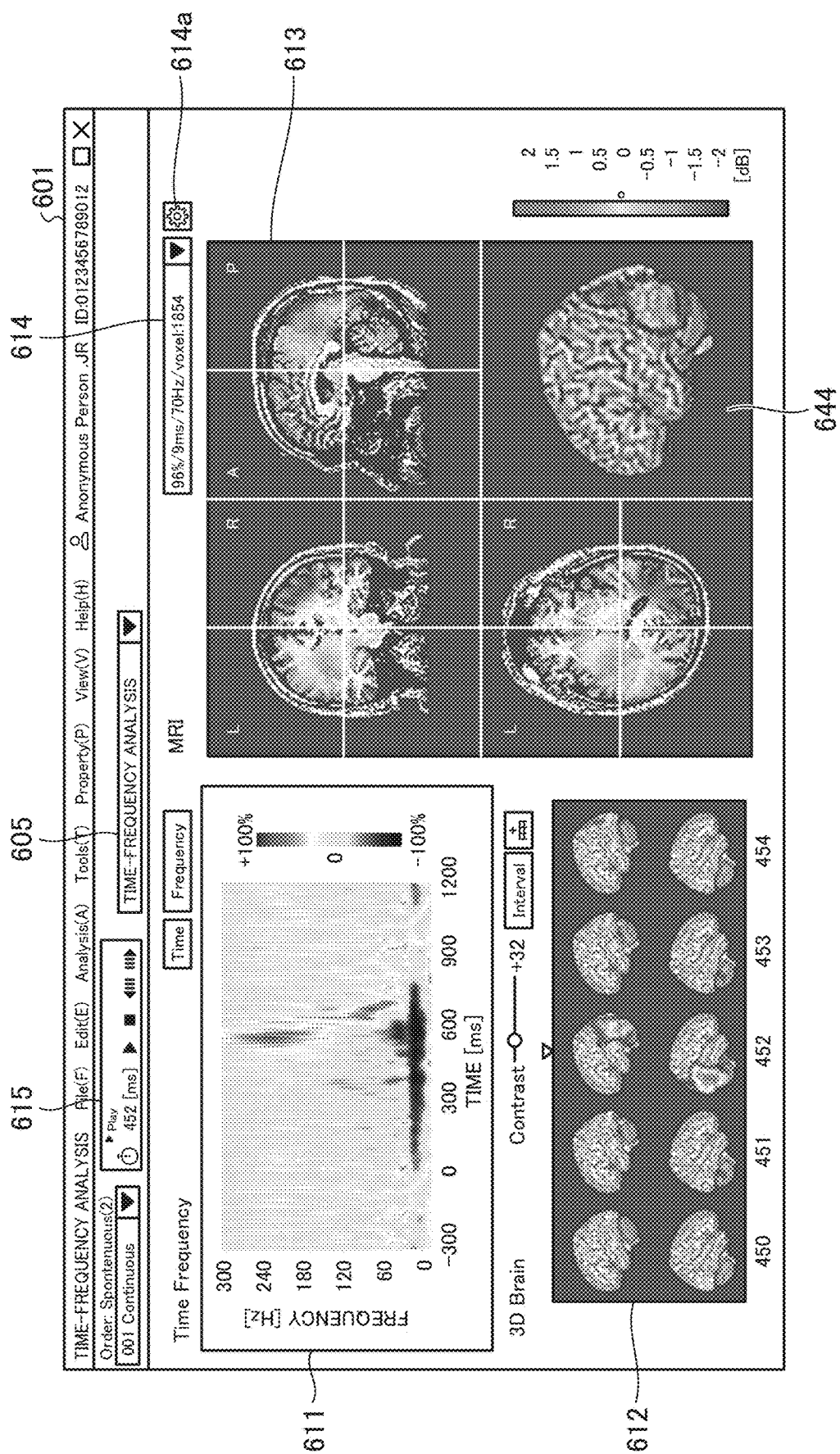
FIG. 46 is a diagram illustrating a state before the viewpoint is changed for the three-dimensional images in a three-view head image, according to embodiments of the present disclosure.
Figure 47:
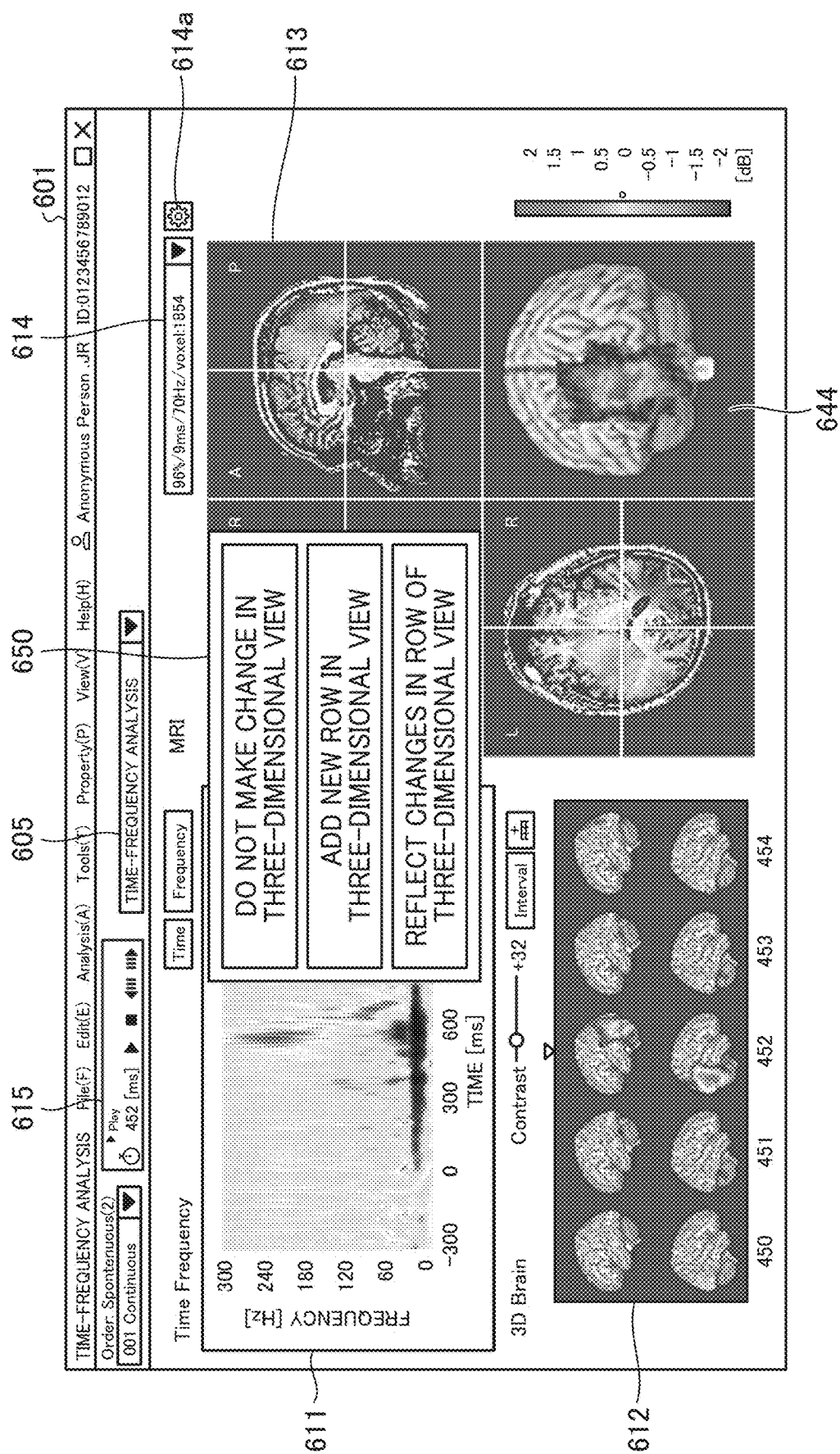
FIG. 47 is a diagram illustrating a dialog box displayed when the viewpoint of the three-dimensional images in a three-view head image is changed, according to embodiments of the present disclosure.
Figure 48:
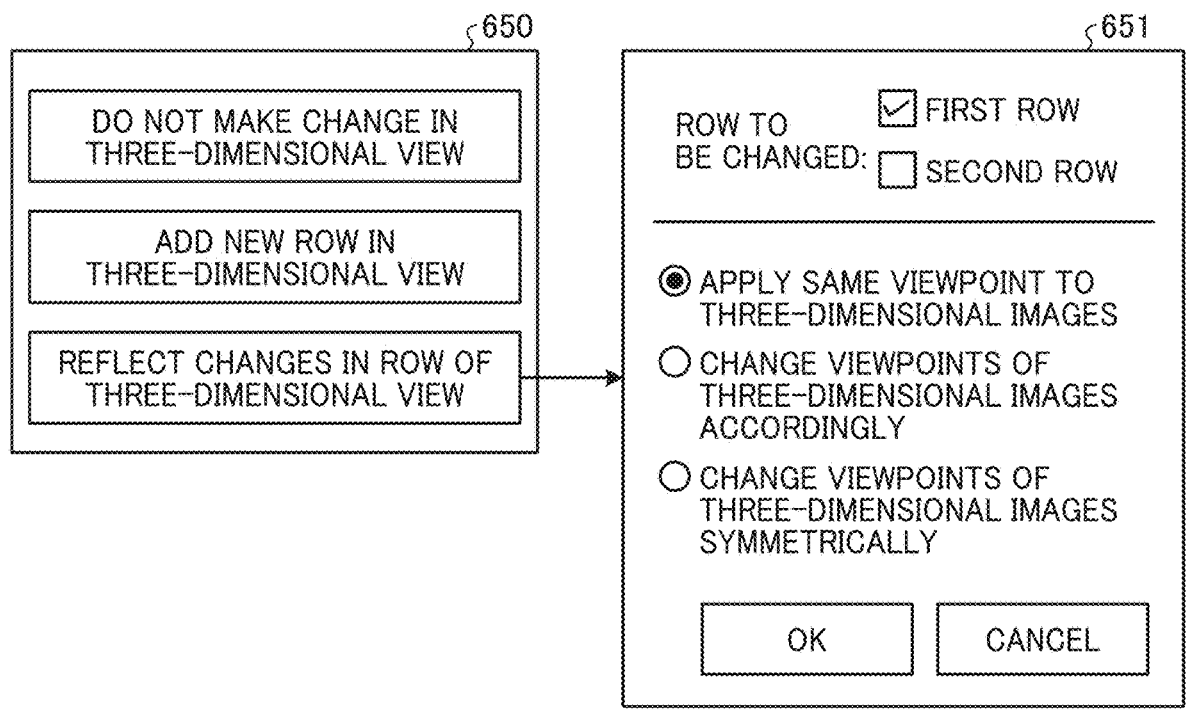
FIG. 48 is a diagram illustrating a setting in which the changes in viewpoint made on a three-dimensional image are applied to the viewpoint of the three-dimensional images in the first row of three-dimensional view, according to embodiments of the present disclosure.

With reference to FIG. 46 to FIG. 48, operations in the time-frequency analysis screen 601 are described in which the changes in viewpoint made on the three-dimensional image 644 of the three-view head image 613 are reflected in the three-dimensional images of the three-dimensional view 612.

FIG. 46 is a diagram illustrating a state before the viewpoint is changed for the three-dimensional image 644 of the three-view head image 613, according to the present embodiment.

FIG. 47 is a diagram illustrating a dialog box displayed when the viewpoint of the three-dimensional image 644 of the three-view head image 613 is changed, according to the present embodiment.

FIG. 48 is a diagram illustrating a setting in which the changes in viewpoint made on the three-dimensional image 644 are applied to the viewpoint of the three-dimensional images in the first row of the three-dimensional view 612, according to the present embodiment.

Figure 49:
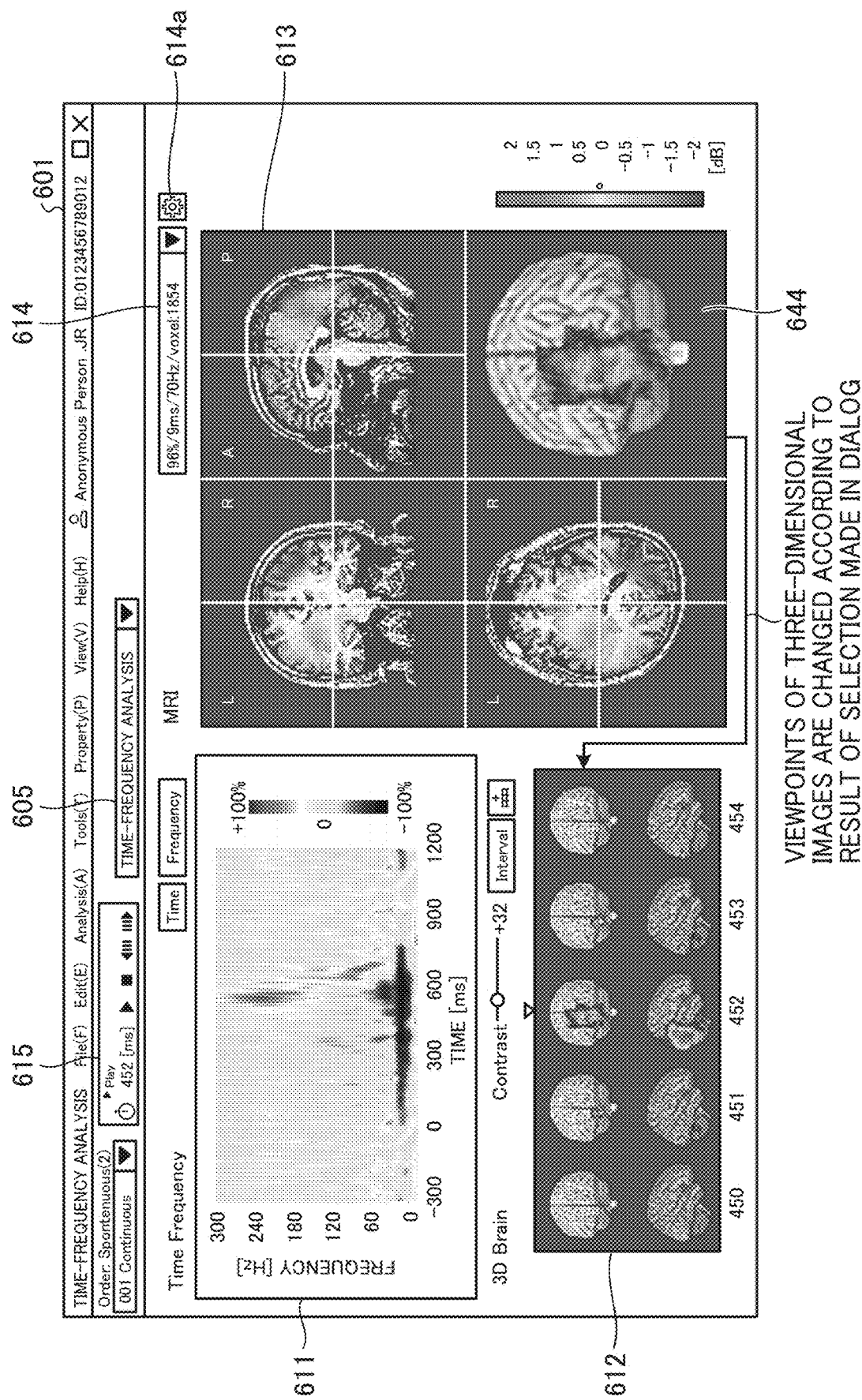
FIG. 49 is a diagram illustrating a state in which the changes in viewpoint of a three-dimensional image in a three-view head image are applied to the viewpoint of the three-dimensional images in the first row of three-dimensional view, according to embodiments of the present disclosure.

FIG. 49 is a diagram illustrating a state in which the changes in viewpoint of the three-dimensional image 644 in the three-view head image 613 are applied to the viewpoint of the three-dimensional images in the first row of the three-dimensional view 612, according to the present embodiment.

Figure 50:
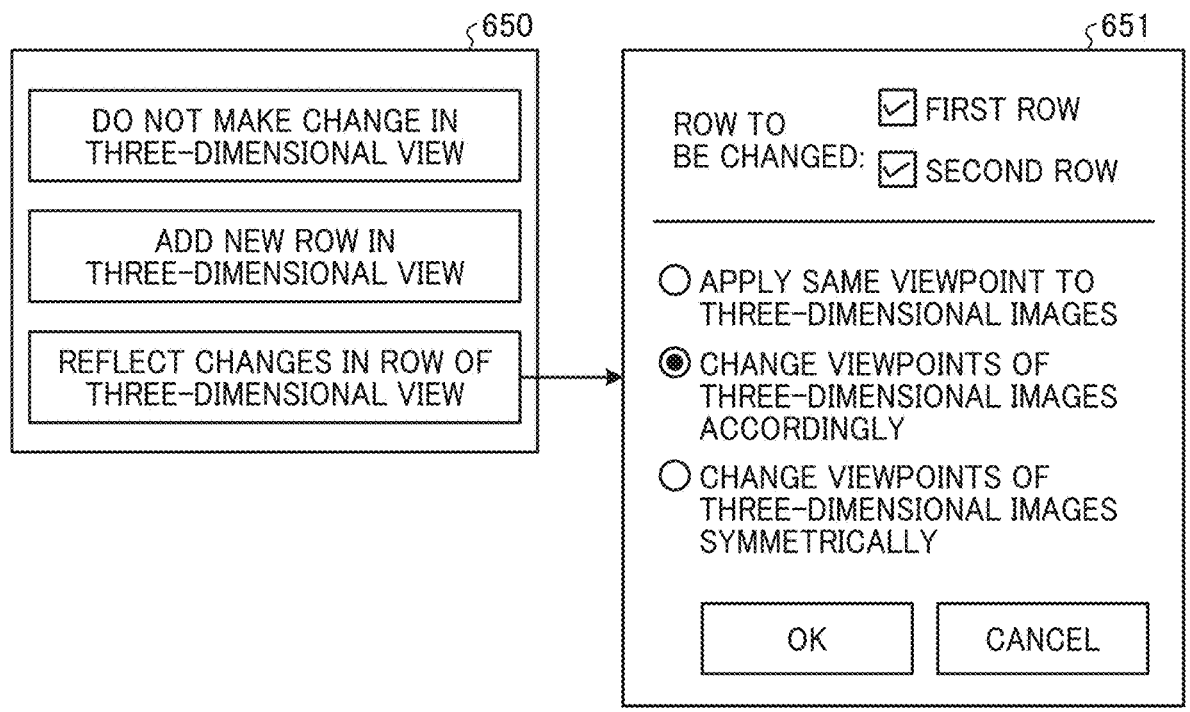
FIG. 50 is a diagram illustrating a setting in which the changes in viewpoint made on a three-dimensional image are reflected in the three-dimensional images in the first and second rows of three-dimensional view, according to embodiments of the present disclosure.

FIG. 50 is a diagram illustrating a setting in which the changes in viewpoint made on the three-dimensional image 644 are reflected in the three-dimensional images in the first and second rows of the three-dimensional view 612, according to the present embodiment.

Figure 51:
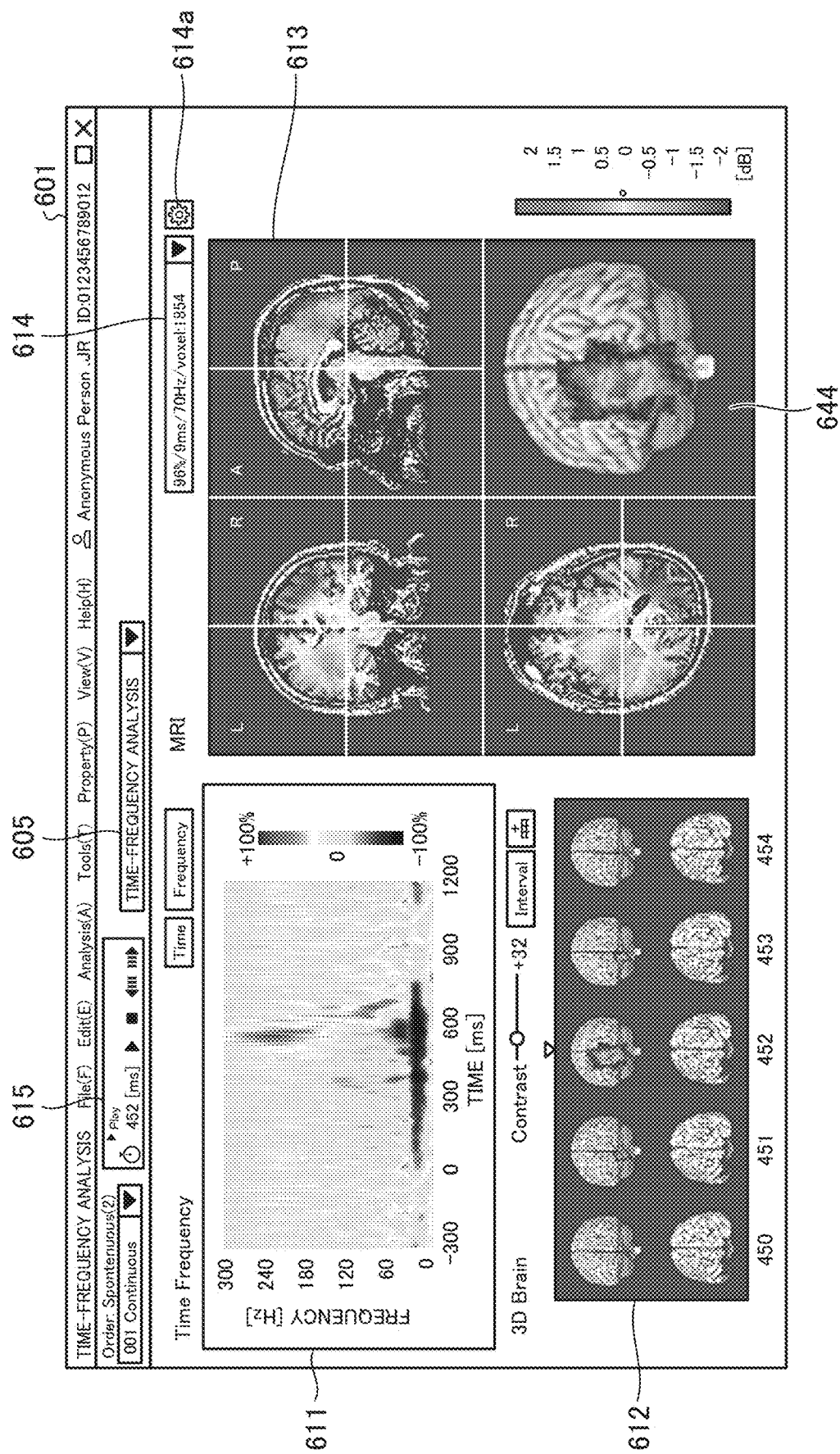
FIG. 51 is a diagram illustrating a state in which the changes in the viewpoint of a three-dimensional image of a three-view head image are reflected in the first and second rows of three-dimensional view, according to embodiments of the present disclosure.

FIG. 51 is a diagram illustrating a state in which the changes in the viewpoint of the three-dimensional image 644 of the three-view head image 613 are reflected in the first and second rows of the three-dimensional view 612, according to the present embodiment.

Figure 52:
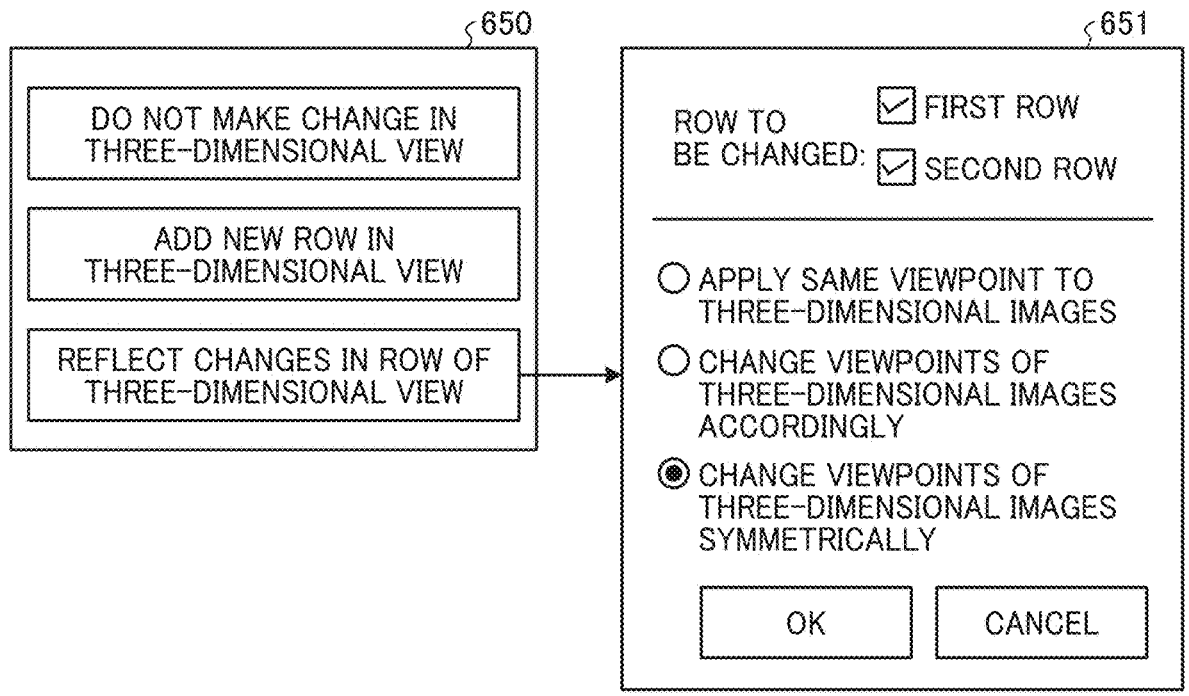
FIG. 52 is a diagram illustrating a setting in which the changes in viewpoint made on a three-dimensional image are symmetrically reflected in the three-dimensional images in the first and second rows of three-dimensional view, according to embodiments of the present disclosure.

FIG. 52 is a diagram illustrating a setting in which the changes in viewpoint made on the three-dimensional image 644 are symmetrically reflected in the three-dimensional images in the first and second rows of the three-dimensional view 612, according to the present embodiment.

FIG. 46 is a diagram illustrating a state in which the changes in the viewpoint of the three-dimensional image 644 of the three-view head image 613 are symmetrically reflected in the three-dimensional images in the first and second rows of the three-dimensional view 612, according to the present embodiment.

FIG. 47 is a diagram illustrating a setting in which new three-dimensional images in which the changes in viewpoint made on the three-dimensional image 644 are reflected are added to the three-dimensional view 612 in a separate row, according to the present embodiment.

FIG. 48 is a diagram illustrating a state in which new three-dimensional images in which the changes in viewpoint made on the three-dimensional image 644 of the three-view head image 613 are reflected are added to the three-dimensional view 612 in a separate row, according to the present embodiment.

In a similar manner to the three-dimensional view 612, the viewpoint of the image of the brain displayed on the three-dimensional image 644 of the three-view head image 613 can be changed as manipulated by the analyst (for example, a dragging operation or a swiping operation). In such cases, the changes in the viewpoint of the brain in the three-dimensional image 644 may be reflected in the viewpoint of the three-dimensional images of the brain displayed in the three-dimensional view 612. Some patterns of reflection methods or application methods are described below.

Once the three-dimensional image 644 of the three-view head image 613 displayed on the time-frequency analysis screen 601, as illustrated in FIG. 46, is manipulated by the analyst (for example, a dragging operation or a swiping operation), the sectional-view control unit 213 controls the display to display the dialog box 650 as illustrated in FIG. 47. The dialog box 650 appears when the viewpoint of the brain in the three-dimensional image 644 is changed, and is a window used to determine how such changes in viewpoint are to be reflected in the three-dimensional view 612. For example, when a key "Do not make changes in three-dimensional view" is clicked or tapped in the present embodiment, the viewpoint of the three-dimensional images in the three-dimensional view 612 is not changed. In the present embodiment, as illustrated in FIG. 47, it is assumed that the analyst changes the viewpoint of the three-dimensional image 644 viewed from the viewpoint on the left side of the brain so as to display the three-dimensional images of the brain viewed from a rear side.

Firstly, as illustrated in FIG. 48, a case is described in which the key "Reflect changes in row of three-dimensional view" in the dialog box 650 is clicked or tapped. In response to this operation, the sectional-view control unit 213 controls the display to display a dialog box 651 as illustrated in FIG. 48 to determine how such changes in viewpoint are to be reflected in the three-dimensional view 612. As illustrated in FIG. 48, the analyst selects the first row of the three-dimensional view 612 as the row in which changes are to be reflected and then the selects "Apply same viewpoint to three-dimensional images" in the dialog box 651. In such a case, as illustrated in FIG. 49, the three-dimensional display control unit 212 controls the display to display the three-dimensional images in the first row (upper row) of the three-dimensional view 612 to have the viewpoint same as the changed viewpoint of the three-dimensional image 644.

Next, a case is described in which, after the viewpoint is changed as illustrated in FIG. 47, the analyst clicks or taps the key "Reflect changes in row of three-dimensional view" in the dialog box 650 as illustrated in FIG. 50, and the analyst selects the first and second rows of the three-dimensional view 612 as the row in which changes are to be reflected and then selects "Change viewpoints of three-dimensional images accordingly" in the dialog box 651. In such a case, as illustrated in FIG. 51, the three-dimensional display control unit 212 controls the display to reflect the changes in viewpoint made on the three-dimensional image 644 in the three-dimensional images in the first row of the three-dimensional view 612, which originally have the same viewpoint as the three-dimensional image 644. In other words, as illustrated in FIG. 51, changes are reflected so as to display the three-dimensional images of the brain viewed from a rear side. Further, as illustrated in FIG. 51, the three-dimensional display control unit 212 controls the display to reflect the changes in viewpoint made on the three-dimensional image 644 in the three-dimensional images in the second row of the three-dimensional view 612, which originally have the viewpoint on the right side of the brain. In other words, as illustrated in FIG. 51, the viewpoint is changed so as to display the three-dimensional images of the brain viewed from a front side. Note also that the selection made in the dialog box 651 by clicking or tapping the key "Reflect changes in row of three-dimensional view" may be set to the initial state. Upon that selection, for example, a "View link" or "Release view link" key may be arranged to display the result of selection. Due to such a configuration, repetitive selecting operation can be omitted or simplified.

Figure 53:
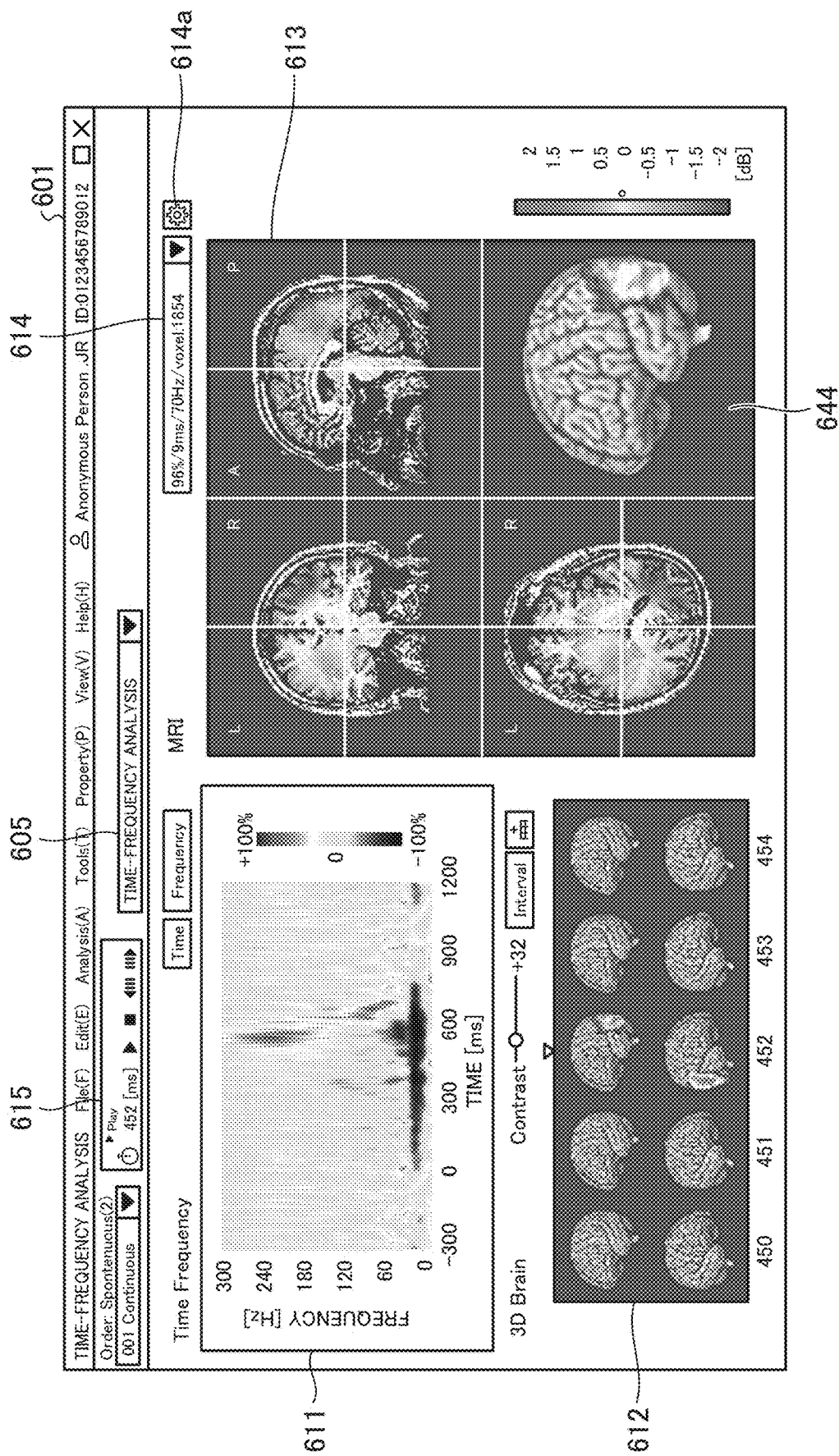
FIG. 53 is a diagram illustrating a state in which the changes in the viewpoint of a three-dimensional image of a three-view head image are symmetrically reflected in the three-dimensional images in the first and second rows of three-dimensional view, according to embodiments of the present disclosure.

Next, as illustrated in FIG. 53, a case is described in which the viewpoint of the three-dimensional image 644 viewed from the viewpoint on the left side of the brain is changed by the analyst so as to display the three-dimensional images of the brain viewed from a left-frontal side. Upon these changes, as illustrated in FIG. 52, the analyst clicks or taps the key "Reflect changes in row of three-dimensional view" in the dialog box 650, and then selects the first and second rows of the three-dimensional view 612 as the row in which changes are to be reflected and selects "Change viewpoints of three-dimensional images symmetrically" in the dialog box 651. In such a case, as illustrated in FIG. 53, the three-dimensional display control unit 212 controls the display to reflect the changes in viewpoint made on the three-dimensional image 644 in the three-dimensional images in the first row of the three-dimensional view 612, which originally have the same viewpoint as the three-dimensional image 644. In other words, as illustrated in FIG. 53, the viewpoint is changed so as to display the three-dimensional images of the brain viewed from a left-frontal side of the brain. Further, as illustrated in FIG. 53, the three-dimensional display control unit 212 controls the display to symmetrically reflect the changes in viewpoint made on the three-dimensional image 644 in the three-dimensional images in the second row of the three-dimensional view 612, which originally have the viewpoint on the right side of the brain. As illustrated in FIG. 53, the viewpoint of the three-dimensional images in the second row of the three-dimensional view 612 is changed to be symmetrical to the center plane of the brain (symmetry plane). In other words, the viewpoint of the three-dimensional images in the second row of the three-dimensional view 612 is changed so as to display the three-dimensional images of the brain viewed from a right-frontal side of the brain.

Figure 54:
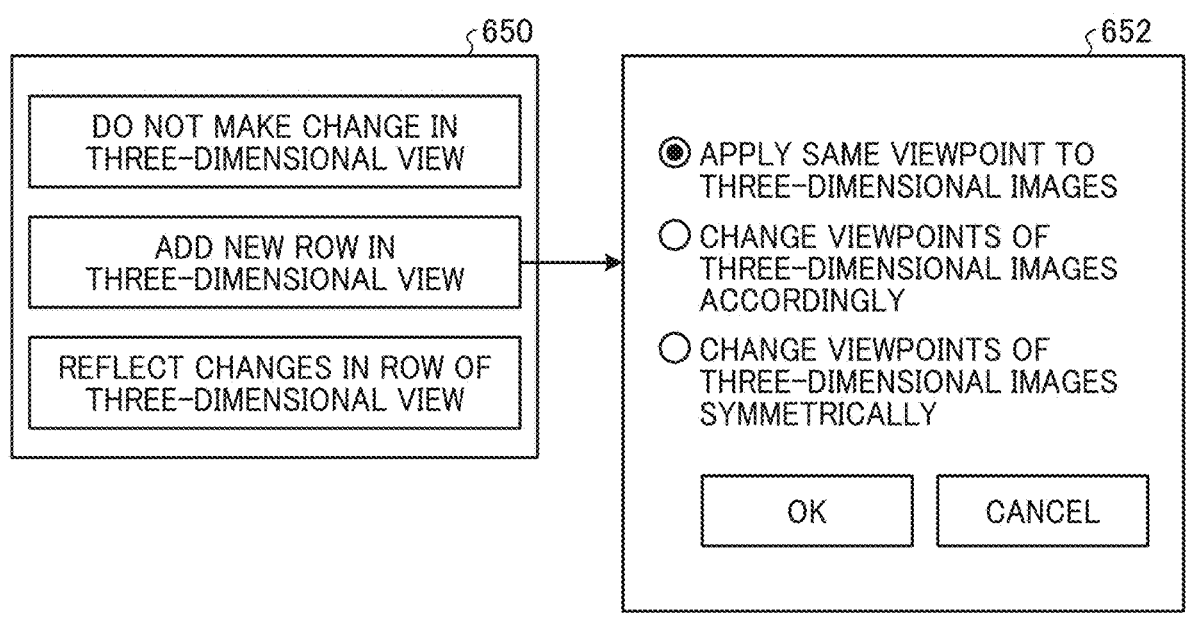
FIG. 54 is a diagram illustrating a setting in which new three-dimensional images in which the changes in viewpoint made on a three-dimensional image are reflected are added to three-dimensional view in a separate row, according to embodiments of the present disclosure.
Figure 55:
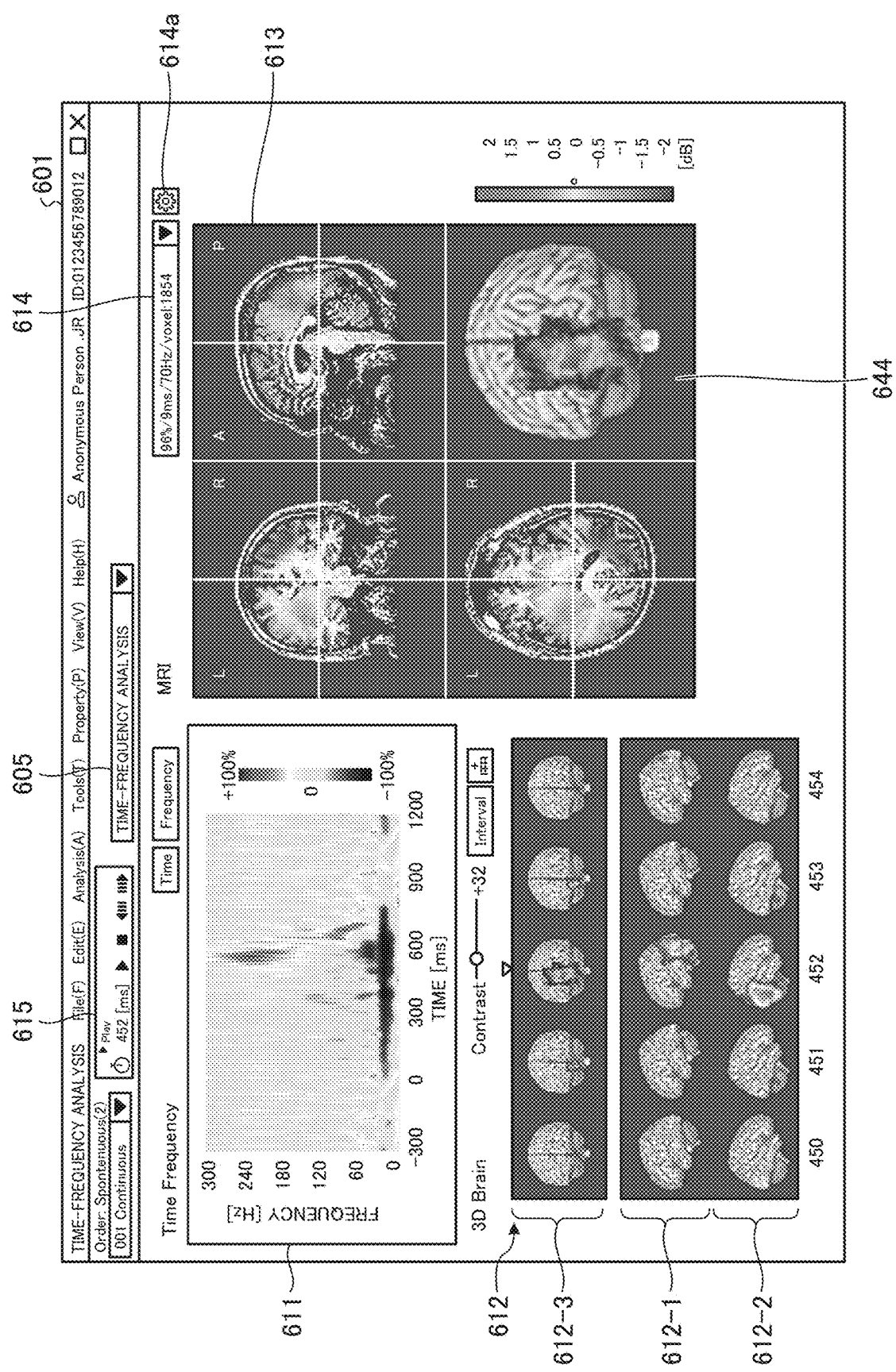
FIG. 55 is a diagram illustrating a state in which new three-dimensional images in which the changes in viewpoint made on a three-dimensional image of a three-view head image are reflected are added to three-dimensional view in a separate row, according to embodiments of the present disclosure.

Next, a case is described in which, after the viewpoint is changed as illustrated in FIG. 54, the analyst selects "Apply same viewpoint to three-dimensional images" in a dialog box 652 displayed by clicking or tapping the key "Add new row in three-dimensional view" in the dialog box 650 as illustrated in FIG. 54. In such a case, as illustrated in FIG. 55, as a result of the changes in viewpoint made on the three-dimensional image 644, the three-dimensional display control unit 212 controls the display to add the three-dimensional images of the brain with the same viewpoint as a new row in a display area 612-3 of the three-dimensional view 612. In other words, as illustrated in FIG. 55, three-dimensional images of the brain viewed from a rear side are displayed in a new row of the display area 612-3.

As described above, in accordance with the various kinds of settings, the changes in viewpoint made on the three-dimensional image 644 in the three-view head image 613 can be reflected in the viewpoint of the three-dimensional images of the brain that are arranged in the three-dimensional view 612 in a chronological order. Due to such a configuration, changes in viewpoint similar to the changes in viewpoint made on the three-dimensional image 644 do not have to be made on the three-dimensional view 612 in a repetitive manner. Due to this configuration, the operability or efficiency improves. Furthermore, the changes in the state of the brain can be checked on the three-dimensional view 612 in chronological order with the viewpoint same as the viewpoint as changed in the three-dimensional image 644 or with the viewpoint corresponding to the viewpoint as changed in the three-dimensional image 644.

The above methods of reflecting changes in viewpoint in each one of the images of the brain displayed in the three-dimensional view 612, which are set or determined in the dialog boxes 650 to 652 as illustrated in FIG. 48, FIG. 50, FIG. 52, and FIG. 54, are given by way of example, and any other ways or methods of reflection may be set or adopted.

Operations in which changes in viewpoint are reflected in the three-dimensional images of the three-dimensional view 612 when the viewpoint of the brain in the three-dimensional image 644 is changed are described as above. However, no limitation is indicated thereby, and the display mode that is to be changed for the three-dimensional image 644 is not limited to viewpoint. For example, the display mode that is to be changed for the three-dimensional image 644 may be, for example, changes in size, changes in brightness, or changes in transparency. Such changes may be reflected in the three-dimensional images of the three-dimensional view 612 without departing from the spirit or scope of the disclosure of the above changes in viewpoint.

Basic operation of the peak list 614 on the time-frequency analysis screen 601 is described below with reference to FIG. 56 to FIG. 60.

Figure 56:
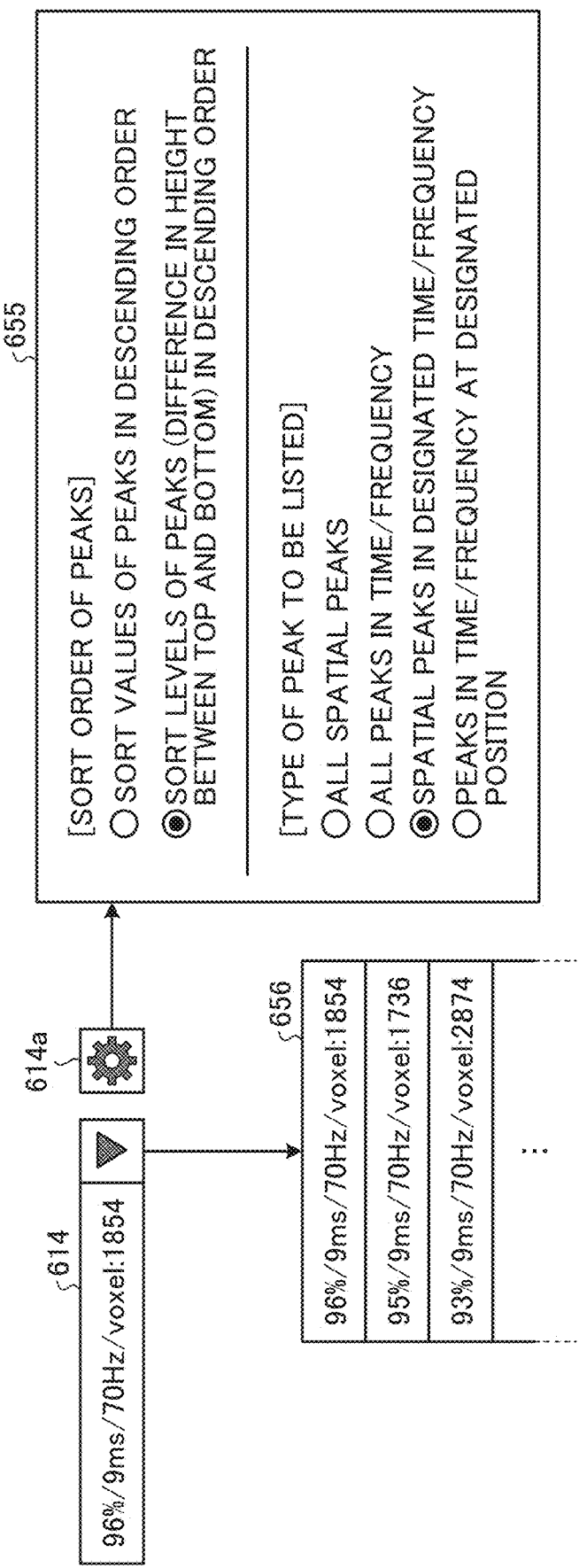
FIG. 56 is a diagram illustrating the setting of a peak list, according to embodiments of the present disclosure.

FIG. 56 is a diagram illustrating the setting of the peak list 614, according to the present embodiment.

Figure 57:
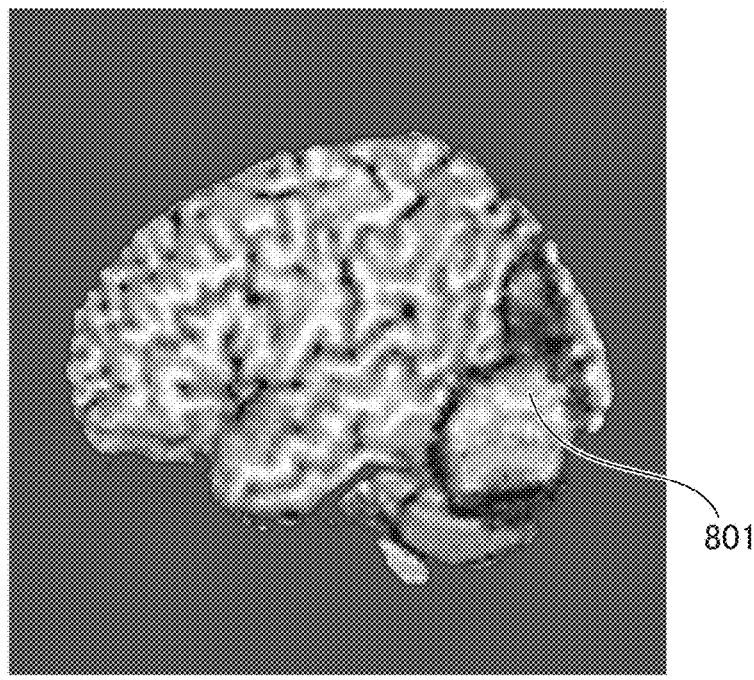
FIG. 57 is a diagram illustrating a spatial peak according to embodiments of the present disclosure.

FIG. 57 is a diagram illustrating a spatial peak according to the present embodiment.

Figure 58:
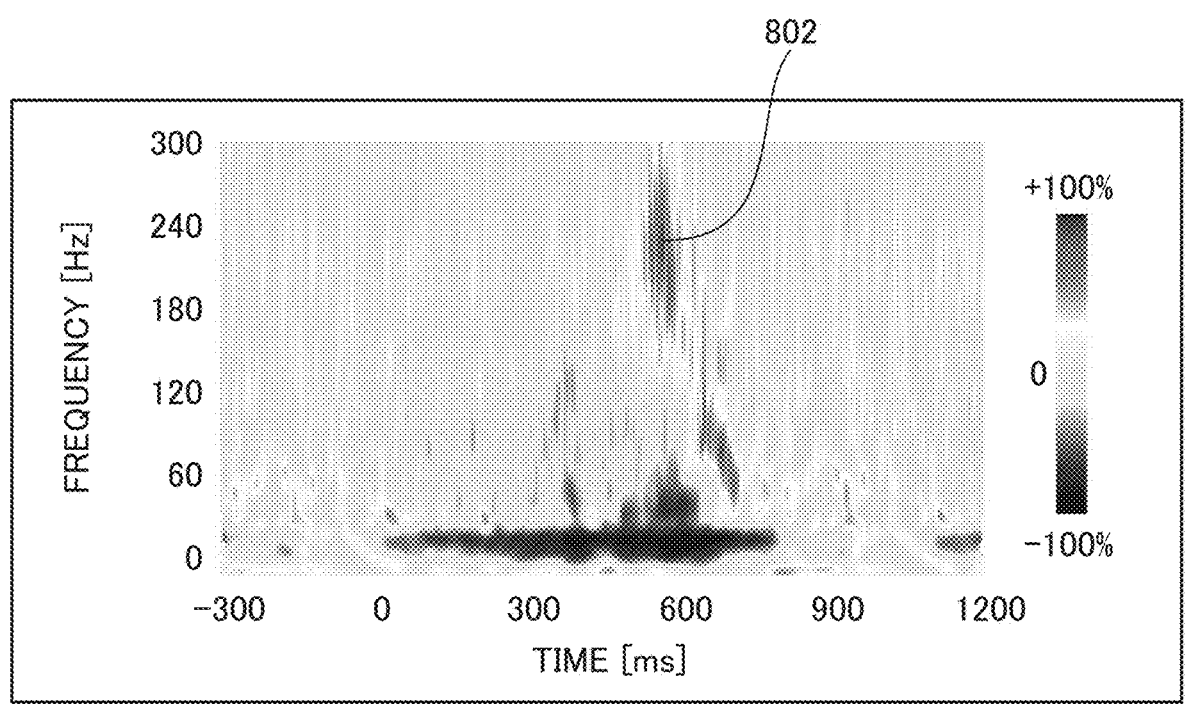
FIG. 58 is a diagram illustrating a peak in time and a peak in frequency, according to embodiments of the present disclosure.

FIG. 58 is a diagram illustrating a peak in time and a peak in frequency according to the present embodiment.

Figure 59:
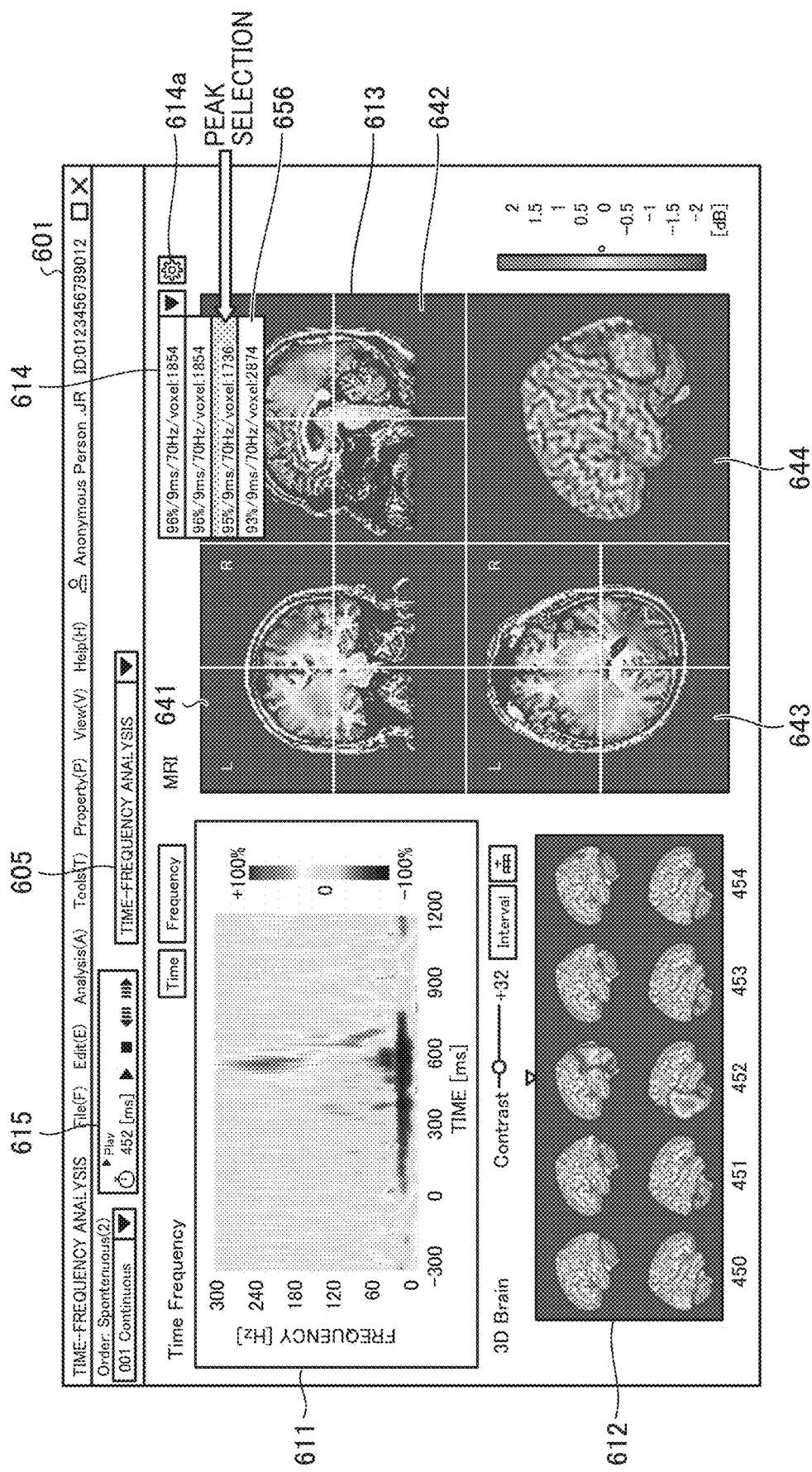
FIG. 59 is a diagram illustrating how a specific peak is selected from a drop-down peak list, according to embodiments of the present disclosure.

FIG. 59 is a diagram illustrating how a specific peak is selected from the drop-down peak list 614, according to the present embodiment.

Figure 60:
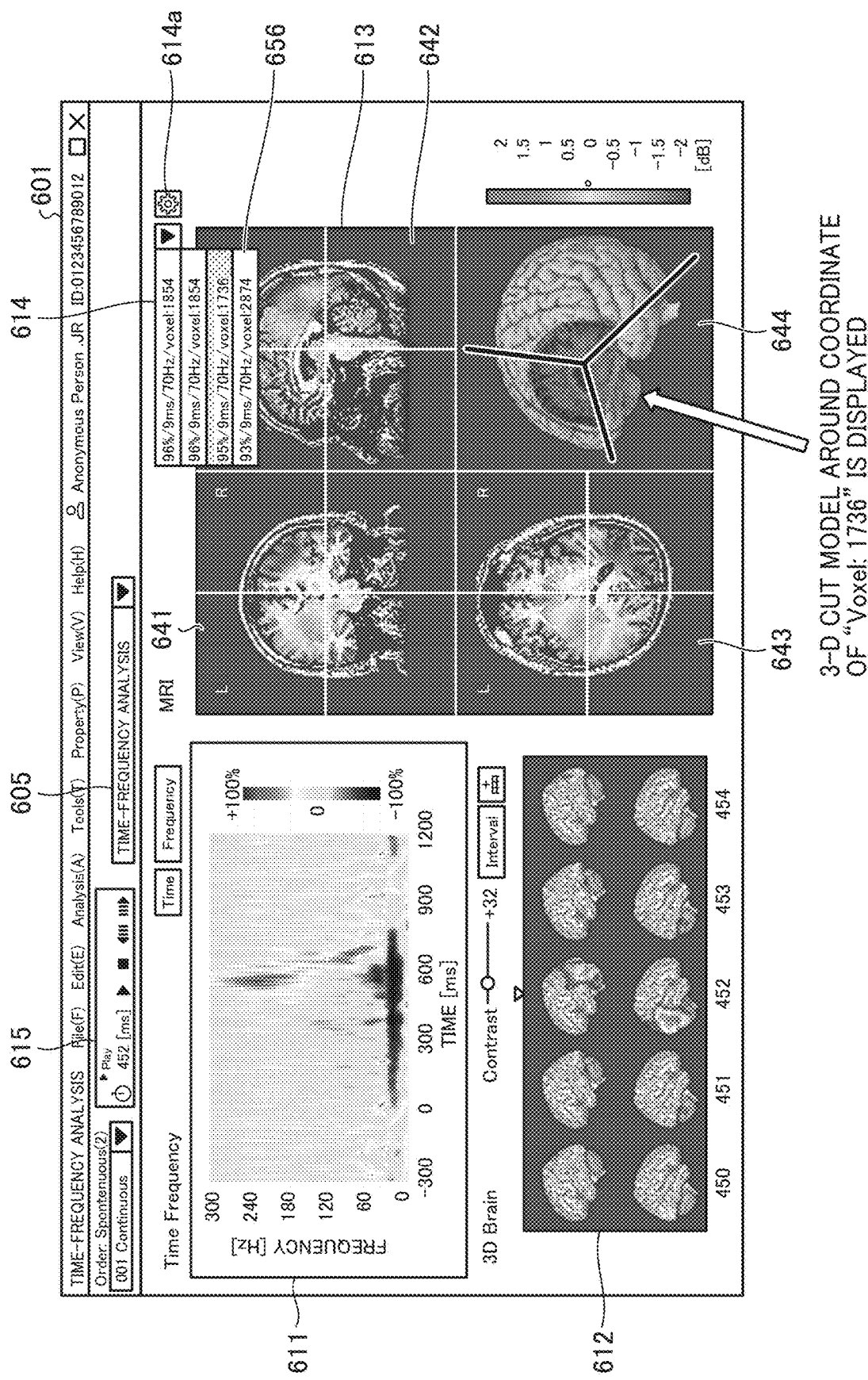
FIG. 60 is a diagram illustrating a state in which the peak selected from a pull-down peak list is reflected in a heat map, three-dimensional view, and a three-view head image, according to embodiments of the present disclosure.

FIG. 60 is a diagram illustrating a state in which the peak selected from the drop-down peak list 614 is reflected in the heat map 611, the three-dimensional view 612, and the three-view head image 613, according to the present embodiment.

In the peak list 614, the peaks in signal strength that meet a specified condition, which are extracted by the peak list controller 203, are registered. As illustrated in FIG. 56, the peak-list controller 203 controls the display to display a pull-down list 656, indicating a list of signal strengths registered as the peak list 614 is pulled down.

The above conditions for a peak in regard to the signal strength, which is extracted by the peak-list controller 203, can be configured by clicking or tapping the peak-list setting key 614a. Once the peak-list setting key 614a is clicked or tapped, the peak-list controller 203 controls the display to display a dialog box 655 where the conditions for a peak in regard to the extracted signal strength can be configured.

In the dialog box 655, first of all, how the peak data registered in the peak list 614 is to be sorted can be configured. When "Sort values of peaks in descending order" is selected in a dialog box 655, the peak-list controller 203 sorts the peaks of the signal strength in the peak data registered in the peak list 614 in descending order. By contrast, when "Sort levels of peaks (difference in height between top and bottom) in descending order" is selected in the dialog box 655, the peak-list controller 203 sorts the peak data registered in the peak list 614 in descending order of the difference between the signal strength at the peak point and the signal strength at the bottom of the peak.

Further, in the dialog box 655, what type of peak data is to be registered (listed) in the peak list 614 can be configured. When "All spatial peaks" is selected in the dialog box 655, the peak-list controller 203 extracts the spatial peaks, in the entirety of the brain, at each time and each frequency on the plane of time and frequency, and registers the extracted spatial peaks in the peak list 614. The term "spatial peaks" in the present embodiment indicates the peaks of signal strength of a biomedical signal of the time and frequency of interest in the entirety of the brain, and the signal strength in the peak spot 801 is greater than that of the area around that peak spot, like a peak spot 801 as illustrated in FIG. 57.

When "All peaks in time/frequency" is selected in the dialog box 655, the peak-list controller 203 extracts all the peaks in time and frequency from varying points of the plane of time and frequency in the entirety of the brain and registers the extracted peaks in the peak list 614. The term "peaks in time and frequency" in the present embodiment indicate the peaks of signal strength of a biomedical signal at a site of interest in the brain on the plane of time and frequency, like a peak spot 802 as illustrated in FIG. 58, and the signal strength in the peak spot 802 is greater than that of the area around that peak spot.

When "Spatial peaks in designated time/frequency" is selected in the dialog box 655, the peak-list controller 203 extracts the spatial peaks at the time and frequency specified on the plane of time and frequency in the entirety of the brain, and registers the extracted spatial peaks in the peak list 614. Note also that the specified time and frequency is not limited to a point, and the time and frequency may be selected or specified by an area or range.

When "Peaks in time/frequency at designated position" is selected in the dialog box 655, the peak-list controller 203 extracts all the peaks in time and frequency on the plane of time and frequency at the specified site of the brain, and registers the extracted peaks in the peak list 614. Note also that the designated position is not limited to a point, and the position may be selected or specified by an area or range. For example, when a peak on a visual area is to be extracted, the entirety of the occipital region of the brain may be specified. By so doing, a peak can easily be extracted as desired.

Next, operations are described that are performed when a specific item of peak data is selected from the peak list 614 in which several items of peak data are registered. When a specific item of peak data (for example, "95%/9 ms/70 Hz, voxel: 1736" as depicted in FIG. 59) is selected by the analyst from the pull-down list 656 of the peak list 614, the heat-map display control unit 211 controls the display to display the heat map 611 that corresponds to a desired point of the brain indicated by the selected item of peak data. In such a configuration, as described above with reference to FIG. 14, the heat-map display control unit 211 may specifically indicate on the heat map 611 the peak that is indicated by the selected item of peak data.

Moreover, the three-dimensional display control unit 212 controls the display to display the three-dimensional image of the brain of the time and frequency that the selected item of peak data indicates in the center of each row of the three-dimensional view 612, and further controls the display to display the three-dimensional images of the brain at times before and after the time indicated by the selected peak data in the three-dimensional view 612. In such cases, the heat maps that are superimposed on the multiple three-dimensional images of the brain in the three-dimensional view 612 may correspond to the signal strength of the biomedical signal with the frequency that the selected item of peak data indicates.

The sectional-view control unit 213 controls the display to display three-view images that go through the position of the brain indicated by the selected item of peak data, in the three-view head image 613. Further, the sectional-view control unit 213 may control the display to superimpose the heat map, which corresponds to the signal strength of the biomedical signal with the time and frequency that the selected item of peak data indicates, on the image of the brain in the three-dimensional image 644. As illustrated in FIG. 60, the sectional-view control unit 213 may controls the display to display a cut-model image, which is obtained by extracting a partial image of the brain in three-dimensional directions around the position of the brain indicated by the selected peak data, on the three-dimensional image 644.

As described above, a specific item of peak data is selected from the peak data registered in the peak list 614, and the heat map 611, the three-dimensional view 612, and the three-view head image 613 that correspond to the selected item of peak data are displayed accordingly. Due to such a configuration, to what position, time, and frequency of the brain the selected peak belongs can instantly be recognized. Further, the states of signal strength at the selected peak and at the time and frequency around the selected peak can be figured out, and the states of signal strength on the brain at the peak and around the peak can also be figured out on the heat map 611.

The operations when the replay control panel 615 on the time-frequency analysis screen 601 is manipulated are described below with reference to FIG. 61A to FIG. 63B.

FIG. 61A and FIG. 61B are diagrams illustrating how the viewing of the heat map 611 and the three-dimensional view 612 are viewed by operations on the replay control panel 615, according to the present embodiment.

Figure 62B:
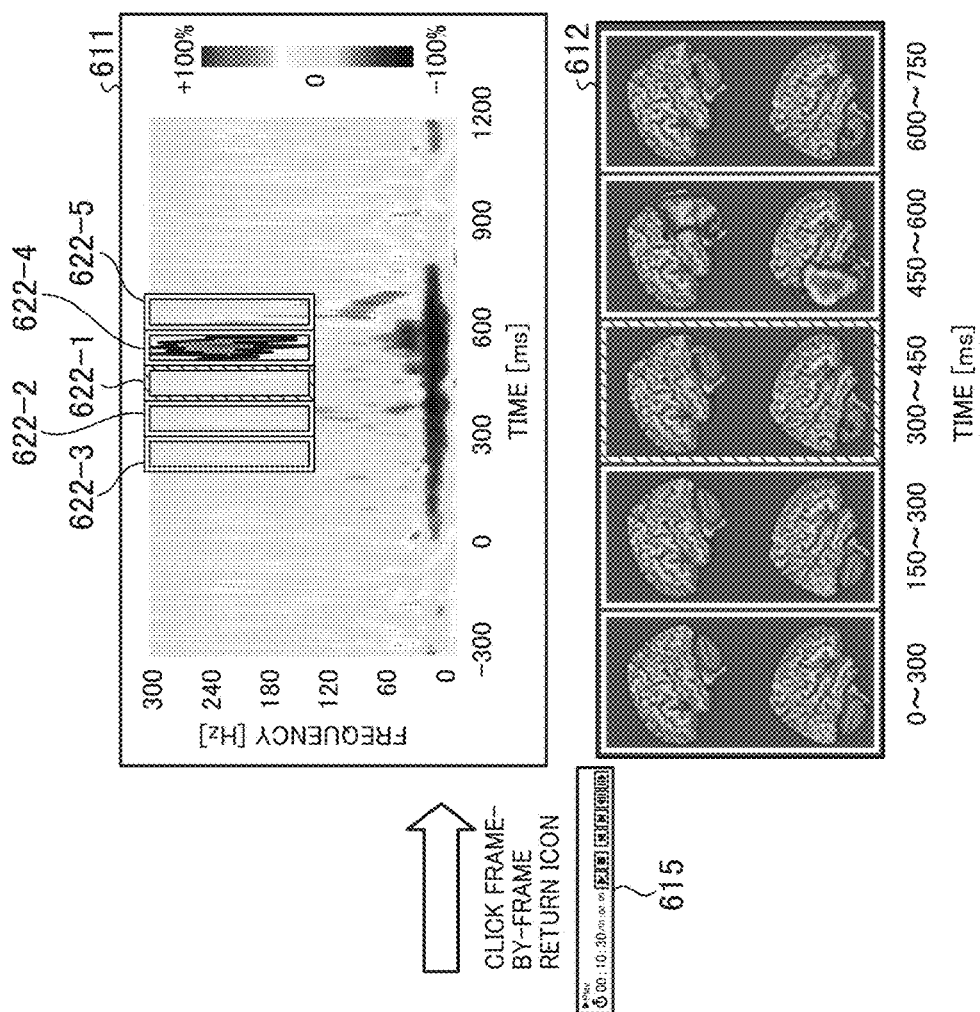
FIG. 62A and FIG. 62B are diagrams illustrating how the viewing of a heat map and a three-dimensional image are returned on a frame-by-frame basis by operations on a replay control panel, according to embodiments of the present disclosure.
Figure 62A:
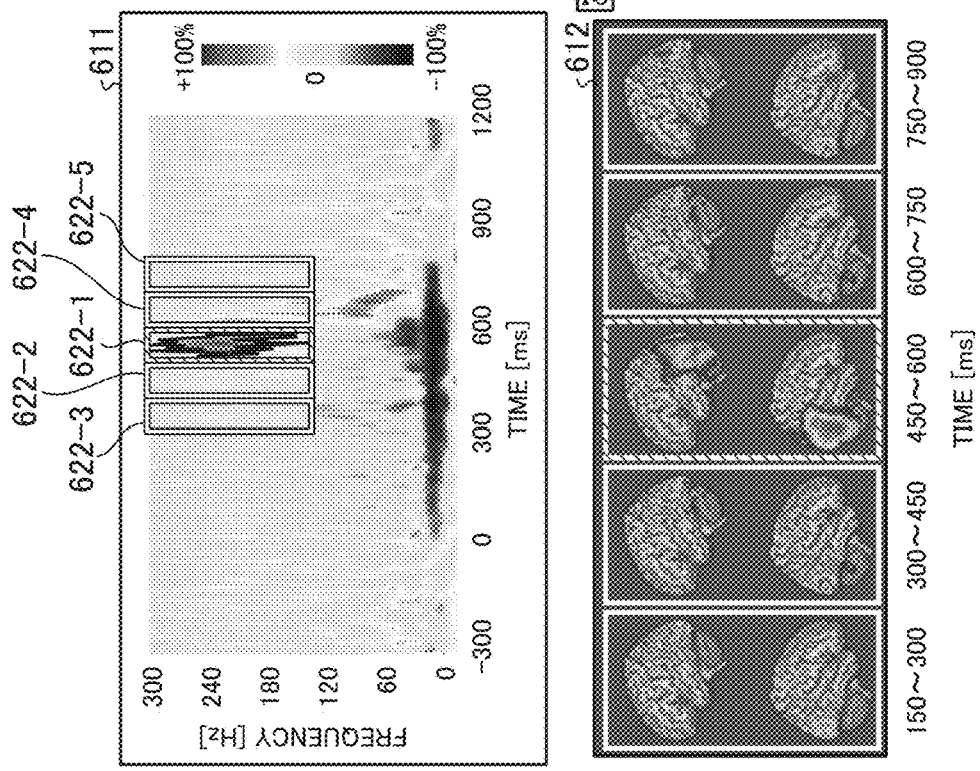

FIG. 62A and FIG. 62B are diagrams illustrating how the viewing of the heat map 611 and the three-dimensional view 612 are returned on a frame-by-frame basis by operations on the replay control panel 615, according to the present embodiment.

FIG. 63A and FIG. 63B are diagrams illustrating how the heat map 611 and the three-dimensional view 612 are advanced on a frame-by-frame basis by operations on the replay control panel 615, according to the present embodiment.

The replay control panel 615 is a user interface manipulated by the analyst to view the states of the heat map 611, the three-dimensional view 612, and the three-view head image 613 as time elapses.

For example, when the analyst touches or clicks the "replay" key on the replay control panel 615, as illustrated in FIG. 61A and FIG. 61B, the viewing control unit 214 instructs the heat-map display control unit 211 to move the specified area 622-1 specified on the heat map 611 and the related areas 622-2 to 622-5 around the specified area 622-1 in the right direction (i.e., the direction in which the time advances) as time elapses. As the specified area 622-1 and the related areas 622-2 to 622-5 are moved on the heat map 611, the viewing control unit 214 instructs the three-dimensional display control unit 212 to switch to the display of the three-dimensional images of the brain that correspond to the relevant multiple areas, as illustrated in FIG. 61A and FIG. 61B. As the specified area 622-1 is moved on the heat map 611 moves, the viewing control unit 214 instructs the sectional-view control unit 213 to display the heat map of the signal strength that corresponds to the range of time and frequency of the moving specified area 622-1 on the three-view images and the three-dimensional image 644.

When the analyst touches or clicks the "Frame-by-frame return" key on the replay control panel 615, as illustrated in FIG. 62A and FIG. 62B, the viewing control unit 214 instructs the heat-map display control unit 211 to move the specified area 622-1 specified on the heat map 611 and the related areas 622-2 to 622-5 around the specified area 622-1 in the left direction (i.e., the direction in which the time returns) by a certain length of time. As the specified area 622-1 and the related areas 622-2 to 622-5 are moved on the heat map 611, the viewing control unit 214 instructs the three-dimensional display control unit 212 to switch to the display of the three-dimensional images of the brain that correspond to the relevant multiple areas, as illustrated in FIG. 62A and FIG. 62B. As the specified area 622-1 is moved on the heat map 611 moves, the viewing control unit 214 instructs the sectional-view control unit 213 to display the heat map of the signal strength that corresponds to the range of time and frequency of the moved specified area 622-1 on the three-view images and the three-dimensional image 644.

When the analyst touches or clicks the "frame-by-frame advance" key on the replay control panel 615, as illustrated in FIG. 63A and FIG. 63B, the viewing control unit 214 instructs the heat-map display control unit 211 to move the specified area 622-1 specified on the heat map 611 and the related areas 622-2 to 622-5 around the specified area 622-1 in the right direction (i.e., the direction in which the time advances) by a certain length of time. As the specified area 622-1 and the related areas 622-2 to 622-5 are moved on the heat map 611, the viewing control unit 214 instructs the three-dimensional display control unit 212 to switch to the display of the three-dimensional images of the brain that correspond to the relevant multiple areas, as illustrated in FIG. 63A and FIG. 63B. As the specified area 622-1 is moved on the heat map 611 moves, the viewing control unit 214 instructs the sectional-view control unit 213 to display the heat map of the signal strength that corresponds to the range of time and frequency of the moved specified area 622-1 on the three-view images and the three-dimensional image 644.

When the analyst touches or clicks the "stop" key on the replay control panel 615, the viewing control unit 214 instructs each one of the heat-map display control unit 211, the three-dimensional display control unit 212, and the sectional-view control unit 213 to terminate its display operation on the heat map 611, the three-dimensional view 612, and the three-view head image 613.

When the analyst touches or clicks the "move to head" key on the replay control panel 615, the viewing control unit 214 instructs the heat-map display control unit 211 to move the specified area 622-1 specified on the heat map 611 to the head of the time. As the specified area 622-1 is moved on the heat map 611 moves, the viewing control unit 214 instructs the three-dimensional display control unit 212 to switch to the display of the three-dimensional images of the brain that correspond to the specified area 622-1. As the specified area 622-1 is moved on the heat map 611 moves, the viewing control unit 214 instructs the sectional-view control unit 213 to display the heat map of the signal strength that corresponds to the range of time and frequency of the moved specified area 622-1 on the three-view images and the three-dimensional image 644.

When the analyst touches or clicks the "move to end" key on the replay control panel 615, the viewing control unit 214 instructs the heat-map display control unit 211 to move the specified area 622-1 specified on the heat map 611 to the end of the time. As the specified area 622-1 is moved on the heat map 611 moves, the viewing control unit 214 instructs the three-dimensional display control unit 212 to switch to the display of the three-dimensional images of the brain that correspond to the specified area 622-1. As the specified area 622-1 is moved on the heat map 611 moves, the viewing control unit 214 instructs the sectional-view control unit 213 to display the heat map of the signal strength that corresponds to the range of time and frequency of the moved specified area 622-1 on the three-view images and the three-dimensional image 644.

Due to the viewing and displaying operation as described above, the changes over time in the distribution (heat map) of the signal strength indicated on the three-view head image 613 and the three-dimensional view 612 can be checked in moving images, and for example, the movement of the peaks over time can visually be checked.

How the heat map 611, the three-dimensional view 612, and the three-view head image 613 are initially displayed when the time-frequency analysis screen 601 is started (opened) according to the present embodiment are described below with reference to FIG. 64 to FIG. 66.

Figure 64:
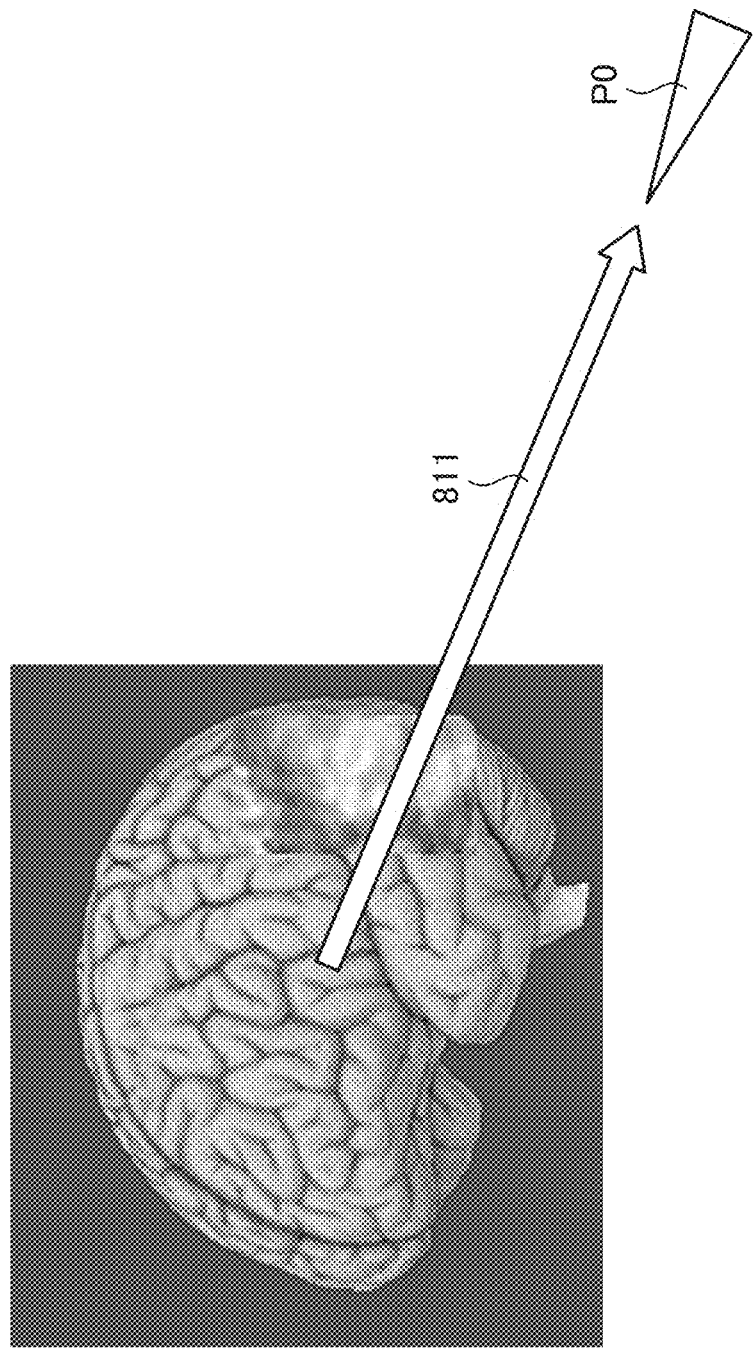
FIG. 64 is a diagram illustrating from what viewpoint the images are to be initially displayed with respect to a peak, according to embodiments of the present disclosure.

FIG. 64 is a diagram illustrating from what viewpoint the images are to be initially displayed with respect to a peak, according to the present embodiment.

Figure 65:
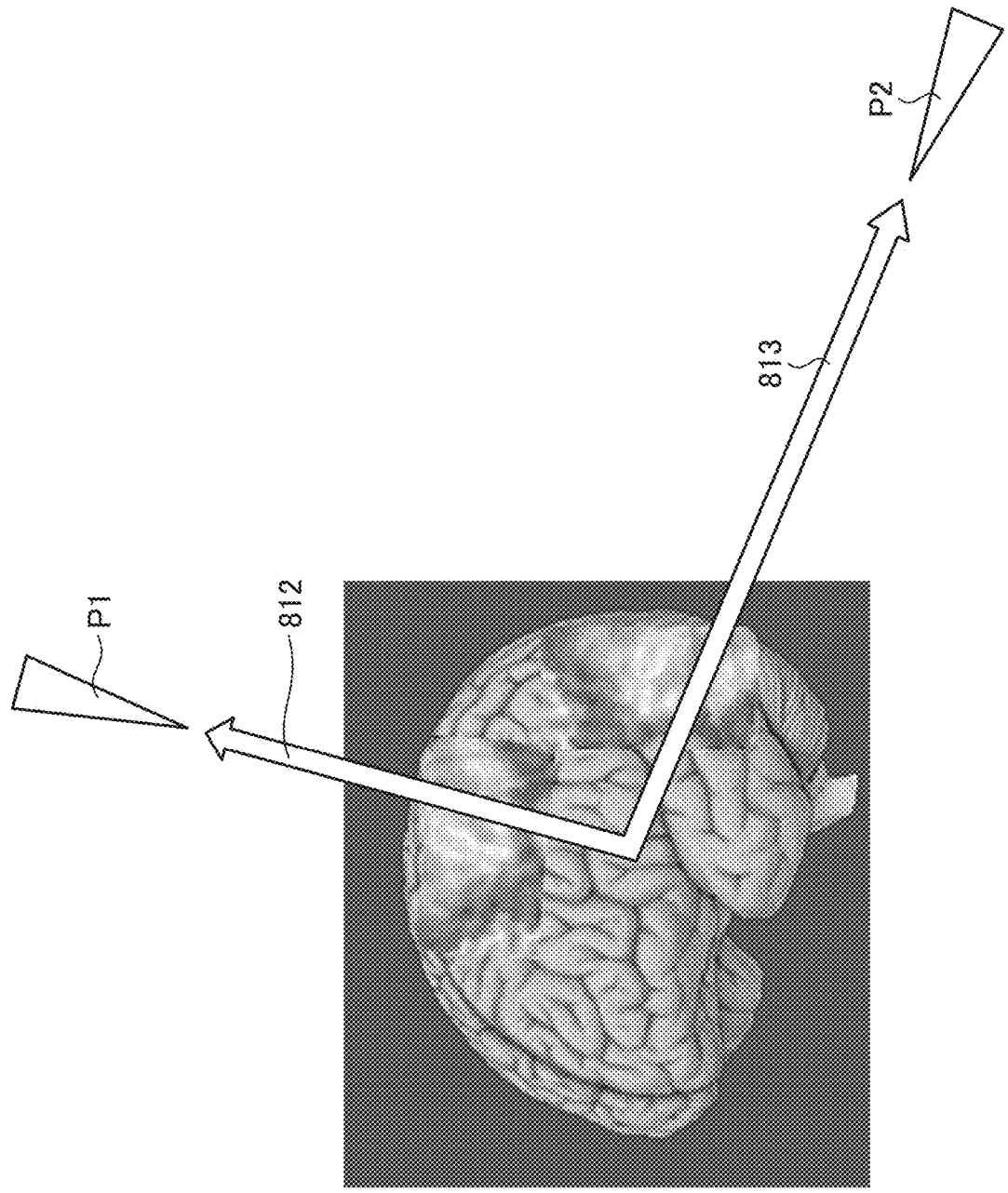
FIG. 65 is a diagram illustrating from what viewpoint the images are to be initially displayed with respect to a pair of peaks, according to embodiments of the present disclosure.

FIG. 65 is a diagram illustrating from what viewpoint the images are to be initially displayed with respect to a pair of peaks, according to the present embodiment.

Figure 66:
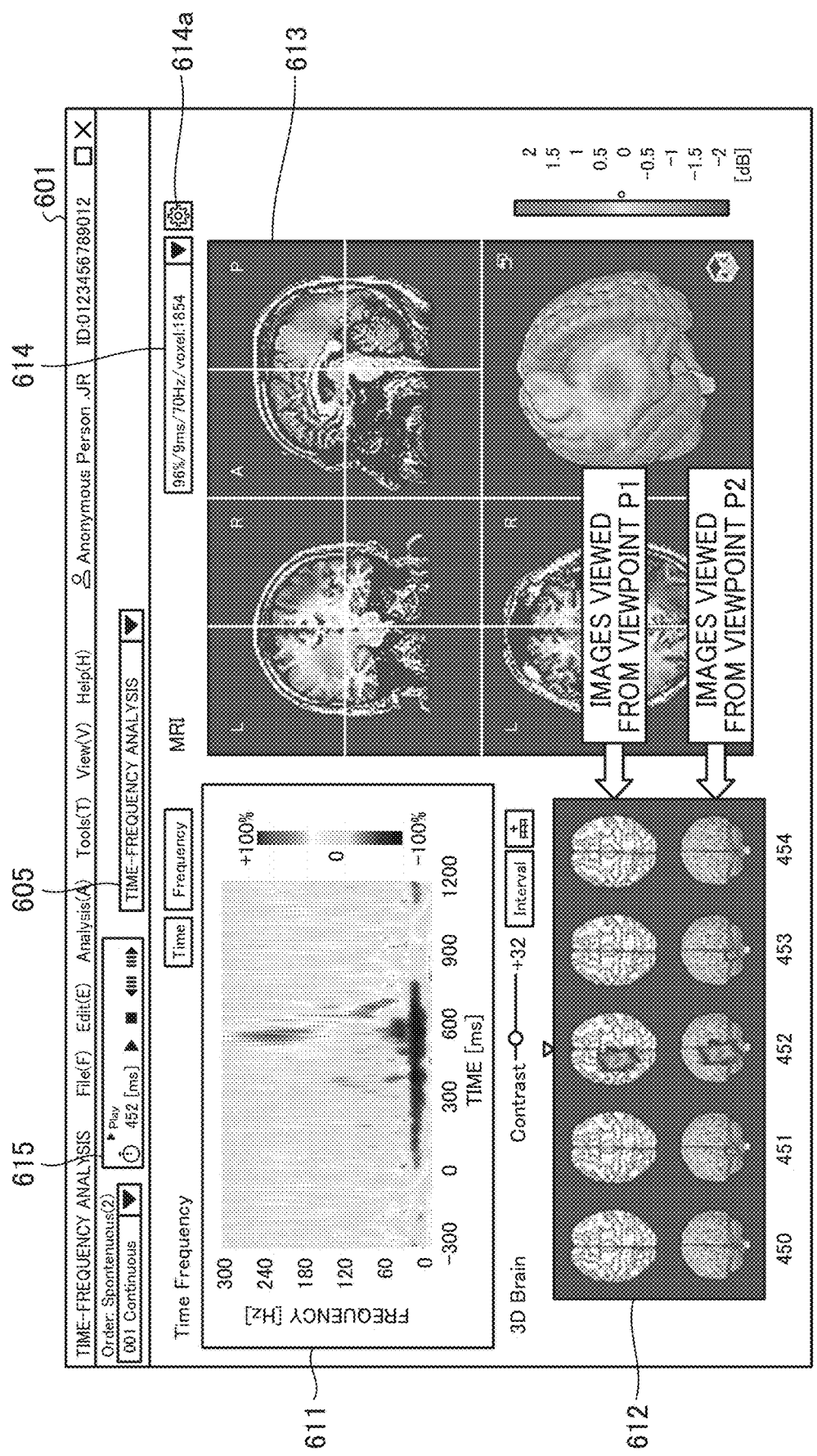
FIG. 66 is a diagram illustrating a state in which the images of the brain viewed from the viewpoints as illustrated in FIG. 65 are displayed as the initial display in three-dimensional view.

FIG. 66 is a diagram illustrating a state in which the images of the brain viewed from the viewpoints as illustrated in FIG. 65 are displayed in the three-dimensional view 612 as the initial display.

Some patterns of what kind of images are to be initially displayed as the heat map 611, the three-dimensional view 612, and the three-view head image 613 when the analyst started (opened) the time-frequency analysis screen 601 are described below.

For example, the analysis display controller 202 calculates the time and frequency and the position inside the brain where the signal strength is maximized throughout the entire range of time and frequency in the entirety of the brain. In such a case, the heat-map display control unit 211 controls the display to display the heat map 611 at the position inside the brain calculated by the analysis display controller 202. Moreover, the three-dimensional display control unit 212 controls the display to display the three-dimensional image of the brain, which corresponds to the time and frequency calculated by the analysis display controller 202, where the signal strength is maximized, in the three-dimensional view 612. The sectional-view control unit 213 controls the display to display three-view images that go through the position inside the brain calculated by the analysis display controller 202 in the three-view head image 613, and superimposes the heat map of time and frequency calculated by the analysis display controller 202, where the signal strength is maximized, on the three-view images and the three-dimensional image 644.

The analysis display controller 202 may calculate the position inside the brain where the average of signal strength is maximized throughout the entire range of time and frequency. In such a case, the heat-map display control unit 211 controls the display to display the heat map 611 at the position inside the brain calculated by the analysis display controller 202. Moreover, the three-dimensional display control unit 212 controls the display to display the three-dimensional image of the brain, which corresponds to the time and frequency on the displayed heat map 611 where the signal strength is maximized, on the three-dimensional view 612. The sectional-view control unit 213 controls the display to display three-view images that go through the position inside the brain calculated by the analysis display controller 202 in the three-view head image 613, and superimposes the heat map of the time and frequency, where the signal strength is maximized in the displayed heat map 611, on the three-view images and the three-dimensional image 644.

Alternatively, the analysis display controller 202 may compute and obtain the time and frequency where the average of the signal strength is maximized in the entirety of the brain. In such a case, the three-dimensional display control unit 212 controls the display to display the three-dimensional image of the brain that corresponds to the time and frequency calculated by the analysis display controller 202 on the three-dimensional view 612. The heat-map display control unit 211 computes and obtains the position inside the brain, which is displayed on the three-dimensional images of the three-dimensional view 612, where the signal strength is maximized in the heat map that corresponds to the time and frequency calculated by the analysis display controller 202, and controls the display to display the heat map 611 at the computed and obtained position. The sectional-view control unit 213 controls the display to display three-view images that go through the position inside the brain calculated by the heat-map display control unit 211 in the three-view head image 613, and superimposes the heat map of the time and frequency calculated by the analysis display controller 202 on the three-view images and the three-dimensional image 644.

Moreover, the three-dimensional display control unit 212 may control the display to display the heat map 611 at a position inside the brain indicated by the first item of peak data in the peak data registered in the peak list 614. Moreover, the three-dimensional display control unit 212 controls the display to display the three-dimensional image of the brain, which corresponds to the time and frequency indicated by the first item of peak data in the peak data registered in the peak list 614, on the three-dimensional view 612. The sectional-view control unit 213 controls the display to display three-view images that go through the position inside the brain indicated by the first item of peak data in the peak data registered in the peak list 614, in the three-view head image 613, and superimposes the heat map of the time and frequency indicated by the selected item of peak data, on the three-view images and the three-dimensional image 644.

Moreover, the three-dimensional display control unit 212 may control the display to display the heat map 611 at the position inside the brain that is preset depending on an object to be measured (for example, a visual area, auditory area, somatosensory area, motor area, and a language area are the preset parameters). Moreover, the three-dimensional display control unit 212 controls the display to display the three-dimensional image of the brain, which corresponds to the time and frequency that is preset depending on an object to be measured (for example, a visual area, auditory area, somatosensory area, motor area, and a language area), on the three-dimensional view 612. The sectional-view control unit 213 controls the display to display three-view images that are preset depending on an object to be measured (for example, a visual area, auditory area, somatosensory area, motor area, and a language area) and go through the position inside the brain in the three-view head image 613, and superimposes the heat map of the time and frequency indicated by the selected item of peak data, on the three-view images and the three-dimensional image 644.

The initial viewpoint of the three-dimensional images of the brain in the three-dimensional view 612 and the three-dimensional image 644 on the three-view head image 613 that are displayed when the analyst started (opened) the time-frequency analysis screen 601 is described below.

For example, the viewpoint that is preset depending on an object to be measured (for example, a visual area, auditory area, somatosensory area, motor area, and a language area) may be employed for the initial viewpoint. In such a configuration, the number of rows (viewpoints) in the three-dimensional view 612 is also preset in advance. For example, when the three-dimensional view 612 consists of two rows, two viewpoints need to be preset in advance. For example, when the language areas are to be measured, the viewpoints on the right and left sides of the brain are preset in advance.

A viewpoint from which the peak that is registered in the forefront of the peak list 614 can be observed most clearly may be employed for the initial viewpoint. More specifically as illustrated in FIG. 64, a viewpoint P0 may be set on a straight line 811 that connects the center of the brain and a peak, as the initial viewpoint.

A viewpoint that is determined based on a peak whose predetermined parameter in the peak list 614 (for example, the value of the peak (signal strength) or the level of the peak as illustrated in FIG. 57) exceeds a prescribed threshold may be employed for the initial viewpoint. For example, when there are two peaks that have exceeded the threshold, the three-dimensional view 612 may be displayed in two rows, and as illustrated in FIG. 65, viewpoints P1 and P2 may be set as the initial viewpoints on straight lines 812 and 813 that connect the center of the brain and the respective peaks. An example of such a configuration as above is illustrated in FIG. 66 in which the three-dimensional images of the brain viewed from the viewpoint P1 are displayed in the upper row of the three-dimensional view 612 and the three-dimensional images of the brain viewed from the viewpoint P2 are displayed in the lower row of the three-dimensional view 612.

As described above, in the present embodiment, particular time and frequency are specified on the heat map 611 that indicates the distribution of the signal strength of biomedical signals, and a threshold is determined based on the value of the signal strength at the specified position. Due to this configuration, the area of the time and frequency that has signal strength meeting a prescribed condition is automatically extracted. Accordingly, a concrete area of biomedical signals of interest at particular time and frequency can easily be extracted. As such a concrete area can be specified in an automatic manner, a more appropriate heat map can be superimposed on the three-view head image 613 and the three-dimensional view 612.

Moreover, in the above embodiment of the present disclosure, the heat map 611 indicating the time and frequency of a biomedical signal at a specific site of the brain or in a specific area of the brain is displayed. Moreover, the three-dimensional images indicative of the activity of the brain at times before and after the above time are displayed around the three-dimensional image on which a heat map indicative of the activity of the brain at the point designated on the heat map 611 or in the area designated on the heat map 611 is superimposed. In other words, some still images (i.e., three-dimensional images) that indicate the activity of the brain are advanced or returned on a frame-by-frame basis in the above embodiment of the present disclosure. Due to this configuration, still images that indicate the activity of the brain can appropriately and promptly be extracted, and the activity of the brain can easily be analyzed. Further, a conference or discussion can take place based on those images in an effective manner.

In the above embodiment of the present disclosure, once a specific item of peak data is selected from the peak data registered in the peak list 614, the heat map 611, the three-dimensional view 612, and the three-view head image 613 that correspond to the selected item of peak data are displayed. Due to such a configuration, to what position, time, and frequency of the brain the selected peak belongs can instantly be recognized. Further, the states of signal strength at the selected peak and at the time and frequency around the selected peak can be figured out, and the states of signal strength on the brain at the peak and around the peak can also be figured out on the heat map 611.

The viewpoint of the brain can be changed as desired in the three-dimensional view 612, and the changes based on the changed viewpoint of the brain can be reflected in the images of the brain in the same row or in a different row. Due to this configuration, the changes that are made in the viewpoint of a specific three-dimensional image (i.e., the target three-dimensional image) are automatically reflected in the other three-dimensional images, and the operability or efficiency improves. Furthermore, the images of the brain in multiple rows can be compared with each other, and thus the changes in activity among the images of the brain that are viewed from a corresponding viewpoint and are temporally close to each other can easily be checked. As the viewpoint of the brain that is drawn as three-dimensional images can be changed as desired, a firing point that cannot be viewed from one viewpoint can be checked.

As described above, in accordance with the various kinds of settings, the changes in viewpoint made on the three-dimensional image 644 in the three-view head image 613 can be reflected in the viewpoint of the three-dimensional images of the brain that are arranged in the three-dimensional view 612 in a chronological order. Due to such a configuration, changes in viewpoint similar to the changes in viewpoint made on the three-dimensional image 644 do not have to be made on the three-dimensional view 612 in a repetitive manner. Accordingly, the operability or efficiency improves. Furthermore, the changes in the state of the brain can be checked on the three-dimensional view 612 in chronological order with the viewpoint same as the viewpoint as changed in the three-dimensional image 644 or with the viewpoint corresponding to the viewpoint as changed in the three-dimensional image 644.

In the above embodiment of the present disclosure, a biomedical signal of the brain, which is an example of a biological site, is considered. However, no limitation is intended thereby, and it can be applied to the biomedical signals of a biological site such as a spinal cord and muscles. For example, in the case of lumber spine (lumbar vertebra), the three-dimensional view 612 that is used as an image of the brain may be displayed as illustrated in FIG. 67A, FIG. 67B, FIG. 67C, and FIG. 67D. FIG. 67A, FIG. 67B, FIG. 67C, and FIG. 67D illustrates how a lumbar signal is transmitted to the upper side in chronological order.

In the above embodiment of the present disclosure and its modifications, when at least some of the multiple functional units of the biomedical-signal measuring system 1 is implemented by executing a program, such a program may be incorporated in advance in a read only memory (ROM) or the like. The program to be executed by the biomedical-signal measuring system 1 according to the above embodiment of the present disclosure and its modifications may be installed for distribution in any desired computer-readable recording medium such as a compact disc, a read-only memory (CD-ROM), a flexible disk (FD), a compact disc-recordable (CD-R), and a digital versatile disk (DVD) in a file format installable or executable by a computer. The program that is executed in the biomedical-signal measuring system 1 according to the above embodiment of the present disclosure and its modifications may be provided upon being stored in a computer connected to a network such as the Internet and downloaded through the network. A program to be executed by the biomedical-signal measuring system 1 according to the above embodiment of the present disclosure and its modifications may be provided or distributed through a network such as the Internet. A program to be executed by the biomedical-signal measuring system 1 according to the above embodiment of the present disclosure and its modifications has module structure including at least one of the above-described functional units. Regarding the actual hardware related to the program, the CPU 101 reads and executes the program from the memory as described above (e.g., the ROM 103) to load the program onto the main memory (e.g., the RAM 102) to implement the above multiple functional units.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. An information processing device comprising circuitry configured to:
   obtain specific information of a first intensity distribution of a biomedical signal from a source, the first intensity distribution being a two-dimensional distribution of signal strength of the biomedical signal with respect to time and frequency, the biomedical signal including at least one of an electro-encephalography (EEG) signal and a magneto-encephalography (MEG) signal, and the specific information being displayed on a display;

extract, based on the specific information, a specified area of the first intensity distribution to obtain second intensity distribution of the biomedical signal to be superimposed on an image indicative of the source;

obtain, as the specific information, a value of the signal strength at a desired time and frequency;

perform binarization on the first intensity distribution, based on the value that serves as the specific information, to obtain a binarized image; and extract, as the specific area, a combined area in the binarized image, the combined area being an area including a pair of binarized images that have a small gap in between, the combined area including a point at the desired time and frequency.

2. The information processing device according to claim 1, wherein the first intensity distribution is a two-dimensional distribution of a statistical value, associated with a signal strength of the biomedical signal, with respect to time and frequency; and the circuitry is further configured to obtain, as the specific information, the statistical value associated with the signal strength at the desired time and frequency.

3. The information processing device according to claim 1, wherein the circuitry is further configured to:

use the value that serves as the specific information as a threshold; and makes a determination on a value of each pixel in the first intensity distribution based on the threshold to obtain the binarized image.

4. The information processing device according to claim 1, wherein the circuitry is further configured to:

use, as a threshold, a value obtained by multiplying the value that serves as the specific information by a prescribed rate; and makes a determination on a value of each pixel in the first intensity distribution based on the prescribed rate to obtain the binarized image.

5. The information processing device according to claim 1, wherein the circuitry is further configured to obtain the specific information at a position in the first intensity distribution specified by operation or input made through an input device.

6. The information processing device according to claim 1, wherein the circuitry is further configured to obtain the specific information of a desired area of the first intensity distribution.

7. The information processing device according to claim 6, wherein the circuitry is further configured to obtain the specific information of a representative point of the desired area in the first intensity distribution.

8. The information processing device according to claim 1, wherein the circuitry is further configured to extract, as the specified area, a rectangular area that circumscribes an area of the first intensity distribution extracted to obtain the second intensity distribution, based on the specific information.

9. The information processing device according to claim 1, wherein the specific information includes a plurality of items specific information;

the circuitry is further configured to obtain the plurality of items specific information from the first intensity distribution;

the specified area includes a plurality of specified areas;

the circuitry is further configured to extract the specified areas of the first intensity distribution based on the plurality of items specific information;

the second intensity distribution includes a plurality of items of second intensity distribution based on the plurality of specified areas; and the circuitry is further configured to control the display to superimpose each one of the plurality of items of second intensity distribution on a separate image indicative of the source.

10. The information processing device according to claim 1, wherein the specific information includes a plurality of items specific information;

the circuitry is further configured to obtain the plurality of items specific information from the first intensity distribution;

the specified area includes a plurality of specified areas;

the circuitry is further configured to extract the specified areas of the first intensity distribution based on the plurality of items specific information; and the circuitry is further configured to control the display to superimpose the second intensity distribution on an image indicative of the source, the second intensity distribution being based on the specified area selected from the plurality of specified areas by operation or input made through an input device.

11. A biomedical-signal measuring system comprising:

a measurement device configured to measure the biomedical signal of a test subject; and the information processing device according to claim 1.

12. The information processing device according to claim 1, wherein the second intensity distribution is a heat map based on the biomedical signal.

13. A method of processing information, the method comprising:

obtaining specific information of a first intensity distribution of a biomedical signal from a prescribed source, the first intensity distribution being a two-dimensional distribution of signal strength of the biomedical signal with respect to time and frequency, the biomedical signal including at least one of an electro-encephalography (EEG) signal and a magneto-encephalography (MEG) signal, and the specific information being displayed on a display;

extracting, based on the specific information, a specified area of the first intensity distribution to obtain second intensity distribution of the biomedical signal to be superimposed on an image indicative of the source;

obtaining, as the specific information, a value of the signal strength at a desired time and frequency;

performing binarization on the first intensity distribution, based on the value that serves as the specific information, to obtain a binarized image; and extracting, as the specific area, a combined area in the binarized image, the combined area being an area including a pair of binarized images that have a small gap in between, the combined area including a point at the desired time and frequency.

14. The method according to claim 13, wherein the first intensity distribution is a two-dimensional distribution of a statistical value associated with a signal strength of the biomedical signal, with respect to time and frequency; and the method further comprises, obtaining, as the specific information, the statistical value associated with the signal strength at the desired time and frequency.

15. The method according to claim 13, wherein the method further comprises:
   using the value that serves as the specific information as a threshold; and
   making a determination on a value of each pixel in the first intensity distribution based on the threshold to obtain the binarized image.

16. The method according to claim 13, wherein the method further comprises:
   using, as a threshold, a value obtained by multiplying the value that serves as the specific information by a prescribed rate; and
   making a determination on a value of each pixel in the first intensity distribution based on the prescribed rate to obtain the binarized image.

17. A computer-readable non-transitory recording medium storing a program for causing a computer to execute a method, the method comprising:
   obtaining specific information of a first intensity distribution of a biomedical signal from a prescribed source, the first intensity distribution being a two dimensional distribution of signal strength of the biomedical signal with respect to time and frequency, the biomedical signal including at least one of an electro-encephalography (EEG) signal, a magneto-encephalography (MEG) signal, and an electrocardiogram (ECG) signal, and the specific information being displayed on a display;
   extracting, based on the specific information, a specified area of the first intensity distribution to obtain second intensity distribution of the biomedical signal to be superimposed on an image indicative of the source;
   obtaining, as the specific information, a value of the signal strength at a desired time and frequency;
   performing binarization on the first intensity distribution, based on the value that serves as the specific information, to obtain a binarized image; and
   extracting, as the specific area, a combined area in the binarized image, the combined area being an area including a pair of binarized images that have a small gap in between, the combined area including a point at the desired time and frequency.

18. The computer-readable non-transitory recording medium according to claim 17, wherein
   the first intensity distribution is a two-dimensional distribution of a statistical value associated with a signal strength of the biomedical signal, with respect to time and frequency; and
   the method further comprises,
      obtaining, as the specific information, the statistical value associated with the signal strength at the desired time and frequency.

19. The computer-readable non-transitory recording medium according to claim 17, wherein the method further comprises:
   using the value that serves as the specific information as a threshold; and
   making a determination on a value of each pixel in the first intensity distribution based on the threshold to obtain the binarized image.

20. The computer-readable non-transitory recording medium according to claim 17, wherein the method further comprises:
   using, as a threshold, a value obtained by multiplying the value that serves as the specific information by a prescribed rate; and
   making a determination on a value of each pixel in the first intensity distribution based on the prescribed rate to obtain the binarized image.

* * * * *